US011390902B2

(12) United States Patent
Whitman et al.

(10) Patent No.: US 11,390,902 B2
(45) Date of Patent: *Jul. 19, 2022

(54) METHODS AND COMPOSITIONS FOR DISCRETE MELT ANALYSIS

(71) Applicant: LUMINEX CORPORATION, Austin, TX (US)

(72) Inventors: Douglas Whitman, Round Rock, TX (US); Jennifer Bernier, Austin, TX (US); William Wang, Round Rock, TX (US)

(73) Assignee: LUMINEX CORPORATION, Austin, TX (US)

( * ) Notice: Subject to any disclaimer, the term of this patent is extended or adjusted under 35 U.S.C. 154(b) by 572 days.

This patent is subject to a terminal disclaimer.

(21) Appl. No.: 16/253,715

(22) Filed: Jan. 22, 2019

(65) Prior Publication Data

US 2019/0226008 A1 Jul. 25, 2019

Related U.S. Application Data

(60) Provisional application No. 62/620,298, filed on Jan. 22, 2018.

(51) Int. Cl.
| | |
|---|---|
| *G01N 33/00* | (2006.01) |
| *C12Q 1/6806* | (2018.01) |
| *C12Q 1/6851* | (2018.01) |
| *C12Q 1/686* | (2018.01) |
| *C12Q 1/6823* | (2018.01) |
| *C07H 21/04* | (2006.01) |
| *C07H 21/00* | (2006.01) |

(52) U.S. Cl.
CPC .......... *C12Q 1/6806* (2013.01); *C12Q 1/686* (2013.01); *C12Q 1/6823* (2013.01); *C12Q 1/6851* (2013.01); *C12Q 2525/301* (2013.01); *C12Q 2527/101* (2013.01); *C12Q 2527/107* (2013.01); *C12Q 2527/143* (2013.01); *C12Q 2531/113* (2013.01)

(58) Field of Classification Search
None
See application file for complete search history.

(56) References Cited

U.S. PATENT DOCUMENTS

| | | | |
|---|---|---|---|
| 5,200,313 A * | 4/1993 | Carrico ................... | C12Q 1/68 435/6.11 |
| 6,862,252 B1 | 3/2005 | Hickling | |
| 9,169,514 B2 * | 10/2015 | Jia ........................ | C12Q 1/6883 |
| 9,284,607 B2 * | 3/2016 | Fu ......................... | C12Q 1/6876 |
| 9,982,291 B2 * | 5/2018 | Johnson et al. ..... | C12Q 1/6816 |
| 2005/0053950 A1 | 3/2005 | Zudaire Ubani et al. | |
| 2011/0151461 A1 | 6/2011 | Link et al. | |
| 2012/0021423 A1 | 1/2012 | Colston, Jr. et al. | |
| 2013/0095479 A1 | 4/2013 | Wangh et al. | |
| 2013/0302792 A1 | 11/2013 | Hindson et al. | |
| 2015/0308957 A1 | 10/2015 | Okura et al. | |
| 2017/0088879 A1 | 3/2017 | Keys et al. | |
| 2017/0226576 A1 | 8/2017 | Caplin | |
| 2017/0247750 A1 | 8/2017 | Chun et al. | |
| 2017/0321259 A1 | 11/2017 | Johnson et al. | |
| 2017/0372002 A1 | 12/2017 | Yang et al. | |
| 2018/0073056 A1 | 3/2018 | Kozlov et al. | |
| 2018/0073064 A1 | 3/2018 | Kozlov et al. | |
| 2018/0087090 A1 | 3/2018 | Furlan | |

FOREIGN PATENT DOCUMENTS

| | | |
|---|---|---|
| CN | 102112632 | 6/2011 |
| CN | 106715720 | 5/2017 |
| WO | WO 2010/068576 | 6/2010 |
| WO | WO 2012/096430 | 7/2012 |
| WO | WO 2014/028882 | 2/2014 |
| WO | WO 2015/023616 | 2/2015 |
| WO | WO 2016/184902 | 11/2016 |
| WO | WO 2017/059049 | 4/2017 |
| WO | WO 2018/094091 | 5/2018 |

OTHER PUBLICATIONS

International Search Report and Written Opinion, issued in PCT/US2019/014512, dated Mar. 29, 2019.
Extended Search Report and Opinion issued in European Patent Application No. 19741859.3, dated Oct. 26, 2021.
Official Action issued in Chinese Patent Application No. 201980009454.6, dated Oct. 26, 2021.

* cited by examiner

*Primary Examiner* — Bradley L. Sisson
(74) *Attorney, Agent, or Firm* — Parker Highlander PLLC

(57) ABSTRACT

Methods and reagent for determining the presence and/or for quantifying the amount of a target nucleic acid sequences in a sample are provided. In some aspects, the methods comprise performing a melt analysis by detecting, a signal from a probe at a temperature that is lower than the Tm of the probe and a signal at a temperature that is higher than the Tm of the probe, without detecting a signal at the Tm of the probe.

25 Claims, 23 Drawing Sheets
Specification includes a Sequence Listing.

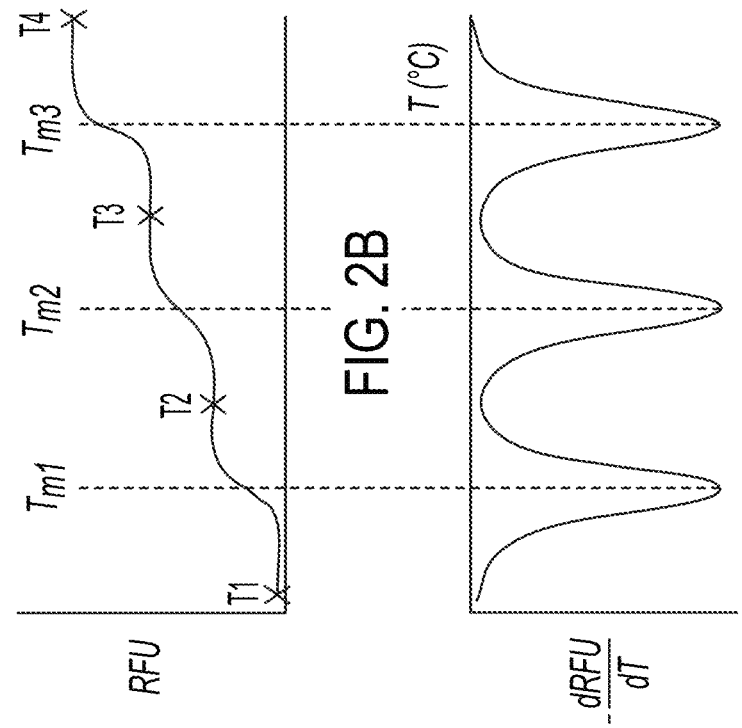
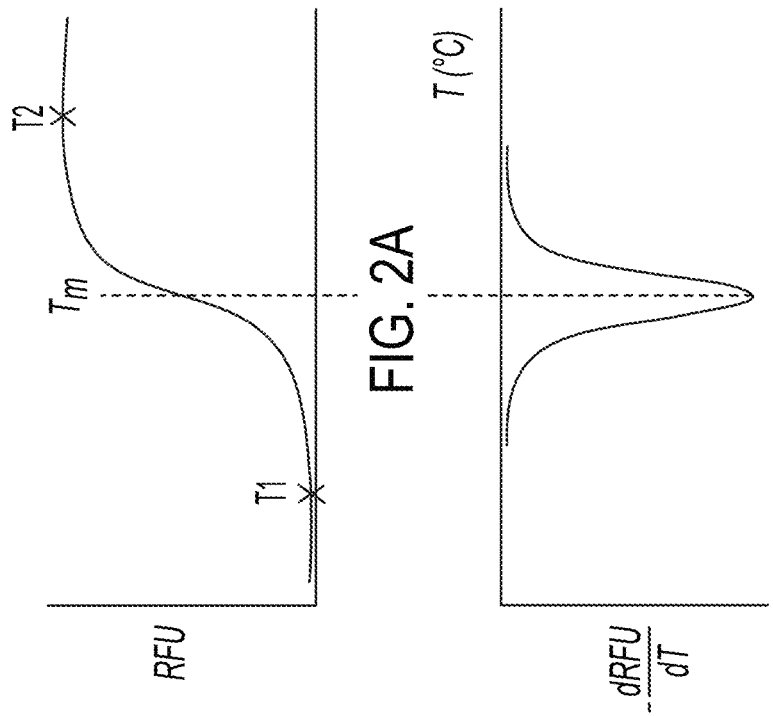

Pre-Amplification Image

| A | B | C | AB | AC | BC |
|---|---|---|----|----|----|
| ABC | | A | B | C | AB |
| AC | BC | ABC | | A | B |
| C | AB | AC | BC | ABC | |
| A | B | C | AB | AC | BC |
| ABC | | A | B | C | AB |

FIG. 3

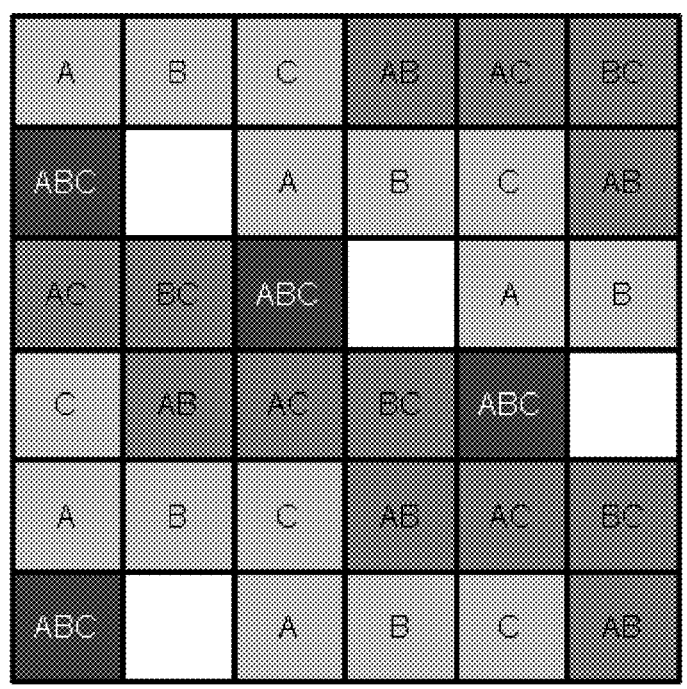 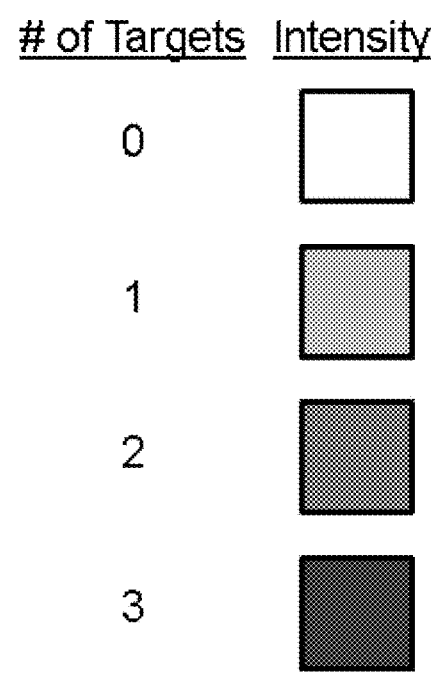
FIG. 4

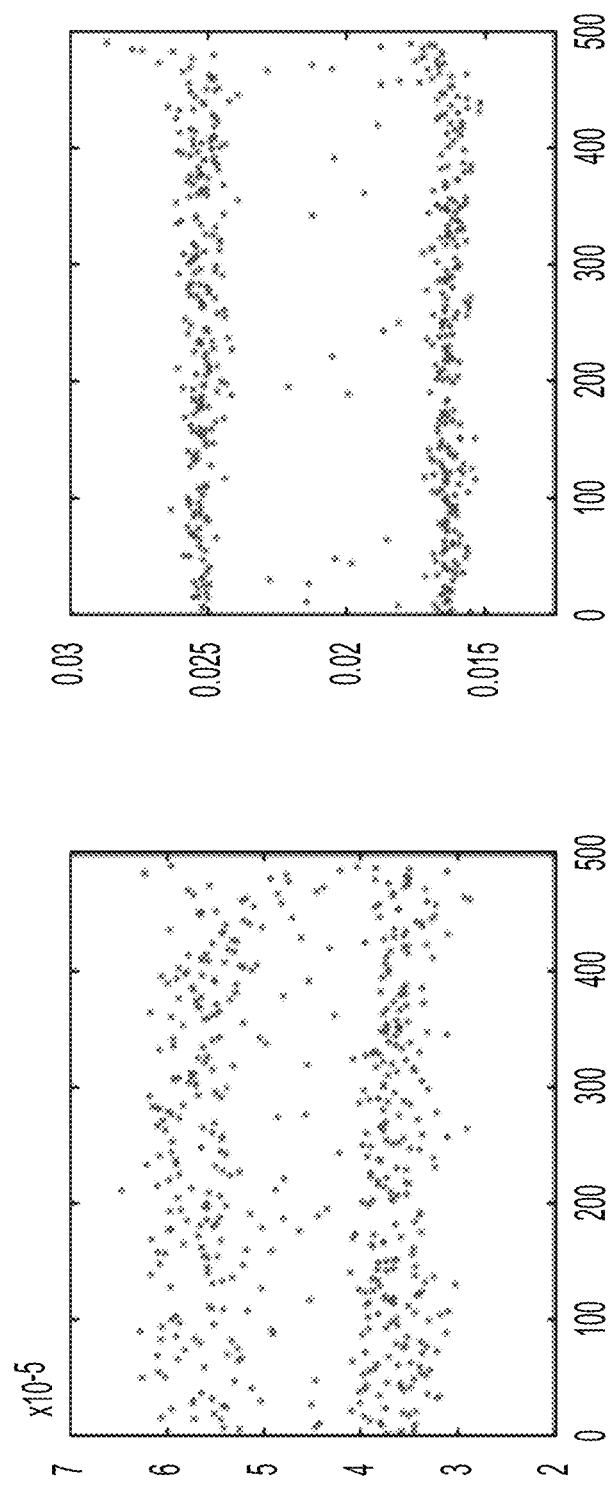

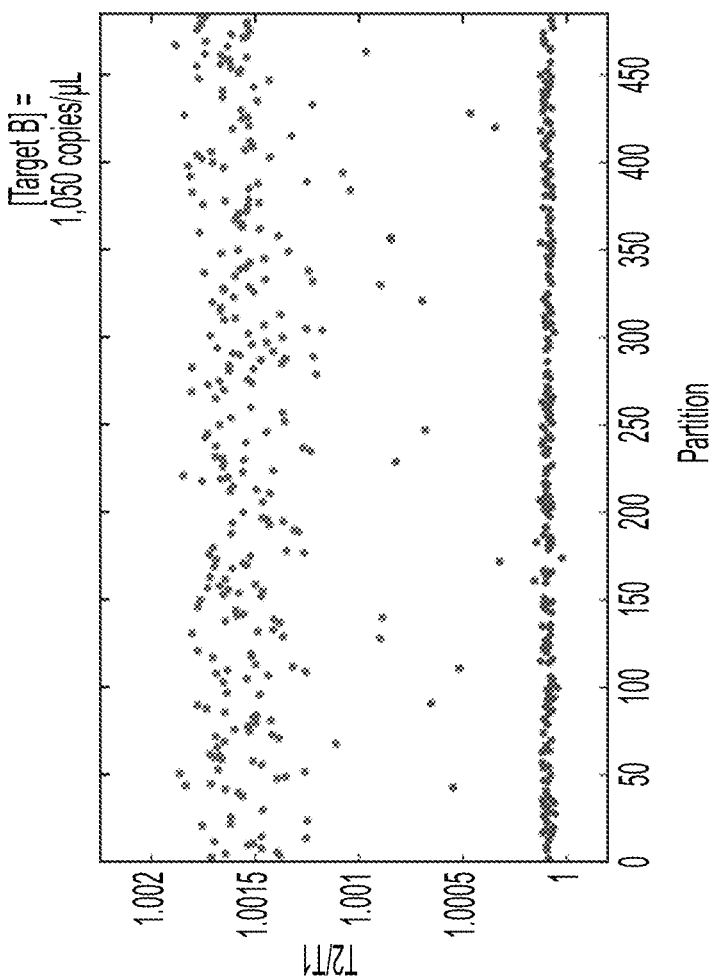
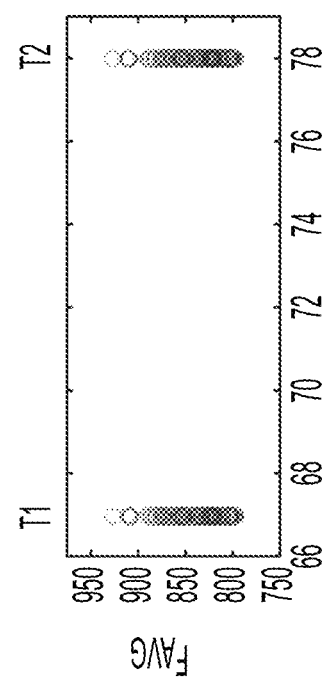
FIG. 12A
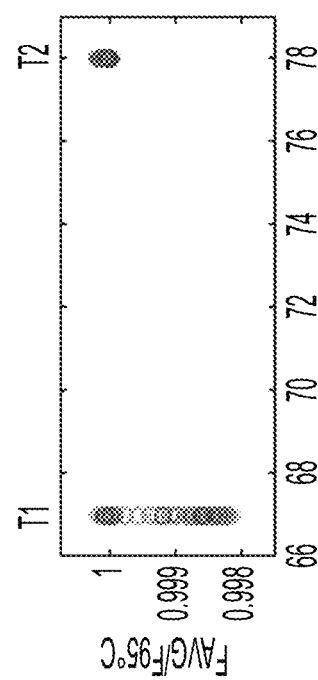
FIG. 12B
FIG. 12C

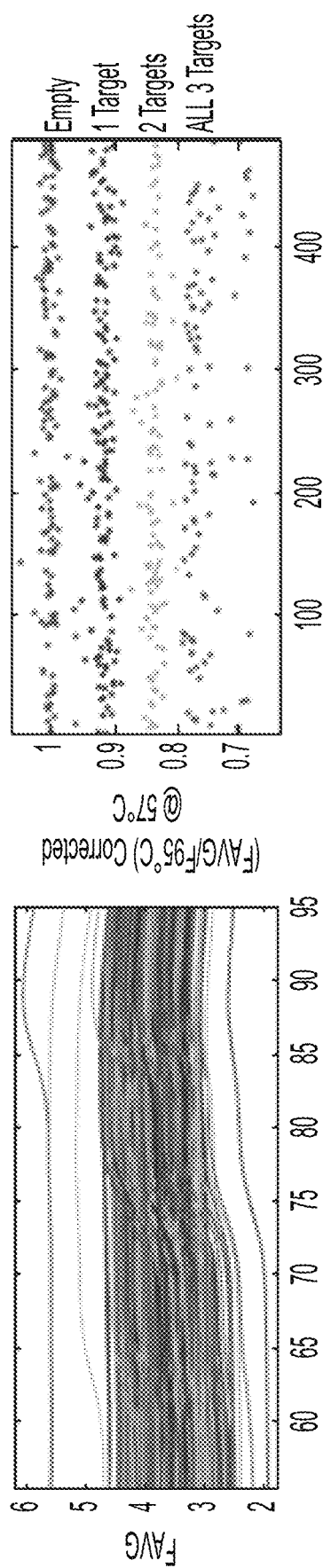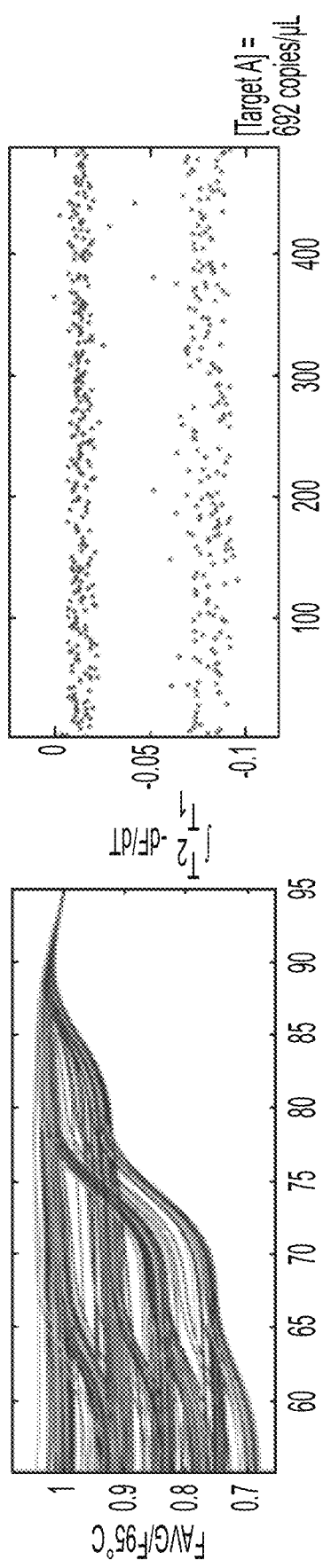
FIG. 13A  FIG. 13B  FIG. 13C  FIG. 13D

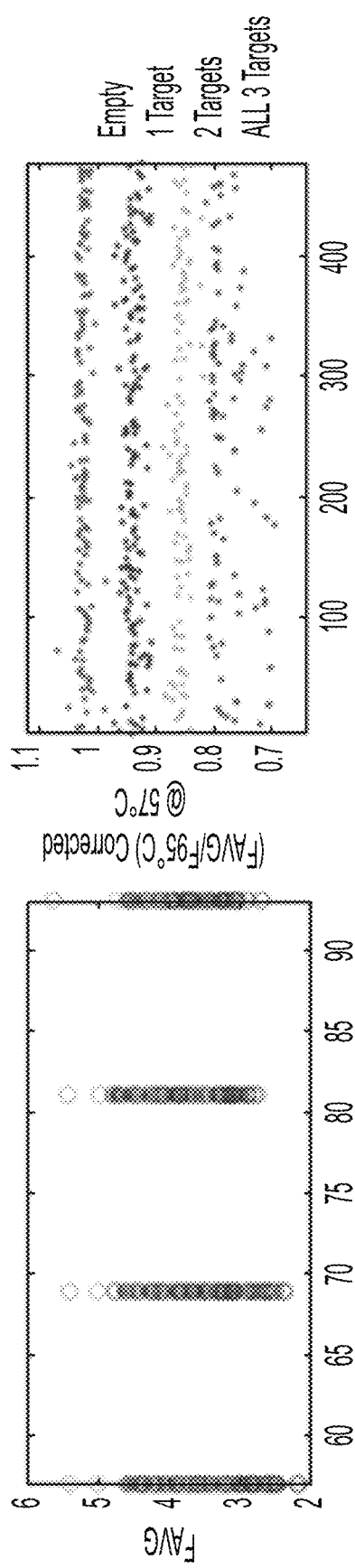
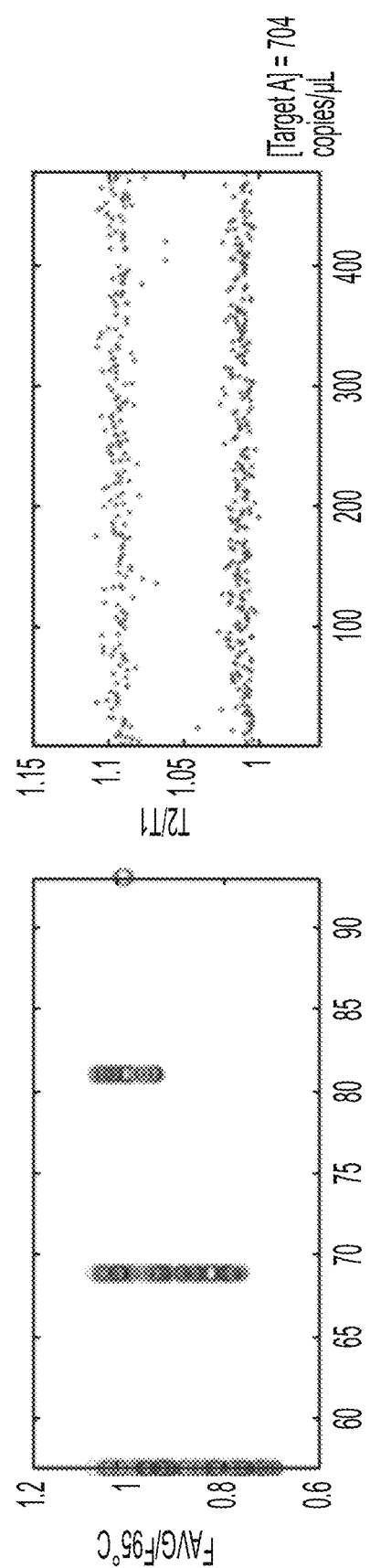
FIG. 14A  FIG. 14B  FIG. 14C  FIG. 14D

SEQUENCE LISTING

```
<160> NUMBER OF SEQ ID NOS: 12

<210> SEQ ID NO 1
<211> LENGTH: 24
<212> TYPE: DNA
<213> ORGANISM: Artificial Sequence
<220> FEATURE:
<223> OTHER INFORMATION: Synthetic primer

<400> SEQUENCE: 1
gcaagatacc atttatcaat gaag                                          24

<210> SEQ ID NO 2
<211> LENGTH: 25
<212> TYPE: DNA
<213> ORGANISM: Artificial Sequence
<220> FEATURE:
<223> OTHER INFORMATION: Synthetic primer

<400> SEQUENCE: 2
ggtgtcaatt ttcttatatc ataat                                         25

<210> SEQ ID NO 3
<211> LENGTH: 63
<212> TYPE: DNA
<213> ORGANISM: Artificial Sequence
<220> FEATURE:
<223> OTHER INFORMATION: Synthetice probe

<400> SEQUENCE: 3
ttctcttctc tttcattcac ataacgccaa aaaacccgtt atgtcctcca gttcccatat   60
ttg                                                                 63

<210> SEQ ID NO 4
<211> LENGTH: 198
<212> TYPE: DNA
<213> ORGANISM: Artificial Sequence
<220> FEATURE:
<223> OTHER INFORMATION: Synthetic ultramer

<400> SEQUENCE: 4
atgactaagc aagataccat ttatcaatga agaagagttt attgtagaga aaataagagt   60
aatgtttgtc caacattaac tgcaaatatg ggaactggag gacataacgt tccattaata  120
aaggataatt atgatataag aaaattgaca ccagaagaat gtgtggcatt tcaaggtttt  180
ccttcagaat ttcaattc                                                198
```

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
gtggaggatg acactttcg                                                    20

<210> SEQ ID NO 6
<211> LENGTH: 25
<212> TYPE: DNA
<213> ORGANISM: Artificial Sequence
<220> FEATURE:
<223> OTHER INFORMATION: Synthetic primer

<400> SEQUENCE: 6
attgaattga gagaactgtt agata                                             25

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
attccttagg taccgtcaga                                                   20

<210> SEQ ID NO 8
<211> LENGTH: 25
<212> TYPE: DNA
<213> ORGANISM: Artificial Sequence
<220> FEATURE:
<223> OTHER INFORMATION: Synthetic primer

<400> SEQUENCE: 8
caacaaagtt aaagctagtg tttag                                             25

<210> SEQ ID NO 9
<211> LENGTH: 67
<212> TYPE: DNA
<213> ORGANISM: Artificial Sequence
<220> FEATURE:
<223> OTHER INFORMATION: Synthetice probe

<400> SEQUENCE: 9
atatatatat ataagaat tctgccaaaa aaacccaga attcttccct aagaaaagga          60
gtttacg                                                                 67

<210> SEQ ID NO 10
<211> LENGTH: 62
<212> TYPE: DNA
<213> ORGANISM: Artificial Sequence
<220> FEATURE:
<223> OTHER INFORMATION: Synthetice probe

<400> SEQUENCE: 10
cctcccctcc cctcccttc accatccaaa aaaccatggt gaucaatcct taacactgct       60
tt                                                                      62

<210> SEQ ID NO 11

```
<211> LENGTH: 111
<212> TYPE: DNA
<213> ORGANISM: Artificial Sequence
<220> FEATURE:
<223> OTHER INFORMATION: Synthetic oligonucleotide

<400> SEQUENCE: 11
ccctgacgca gcaacgccgc gtggaggatg acacttttcg gagcgtaaac tccttttctt      60
agggaagaat tctgacggta cctaaggaat aagcaccggc taactccgtg c              111

<210> SEQ ID NO 12
<211> LENGTH: 143
<212> TYPE: DNA
<213> ORGANISM: Artificial Sequence
<220> FEATURE:
<223> OTHER INFORMATION: Synthetic oligonucleotide

<400> SEQUENCE: 12
atgctaatta caaaaacagg attgaattga gagaactgtt agataaaaac ctgtttaaag      60
cagtgttaag gattgatcac catcccaatg aagatgatct aaacactagc tttaactttg     120
ttgaagaaag ctatgtagct tgt                                             143
```

METHODS AND COMPOSITIONS FOR DISCRETE MELT ANALYSIS

This application claims the benefit of U.S. Provisional Patent Application No. 62/620,298, filed Jan. 22, 2018, the entirety of which is incorporated herein by reference.

INCORPORATION OF SEQUENCE LISTING

The sequence listing that is contained in the file named "LUMN_P0144US_ST25.txt", which is 3.2 KB (as measured in Microsoft Windows®) and was created on Jan. 22, 2019, is filed herewith by electronic submission and is incorporated by reference herein.

BACKGROUND OF THE INVENTION

1. Field of the Invention

The present invention relates generally to the field of molecular biology. More particularly, it concerns methods for identifying and quantifying nucleic acid targets in biological samples.

2. Description of Related Art

Melt analysis of duplex nucleic acids utilizes melt or anneal peaks to discriminate amplicon identity, but melt peaks are not easily distinguishable in amplicons or nucleic acid duplexes that melt near the same temperature unless the amplicons or nucleic acids are distinctly labeled. Furthermore, melt analysis is generally performed after target amplification and increases turnaround time of an assay due to the time required to slowly increase or decrease temperature of the sample and acquire images at multiple temperatures.

Digital polymerase chain reaction (dPCR) is a refinement of conventional PCR and can be used to directly quantify and clonally amplify nucleic acids, e.g., DNA, cDNA or RNA. Conventional PCR is generally used for measuring nucleic acid amounts and is carried out by a single reaction per sample. Utilizing dPCR methodology, a single reaction is also carried out on a sample, however the sample is separated into a large number of partitions and the reaction is carried out in each partition individually. This separation allows for a more reliable collection and sensitive measurement of nucleic acid amounts.

Current methods for dPCR rely on end point PCR to quantify the presence of target nucleic acids. This end point PCR analysis is limiting in multiple ways. First, the use of DNA intercalating dyes and TaqMan probes results in the potential for non-specific amplification to produce a false positive signal in a partition. Additionally, existing commercial systems have limitations in the number of available fluorescence channels which limit the ability to detect multiple targets. Lastly, classification of partitions as positive or negative relies solely on endpoint fluorescence intensity of a partition.

In a well-designed assay, good separation is desired in the average intensity values of positive and negative partitions. However, more often in digital PCR, a phenomenon known as "rain" confounds the classification of partitions into these two categories. Rain may be described as partitions of intermediate intensity post amplification. Positive partitions may have lower than predicted intensity due to incomplete amplification and negative partitions may have higher than predicted intensity due to non-specific amplification. This is in addition to fluorescence intensity variations due to instrument optical and thermal system variability.

Efforts to apply melt analysis to dPCR reactions in an analogous manner as has been applied in quantitative, real-time PCR (qPCR), have identified potential drawbacks. One of the drawbacks is the time required to acquire a melt profile in dPCR applications. Images must be acquired over a large number (e.g. up to 30,000) of partitions at many different temperatures, such as around 35-70 unique temperatures, which can be very time consuming. Typical exposure times are on the order of 1s, not accounting for time to turn LED on prior to imaging. The footprint for 30,000 1 nL partitions could be on the order of 12.5 mm×12.5 mm. Typical field of view dimensions to achieve appropriate resolution on 1 nL partitions is on the order of 6 mm×6 mm. Thus, to generate a melt profile at a resolution of 0.5° C., 630 images may be required for a single sample and image acquisition alone may take more than 10 minutes, not accounting for melt acquisition in additional channels. This method also requires maintaining the partitions at successively higher temperatures for extended periods and extended exposure of the sample to light which can degrade the fluorescence signal through photobleaching.

It would be desirable to find improved methods for performing melt analysis in dPCR applications to reduce the time required for data collection and analysis, and to improve specificity of the reaction to ensure accurate results.

SUMMARY OF THE INVENTION

In some embodiments, the present disclosure provides a method of performing a melt analysis on a labeled duplex nucleic acid in a reaction mixture, the labeled duplex nucleic acid having a predetermined Tm and the method comprising: (a) measuring a first signal from a labeled duplex nucleic acid at a first temperature that is lower than the predetermined Tm of the labeled duplex nucleic acid; (b) measuring a second signal from the labeled duplex nucleic acid at a second temperature that is higher than the predetermined Tm of the labeled duplex nucleic acid; and (c) determining if the labeled duplex nucleic acid is the result of specific hybridization of a target-specific probe to a target sequence by comparing the first signal and the second signal, wherein a change between the first signal and the second signal indicates that the labeled duplex nucleic acid is the result of specific hybridization of a target-specific probe to a target sequence in the reaction mixture and wherein a signal is not measured at the predetermined Tm of the labeled duplex nucleic acid. In some aspects a method is provided comprising performing a melt analysis on a labeled duplex nucleic acid in a reaction mixture, the labeled duplex nucleic acid having a predetermined Tm and the method comprising (a) measuring a first signal from a labeled duplex nucleic acid at a first temperature that is lower than the predetermined Tm of the labeled duplex nucleic acid; (b) measuring a second signal from the labeled duplex nucleic acid at a second temperature that is higher than the predetermined Tm of the labeled duplex nucleic acid without measuring a signal at the predetermined Tm; and (c) comparing the first signal and the second signals determining that the labeled duplex nucleic acid is the result of specific hybridization of a target-specific probe to a target sequence in the reaction mixture when there is a change between the first and second signals. In some aspects, the target-specific probe is a cleavable probe that is cleaved upon specific hybridization of the target-specific probe to the target sequence. In some aspects, the target-specific probe is capable of adopting a first temperature-dependent conformation or a second temperature-dependent conformation. In some aspects, signal is not measured within 2 degrees Celsius of the predetermined Tm of the labeled duplex nucleic acid. In some aspects, is not measured within 5 degrees Celsius of the predetermined Tm of the labeled duplex nucleic acid. In some aspects, the difference between the first temperature and the second temperature is greater than two degrees Celsius. In some aspects, the difference between the first temperature and the second temperature is greater than 5 degrees Celsius. In some aspects, the difference between the first temperature and the second temperature is greater than 8 degrees Celsius. In some aspects, the method further comprises the steps of measuring a third signal at a third temperature at which all labeled duplex nucleic acids in the reaction mixture are denatured, and normalizing the first and second signals relative to the third signal. In some aspects, the reaction mixture contains at least two different duplex nucleic acids, each having a unique, predetermined Tm, and each different duplex nucleic acid having the same signal-generating label, further comprising the steps of: e) measuring a signal from each different labeled duplex nucleic acid at a temperature that is lower than the unique, predetermined Tm of the labeled duplex nucleic acid and a temperature that is higher than the unique, predetermined Tm of the labeled duplex nucleic acid, and wherein, for each different labeled duplex nucleic acid, a change in signal measured at the temperature that is lower than the unique, predetermined Tm and the signal measured at the temperature that is higher than the unique, predetermined Tm indicates that the labeled duplex nucleic acid is the result of specific hybridization of a target-specific probe to its target. In some aspects, signal is measured at no more than n+1 different temperatures, wherein n is the number of unique target-specific probes in the reaction mixture. In some aspects, the steps are performed on multiple partitions in a dPCR reaction. In some aspects, the first and second signals are normalized relative to the third signal by subtracting the third signal from the first and second signals. In further aspects, the change between the first and second signals exceeds a predetermined threshold.

In some embodiments, the present disclosure provides a method for determining the presence of at least one target nucleic acid sequence in a sample, the method comprising: a) contacting, under hybridization conditions, the sample with at least one cleavable, target-specific probe capable of specifically hybridizing to the target nucleic acid sequence if present in a reaction mixture; b) cleaving the probe that is specifically hybridized to the target nucleic acid sequence to form a truncated probe; c) providing conditions to cause the truncated probe to hybridize to a capture sequence; d) extending the truncated probe to form a duplex nucleic acid having a predetermined Tm and a signal-generating label; e) (performing a melt analysis by) measuring a first signal at a temperature below the predetermined Tm and a second signal at a temperature above the predetermined Tm without measuring a signal at the predetermined Tm; and f) determining the presence of the target nucleic acid sequence by detecting a change in the first and second signals. In some aspects, the sample is contacted with at least two different cleavable probes, each different cleavable probe being specific for a different target nucleic acid sequence, wherein, in the presence of its specific target nucleic acid sequence, each different cleavable probe forms a duplex nucleic acid having a unique, predetermined Tm, and wherein the duplex nucleic acids having unique, predetermined Tms all have the same signal-generating label, further comprising the steps of, for each duplex nucleic acid having a unique, predetermined Tm, measuring a first signal at a temperature below the predetermined Tm and a second signal at a temperature above the predetermined Tm and determining the presence of the target nucleic acid sequence by detecting a change between the first and second signals. In some aspects, signal is measured at no more than n+1 different temperatures, wherein n is the number of different cleavable probes in the reaction mixture. In some aspects, the unique, predetermined Tms of said different duplex nucleic acids are at least 2 degrees Celsius different. In some aspects, the unique, predetermined Tms of said different duplex nucleic acids are at least 5 degrees Celsius different. In some aspects, the unique, predetermined Tms of said different duplex nucleic acids are at least 10 degrees Celsius different. In some aspects, the capture sequence and truncated probe are unimolecular. In other aspects, the capture sequence and truncated probe are bimolecular. In some aspects, the target nucleic acid is determined to be present when the ratio between the first signal and the second signal exceeds a predetermined threshold. In some aspects, the method is performed without measuring a signal at a temperature within 2 degrees Celsius of the predetermined Tm. In some aspects, the method is performed without measuring a signal at a temperature within 5 degrees Celsius of the predetermined Tm. In some aspects, the at least one cleavable probe is labeled with a first member of a reporter-quencher pair and the at least one cleavable probe adopts a first conformation when hybridized to its target nucleic acid sequence.

In some aspects, specific hybridization of the at least one cleavable probe to its target sequence results in cleavage of the probe at a cleavage site, release of the truncated probe from the target nucleic acid sequence to adopt a second conformation, and strand extension from the cleavage site. In some aspects, strand extension includes incorporating a second member of a reporter-quencher pair that interacts with the first member of the reporter-quencher pair (resulting in a change in signal). In some aspects, the first conformation is a linear conformation and the second conformation is a hairpin conformation. In some aspects, the method further comprises the step of measuring a third signal at a third temperature at which all nucleic acids in the reaction mixture are denatured, and normalizing the first and second signals relative to the third signal. In some aspects, the steps are performed on multiple partitions in a dPCR reaction. In some aspects, the melt analysis is performed across multiple partitions in a dPCR reaction, further comprising prior to cleaving, measuring a signal from the label of the cleavable probe in the multiple partitions and setting a threshold using the signal measured prior to cleaving to distinguish partitions containing the target nucleic acid from partitions not containing the target nucleic acid. In some aspects, the melt analysis is performed across multiple partitions in a dPCR reaction, further comprising after extending and prior to melt analysis, measuring multiple signals at a range of temperatures and using the measured signals to correct for light and temperature-dependent changes in signals measured during melt analysis.

In some embodiments, the present disclosure provides a method of performing a melt analysis of a labeled duplex nucleic acid in a reaction mixture, the method comprising: a) measuring a first signal from the labeled duplex nucleic acid at a first temperature at which the labeled duplex nucleic acid is predominantly in a first conformation; (b) measuring a second signal from the labeled duplex nucleic acid at a second temperature at which the labeled duplex nucleic acid is predominantly in a second conformation, wherein signal is not measured at a temperature intermediate the first and second temperatures and at which about half the duplex nucleic acid is in the first conformation and half the duplex nucleic acid is in the second conformation; and (c) determining if the labeled duplex nucleic acid is the result of specific hybridization of a target-specific probe to a target sequence by comparing the first signal and the second signal, wherein a change between the first signal and the second signal indicates that the labeled duplex nucleic acid is the result of specific hybridization of a target-specific probe to a target sequence. In a further aspects, a method comprises performing a melt analysis of a labeled duplex nucleic acid in a reaction mixture, the method comprising (a) measuring a first signal from the labeled duplex nucleic acid at a first temperature at which the labeled duplex nucleic acid is in a first conformation; (b) measuring a second signal from the labeled duplex nucleic acid at a second temperature at which the labeled duplex nucleic acid is in a second conformation, wherein signal is not measured at a temperature intermediate the first and second temperatures; and (c) determining if the labeled duplex nucleic acid is the result of specific hybridization of a target-specific probe to a target sequence by comparing the first signal and the second signal, wherein a change between the first signal and the second signal indicates that the labeled duplex nucleic acid is the result of specific hybridization of a target-specific probe to a target sequence. In some aspects, the reaction mixture contains at least two different labeled duplex nucleic acids, each different labeled duplex nucleic acid being capable of adopting the second conformation at a unique temperature, and each different labeled nucleic acid having the same signal-generating label, further comprising the steps of, for each labeled duplex nucleic acid, measuring a first signal at a temperature at which the labeled duplex nucleic acid is predominantly in a first conformation and measuring a second signal at a temperature at which the labeled duplex nucleic acid is predominantly in a second conformation and comparing the first and second signals. In some aspects, signal is measured at no more than n+1 different temperatures, wherein n is the number of different duplex nucleic acids in the reaction mixture. In some aspects, the first conformation is a hairpin conformation and the second conformation is a linear conformation. In some aspects, the target-specific probe is a cleavable probe labeled with a first member of a reporter-quencher pair. In some aspects, specific hybridization of the target-specific probe to its target sequence results in cleavage of the probe at a cleavage site to form a truncated probe, release of the truncated probe from the target nucleic acid sequence, to form a hairpin probe, and strand extension from the cleavage site. In some aspects, strand extension includes incorporating a second member of a reporter-quencher pair that interacts with the first member of the reporter-quencher pair, resulting in a change in signal. In some aspects, the method further comprises the step of measuring a third signal at a third temperature at which all nucleic acids in the reaction mixture are denatured, and normalizing the first and second signals relative to the third signal. In some aspects, the steps are performed on multiple partitions in a dPCR reaction.

In some embodiments, the present disclosure provides a method for detecting the presence of at least one target nucleic acid sequence in a sample, the method comprising: a) contacting the sample with at least one cleavable probe capable of specifically hybridizing to the target nucleic acid sequence if present, the cleavable probe comprising a first non-natural nucleotide labeled with a first member of a reporter-quencher pair; b) cleaving the probe that is specifically hybridized to the target nucleic acid sequence to form a truncated probe; c) providing conditions to cause the truncated probe to form a hairpin probe; d) extending the hairpin probe in the presence of a second non-natural nucleotide labeled with a second member of the reporter-quencher pair, the second non-natural nucleotide being capable of base-pairing with the first non-natural nucleotide to form a hairpin probe having a predetermined Tm; e) (performing a melt analysis by) measuring a first signal from the reporter-quencher pair at a temperature below the predetermined Tm and a second signal at a temperature above the predetermined Tm without measuring a signal at the predetermined Tm; and f) determining the presence of the target nucleic acid sequence by detecting a change in the first and second signals. In some aspects, the sample is contacted with two or more different cleavable probes, each specific for a different nucleic acid and each capable of forming, in the presence of its respective target nucleic acid, a hairpin probe having a unique predetermined Tm, and wherein each different hairpin probe includes the same reporter-quencher pair, further comprising the step of, for each different hairpin probe, measuring a first signal at a temperature below the predetermined Tm and a second signal at a temperature above the predetermined Tm of the hairpin probe, and comparing the first and second signals for each different hairpin probe. In some aspects, the sample is contacted with two or more different cleavable probes in a single reaction compartment. In some aspects, signal is measured at no more than n+1 different temperatures, wherein n is the number of different cleavable probes in the reaction compartment. In some aspects, the unique, predetermined Tms of said different hairpin probes are at least 2 degrees Celsius different. In some aspects, the unique, predetermined Tms of said different hairpin probes are at least 5 degrees Celsius different. In some aspects, the unique, predetermined Tms of said different hairpin probes are at least 10 degrees Celsius different. In some aspects, the target nucleic acid is determined to be present when the ratio between the first signal and the second signal exceeds a predetermined threshold. In some aspects, melt analysis is performed without measuring a signal at a temperature within 2 degrees Celsius of the predetermined Tm. In some aspects, melt analysis is performed without measuring a signal at a temperature within 5 degrees Celsius of the predetermined Tm. In some aspects, the method further comprises the step of measuring a third signal at a third temperature at which all nucleic acids in the reaction mixture are denatured, and normalizing the first and second signals relative to the third signal. In some aspects, the steps are performed on multiple partitions in a dPCR reaction. In some aspects, the melt analysis is performed across multiple partitions in a dPCR reaction, further comprising prior to cleaving, measuring a signal from the label of the cleavable probe in the multiple partitions and setting a threshold using the signal measured prior to cleaving to distinguish partitions containing the target nucleic acid from partitions not containing the target nucleic acid. In some aspects, the melt analysis is performed across multiple partitions in a dPCR reaction, further comprising after extending and prior to melt analysis, measuring multiple signals at a range of temperatures and using the measured signals to correct for light and temperature-dependent changes in signals measured during melt analysis.

In some embodiments, the present disclosure provides a method for detecting the presence or absence of at least one target nucleic acid sequence in a sample, the method comprising: a) contacting the sample with at least one cleavable probe capable of specifically hybridizing to the target nucleic acid sequence if present, the cleavable probe including a signal-generating label; b) cleaving the probe that is specifically hybridized to the target nucleic acid sequence to form a truncated probe; c) providing conditions to cause the truncated probe to hybridize to a capture sequence that includes a sequence that is complementary to the truncated probe; d) extending the truncated probe using the capture sequence as a template, to form a double stranded probe having a predetermined Tm; and e) (performing a melt analysis by) measuring a first signal from the signal-generating label at a first temperature below the predetermined Tm and a second signal at a second temperature above the predetermined Tm, without measuring a signal at the predetermined Tm; and f) determining the presence of the target nucleic acid sequence by detecting a change in signal measured at the first temperature and the second temperature. In some aspects, the sample is contacted with two or more different cleavable probes, each specific for a different target nucleic acid and each capable of forming, in the presence of its respective target nucleic acid, a double stranded probe having a unique predetermined Tm, and wherein each different double stranded probe includes the same reporter-quencher pair, further comprising for each different double stranded probe, the step of measuring a first signal from at a first temperature below the predetermined Tm and a second signal at a second temperature above the predetermined Tm, and comparing the first and second signals measured for each different double stranded probe. In some aspects, the capture sequence and truncated probe are unimolecular. In other aspects, the capture sequence and truncated probe are bimolecular. In some aspects, the sample is contacted with two or more different cleavable probes in a single reaction compartment. In some aspects, signal is measured at no more than n+1 different temperatures, wherein n is the number of different cleavable probes in the reaction compartment. In some aspects, the unique, predetermined Tms of said different double stranded probes are at least 2 degrees Celsius different. In some aspects, the unique, predetermined Tms of said different double stranded probes are at least 5 degrees Celsius different. In some aspects, the unique, predetermined Tms of said different double stranded probes are at least 8 degrees Celsius different. In some aspects, the target nucleic acid is determined to be present when the ratio between the first signal and the second signal exceeds a predetermined threshold. In some aspects, the method is performed without measuring a signal at a temperature within 2 degrees Celsius of the predetermined Tm. In some aspects, the method is performed without measuring a signal at a temperature within 5 degrees Celsius of the predetermined Tm. In further aspects, the signal-generating label is a first member of a reporter-quencher pair and the double stranded probe includes a second member of the reporter-quencher pair that interacts with the first member of the reporter-quencher pair. In some aspects, wherein the cleavable probe comprises a first non-natural nucleotide to which the signal generating label is attached, the duplex nucleic acid comprises a second non-natural nucleotide that hybridizes to the first non-natural nucleotide, and the second member of the reporter-quencher pair is attached to the second non-natural nucleotide. In certain aspects, the first member of the reporter-quencher pair is a fluorescent entity and the second member of the reporter-quencher pair is a quencher that quenches the fluorescence of the fluorescent entity. In yet further aspects, the first and second non-natural nucleotides are one of iso-C and iso-G. In some aspects, the method further comprises the step of measuring a third signal at a third temperature at which all nucleic acids in the reaction mixture are denatured, and normalizing the first and second signals relative to the third signal. In some aspects, the steps are performed on multiple partitions in a dPCR reaction. In some aspects, the melt analysis is performed across multiple partitions in a dPCR reaction, further comprising prior to cleaving, measuring a signal from the label of the cleavable probe in the multiple partitions and setting a threshold using the signal measured prior to cleaving to distinguish partitions containing the target nucleic acid from partitions not containing the target nucleic acid. In some aspects, the melt analysis is performed across multiple partitions in a dPCR reaction, further comprising after extending and prior to melt analysis, measuring multiple signals at a range of temperatures and using the measured signals to correct for light and temperature-dependent changes in signals measured during melt analysis.

In some embodiments, the present disclosure provides a method of performing a melt analysis on a plurality of labeled nucleic acid duplexes, the method comprising: (a) providing at least a first, a second, and a third labeled duplex nucleic acid, wherein each of the first, second, and third labeled duplex nucleic acids has a unique predetermined Tm, and the unique predetermined Tm of the second labeled duplex nucleic acid is higher than the unique, predetermined Tm of the first labeled duplex nucleic acid, and the unique, predetermined Tm of the third labeled duplex nucleic acid is higher than the unique, predetermined Tm of the second labeled duplex nucleic acid, and wherein the first, second, and third labeled duplex nucleic acids are labeled with the same label; (b) detecting a first signal from the first, second, and third labeled duplex nucleic acids at a first temperature that is lower than the unique, predetermined Tm of the first labeled duplex nucleic acid; (c) detecting a second signal from the first, second, and third labeled duplex nucleic acids at a second temperature that is between the unique, predetermined Tm of the first labeled duplex nucleic acid and the unique, predetermined Tm of the second labeled duplex nucleic acid; (d) detecting a third signal from the first, second, and third labeled duplex nucleic acids at a third temperature that is between the unique, predetermined Tm of the second labeled duplex nucleic acid and the unique, predetermined Tm of the third labeled duplex nucleic acid; (e) detecting a fourth signal from the first, second, and third labeled duplex nucleic acids at a fourth temperature that is above the unique, predetermined Tm of the third labeled duplex nucleic acid; and (f) determining if one or more of the first, second, and third labeled duplex nucleic acids is the result of cleavage of a target-specific probe by comparing the first, second, third, and fourth signals, wherein a change between the first signal and the second signal indicates that the first labeled duplex nucleic acid is the result of cleavage of a first target-specific probe, a change between the second signal and the third signal indicates that the second labeled duplex nucleic acid is the result of cleavage of a second target-specific probe, and a change between the third signal and the fourth signal indicates that the third labeled duplex nucleic acid is the result of cleavage of a third target-specific probe. In some aspects, signal is not detected at the unique, predetermined Tms of the first, second, and third labeled duplex nucleic acids. In some aspects, the difference between the first temperature and the second temperature is greater than two degrees Celsius, the difference between the second temperature and the third temperature is greater than two degrees Celsius, and the difference between the third temperature and the fourth temperature is greater than two degrees Celsius. In some aspects, the steps are performed on multiple partitions in a dPCR reaction. In some aspects, the first and second signals are normalized relative to the third signal by subtracting the third signal from the first and second signals. In further aspects, a method comprises the step of measuring a third signal at a third temperature at which all duplex nucleic acids in the reaction mixture are denatured, and normalizing the first and second signals relative to the third signal.

In still a further embodiment a method is provided for determining the presence of a target nucleic acid in a sample, the method comprising the steps of: (a) providing a reaction mixture comprising the sample and a signal generating target-specific probe, wherein the target-specific probe generates a first signal when in a first, single-stranded conformation; (b) measuring the first signal from the target-specific probe in the reaction mixture; (c) providing conditions for the target-specific probe to hybridize to the target nucleic acid if present, and adopt a second conformation, the second conformation being a duplex nucleic acid having a predetermined Tm and being capable of generating a second signal at a temperature lower than the predetermined Tm; (d) measuring the second signal from the duplex nucleic acid at a temperature lower than the predetermined Tm without measuring a signal at the predetermined Tm; and (e) determining the presence of the target nucleic acid when there is a difference between the first signal and the second signal. In certain aspects, the target specific probe is a cleavable probe that is cleaved upon hybridization to the target nucleic acid to form a truncated probe and/or the truncated probe binds to a capture sequence and is extended to form the duplex nucleic acid. In some aspects, the first and second signals are fluorescent signals. In certain aspects, the first signal is detected prior to hybridization of the target-specific probe to the target nucleic acid. In some aspects, the first signal is detected after cleavage and extension under conditions at which the target-specific probe is in the first conformation. In further aspects, the cleavable probe comprises a first non-natural nucleotide labeled with a first member of a reporter-quencher pair, and the duplex nucleic acid comprises a second non-natural nucleotide capable of base-pairing with the first non-natural nucleotide and labeled with a second member of the reporter-quencher pair. For example, in some cases, the first and second non-natural nucleotides are one of iso-C and iso-G. In some cases, the target-specific probe is labeled with a fluorophore prior to binding to the capture sequence, and wherein a quencher is incorporated into the duplex nucleic acid at a position that results in quenching of the fluorophore. In some cases, the reaction mixture is subjected to conditions for amplification of the target nucleic acid after step (b). In certain aspects, the capture sequence and truncated probe are unimolecular and hybridize to form a hairpin probe. In some cases, the capture sequence and truncated probe are bi-molecular.

In still a further embodiment, method for detecting the presence of a target nucleic acid in a sample is provided, the method comprising the steps of: (a) providing a reaction mixture comprising the sample, at least one labeled, cleavable target-specific probe capable of specifically hybridizing to the target nucleic acid sequence if present in the reaction mixture, and the label being a first member of a reporter-quencher pair; (b) measuring a first signal from the labeled target-specific probe in the reaction mixture; (c) providing conditions to cause the labeled cleavable target-specific probe to hybridize to the target nucleic acid sequence if present in the reaction mixture; (d) cleaving the probe that is specifically hybridized to the target nucleic acid sequence to form a truncated probe; (e) providing conditions to cause the truncated probe to hybridize to a capture sequence; (f) extending the truncated probe to form a duplex nucleic acid having a second member of the reporter-quencher pair and a predetermined Tm; (g) measuring a second signal at a temperature below the predetermined Tm; and (h) detecting the presence of the target nucleic acid when there is a difference between the first and second signals that exceeds a predetermined threshold. In some aspects, the capture sequence and truncated probe are unimolecular and hybridize to form a hairpin probe. In certain cases, the capture sequence and truncated probe are bi-molecular. In certain aspects, wherein the target specific probe comprises a first non-natural nucleotide to which the first member of the reporter-quencher pair is attached and the duplex nucleic acid comprises a second non-natural nucleotide to which the second member of the reporter-quencher pair is attached, and the first and second non-natural nucleotides are capable of base-pairing with each other. For example, in some cases, the first and second non-natural nucleotides are one or the other of isoC and isoG. In certain aspects, the first member of the reporter-quencher pair is a fluorophore and the second member of the reporter-quencher pair is a quencher.

In yet a further embodiment, a method for determining the presence of a target nucleic acid in a sample is provided, the method comprising the steps of: (a) providing a reaction mixture comprising the sample and a signal generating target-specific probe, wherein the target-specific probe generates a first signal when in a first, single-stranded conformation; (b) measuring the first signal from the target-specific probe in the reaction mixture; (c) subjecting the reaction mixture to conditions for amplification of the target nucleic acid, wherein during amplification, the target-specific probe is modified to form a modified target-specific probe comprising a duplex nucleic acid having a predetermined Tm and being capable of generating a second signal at a temperature lower than the predetermined Tm; (d) measuring the second signal at a temperature lower than the predetermined Tm without measuring a signal at the predetermined Tm; and (e) determining the presence of the target nucleic acid when there is a difference between the first signal and the second signal that exceeds a predetermined threshold. In some aspects, the target specific probe is modified by being cleaved upon hybridization to the target nucleic acid to form a truncated probe which binds to a capture sequence and is extended to form the duplex nucleic acid. In certain aspects, the first and second signals are fluorescent signals. In some cases, the first signal is detected prior to hybridization of the target-specific probe to the target nucleic acid. In certain aspects, the first signal is detected after cleavage and extension under conditions at which the modified target-specific probe is in a single stranded conformation. In certain aspects, the target-specific probe comprises a first non-natural nucleotide labeled with a first member of a reporter-quencher pair, and the modified target-specific probe comprises a second non-natural nucleotide capable of base-pairing with the first non-natural nucleotide and labeled with a second member of the reporter-quencher pair. For example, in some cases, the first and second non-natural nucleotides are one of iso-C and iso-G. In certain aspects, the target-specific probe is labeled with a fluorophore prior to binding to the capture sequence, and wherein a quencher is incorporated into the duplex nucleic acid during extension at a position that results in quenching of the fluorophore.

In a further embodiment there is provided a method of detecting the presence of a first and second target nucleic acid in a sample, the method comprising the steps of: (a) forming an amplification reaction mixture comprising a first and second fluorescent signal-generating target-specific probe and the sample potentially containing the first and second target nucleic acid; (b) partitioning the reaction mixture so that each partition contains, on average, zero or one of the first and/or second target nucleic acids; (c) acquiring a first, second and third set of fluorescent intensity values from images of at least a subset of partitions at preselected temperatures T1, T2 and T3 and for each partition in the subset of partitions, determining a first fluorescent intensity value at the preselected temperature T1, a second fluorescent intensity value at the preselected temperature T2 and a third fluorescent intensity value at the preselected temperature T3; (d) subjecting the partitions containing the amplification reaction mixture to conditions for amplification of the first and second target nucleic acids and modification of the first signal generating probe in the presence of its target nucleic acid to form a first duplex nucleic acid having a first predetermined Tm, and modification of the second signal generating probe in the presence of its target nucleic acid to form a second duplex nucleic acid having a second predetermined Tm; (e) acquiring a fourth set of fluorescent intensity values from images of the subset of partitions at the temperature T1 which is lower than the first predetermined Tm and calculating a fourth intensity value for each partition; (f) acquiring a fifth set of fluorescent intensity values from images of the subset of partitions at the temperature T2 that is higher than the first predetermined Tm but lower than the second predetermined Tm, and calculating a fifth intensity value for each partition; (g) acquiring a sixth set of fluorescent intensity values from images of the subset of partitions at the temperature T3 that is higher than the second predetermined Tm and calculating a sixth intensity value for each partition; (h) for each partition, dividing the fourth intensity value by the first intensity value to obtain a seventh intensity value associated with T1; (i) for each partition, dividing the fifth intensity value by the second intensity value to obtain a eighth intensity value associated with T2; (j) for each partition, dividing the sixth intensity value by the third intensity value to obtain a ninth intensity value associated with T3; (k) for each partition, detecting a change between the eighth intensity value and the seventh intensity value to determine the presence of the first target nucleic; and (1) for each partition, detecting a change between the ninth average intensity value and the eighth average intensity value to determine the presence of second target nucleic acid. In some cases, the first and second fluorescent signal-generating probes have the same signal-generating label. In certain aspects, the signal generating label is a first member of a reporter-quencher pair and the first and second duplex nucleic acids comprise a second member of the reporter-quencher pair. In certain aspects, the first and second signal-generating probes comprise a first non-natural nucleotide to which the first member of the reporter-quencher pair is attached, and the first and second duplex nucleic acids comprise a second non-natural nucleotide to which the second member of the reporter-quencher pair is attached, and the first and second non-natural nucleotides are capable of base-pairing with each other. For example, in some aspects, the non-natural nucleotides are one of iso-C or iso-G. In certain cases, the first and second signal-generating probes are cleavable probes that are cleaved during amplification. In further aspects, the change between the eighth intensity value and the seventh intensity value exceeds a predetermined threshold, and wherein the change between the ninth intensity value and the eighth intensity value exceeds a predetermined threshold In still a further embodiment there is provided a method of detecting the presence of a target nucleic acid in a sample, the method comprising the steps of: (a) forming an amplification reaction mixture comprising a fluorescent signal-generating target-specific probe and the sample containing the target nucleic acid; (b) partitioning the reaction mixture so that each partition contains, on average, zero or one of the target nucleic acid; (c) acquiring a first and second set of fluorescent intensity values from images of at least a subset of partitions at preselected temperatures T1 and T2, and for each partition in the subset of partitions, determining a first fluorescent intensity value at the preselected temperature T1 and a second fluorescent intensity value at the preselected temperature T2; (d) subjecting the partitions containing the amplification reaction mixture to conditions for amplification of the target nucleic acids and modification of the signal generating probe in the presence of its target nucleic acid to form a duplex nucleic acid having a predetermined Tm; (e) acquiring a third set of fluorescent intensity values from images of the subset of partitions at the temperature T1 which is lower than the predetermined Tm and calculating a third intensity value for each partition; (f) acquiring a fourth set of fluorescent intensity values from images of the subset of partitions at the temperature T2 that is higher than the predetermined Tm, and calculating a fourth intensity value for each partition; (g) for each partition, dividing the third intensity value by the first intensity value to obtain a fifth intensity value associated with T1; (h) for each partition, dividing the fourth intensity value by the second intensity value to obtain a sixth intensity value associated with T2; (i) for each partition, detecting a change between the sixth intensity value and the fifth intensity value to determine the presence of the target nucleic acid. In a further aspects, the target nucleic acid is a first target nucleic acid, the signal generating target-specific probe is a first fluorescent signal-generating target-specific probe and the predetermined Tm is a first predetermined Tm, further comprising detecting the presence of a second target nucleic acid, wherein the reaction mixture further comprises a second fluorescent signal-generating target-specific probe, the method further comprising the steps of: (j) in step (b), partitioning the reaction mixture so that each partition contains, on average, zero or one of the first and/or second target nucleic acid; (k) in step (c), acquiring a fifth set of fluorescent intensity values from images of at least a subset of partitions at a preselected temperature T3, and for each partition in the subset of partitions, determining a seventh fluorescent intensity value at the preselected temperature T3; (1) in step (d) subjecting the partitions containing the amplification reaction mixture to conditions for amplification of the target nucleic acids and modification of the second signal generating probe in the presence of its target nucleic acids to form a second duplex nucleic acid having a second predetermined Tm; (m) acquiring a sixth set of fluorescent intensity values from images of the subset of partitions at the temperature T3 that is higher than the second predetermined Tm and calculating an eighth intensity value for each partition; (n) for each partition, dividing the eighth intensity value by the seventh intensity value to obtain a ninth intensity value associated with T3; (o) for each partition, detecting a change between the ninth intensity value with the sixth intensity value to determine the presence of the second target nucleic acid. In some aspects, the change between the sixth and fifth intensity values and the change between the ninth and the sixth intensity values exceeds a predetermined threshold. In certain cases, the first and second fluorescent signal-generating probes have the same signal-generating label. In further aspects, the signal generating label is a first member of a reporter-quencher pair and the first and second duplex nucleic acids comprise a second member of the reporter-quencher pair. In some cases, the first and second signal-generating probes comprise a first non-natural nucleotide to which the first member of the reporter-quencher pair is attached, and the first and second duplex nucleic acids comprise a second non-natural nucleotide to which the second member of the reporter-quencher pair is attached, and the first and second non-natural nucleotides are capable of base-pairing with each other. For example, in some aspects, the non-natural nucleotides are one of iso-C or iso-G. In some aspects, the first and second signal-generating probes are cleavable probes that are cleaved during amplification.

In some further aspects, any of the foregoing methods can be performed wherein the steps are performed across multiple partitions in a dPCR reaction, further comprising prior to determining the presence of the target nucleic acid, identifying partitions in which there is no change between the first and second signals as target-negative partitions, and using measured signals from target-negative partitions to normalize for light and temperature-dependent changes in first and second signals measured in each partition.

As used herein, "essentially free," in terms of a specified component, is used to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2: Example of melt analysis plots showing RFU versus Temperature (A, B) and negative derivative of RFU with respect to temperature (C, D) for a sample containing a target for a single target-specific probe (A, C) and a sample containing targets for 3 target-specific probes shown in FIG. 1 (B, D) using the method of the invention. Fluorescence images were acquired only at the temperatures denoted by X.

FIG. 3: Example of random distribution of targets for 3 target-specific probes shown in FIG. 1 in 36 partitions for dPCR applications. Each partition contains 0, 1, 2 or 3 targets.

FIG. 4: Fluorescence image of the system shown in FIG. 3 taken at T1 (60° C. in this example), with relative brightness indicating the number of uncleaved, unextended and unique probes in the partitions. In this example using cleavable probes, all target-negative partitions are bright due to fluorescence of uncleaved, unextended probes, and all target-containing partitions are relatively darker depending on the number of targets in each partition.

FIG. 5: Fluorescence image of the system shown in FIG. 3 taken at T2 (70° C.), at which partitions containing target A show increased fluorescence as a result of target-A probes having denatured resulting in separation of fluor and quencher.

FIG. 6: Example of image comparison for the system shown in FIG. 3. Average fluorescence intensity calculated for each partition at T2 is divided by the average fluorescence intensity calculated for each partition at T1 to determine which partitions show a change in fluorescence intensity (FIG. 6A).

FIG. 8: Example of using image normalization to account for partition-specific, system-induced variations. FIGS. 8E and 8F show the corresponding 1D amplitude plots.

FIG. 12: Singleplex Discrete Melt Analysis. A: Fluorescence v. temperature plot for partitions of the sample shown in FIG. 11 measured at temperatures T1 and T2; B: 1D amplitude plot of fluorescence intensity per partition at T2/T1; C: Fluorescence v. temperature plot of the data from C after normalization to correct for system variability. Target concentration is determined by calculating the average number of copies per partition.

DESCRIPTION OF ILLUSTRATIVE EMBODIMENTS

I. The Present Embodiments

Figure 1A:
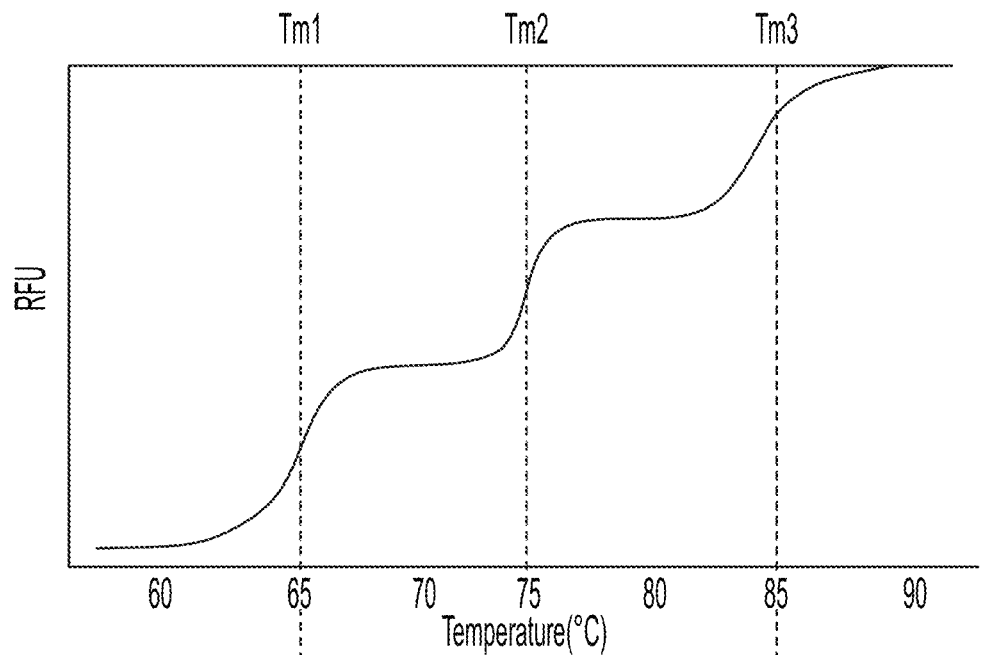
FIG. 1: Exemplary plot of continuous melt analysis showing Relative Fluorescent Units (RFU) versus Temperature (A) and the negative derivative of RFU with respect to temperature (B) for a sample containing targets for 3 target-specific probes having melt temperatures of 65, 75, and 85° C., respectively. For continuous melt analysis, RFU measurements are taken with every 0.5-1.0 temperature change.

The present disclosure provides methods for performing rapid melt analysis to determine the presence or absence of targets within a sample, even when amplified targets have similar melt peaks. In a preferred embodiment, melt analysis is performed at discrete melt temperatures below the Tm of a target-specific probe and above the Tm of a target-specific probe, but not at the Tm of the target-specific probe.

II. Definitions

As used herein "nucleic acid" means either DNA or RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, and unusual base-pairing combinations, such as the isobases. Accordingly, the nucleic acids described herein include not only the standard bases adenine (A), cytosine (C), guanine (G), thymine (T), and uracil (U) but also non-standard or non-natural nucleotides. Non-standard or non-natural nucleotides, which form hydrogen-bonding base pairs, are described, for example, in U.S. Pat. Nos. 5,432,272, 5,965,364, 6,001,983, 6,037,120, and 6,140,496, all of which are incorporated herein by reference. By "non-standard nucleotide" or "non-natural nucleotide" it is meant a base other than A, G, C, T, or U that is susceptible to incorporation into an oligonucleotide and that is capable of base-pairing by hydrogen bonding, or by hydrophobic, entropic, or van der Waals interactions, with a complementary non-standard or non-natural nucleotide to form a base pair. Some examples include the base pair combinations of iso-C/iso-G, K/X, K/P, H/J, and M/N, as illustrated in U.S. Pat. No. 6,037,120, incorporated herein by reference.

The hydrogen bonding of these non-standard or non-natural nucleotide pairs is similar to those of the natural bases where two or three hydrogen bonds are formed between hydrogen bond acceptors and hydrogen bond donors of the pairing non-standard or non-natural nucleotides. One of the differences between the natural bases and these non-standard or non-natural nucleotides is the number and position of hydrogen bond acceptors and hydrogen bond donors. For example, cytosine can be considered a donor/acceptor/acceptor base with guanine being the complementary acceptor/donor/donor base. Iso-C is an acceptor/acceptor/donor base and iso-G is the complementary donor/donor/acceptor base, as illustrated in U.S. Pat. No. 6,037,120, incorporated herein by reference.

Other non-natural nucleotides for use in oligonucleotides include, for example, naphthalene, phenanthrene, and pyrene derivatives as discussed, for example, in Ren, et al., 1996 and McMinn et al., 1999, both of which are incorporated herein by reference. These bases do not utilize hydrogen bonding for stabilization, but instead rely on hydrophobic or van der Waals interactions to form base pairs.

As used herein, the term "sample" is used in its broadest sense. A sample may include a bodily tissue or a bodily fluid including but not limited to blood (or a fraction of blood, such as plasma or serum), lymph, mucus, tears, urine, and saliva. A sample may include an extract from a cell, a chromosome, organelle, or a virus. A sample may comprise DNA (e.g., genomic DNA), RNA (e.g., mRNA), and/or cDNA, any of which may be amplified to provide an amplified nucleic acid. A sample may include nucleic acid in solution or bound to a substrate (e.g., as part of a microarray). A sample may comprise material obtained from an environmental locus (e.g., a body of water, soil, and the like) or material obtained from a fomite (i.e., an inanimate object that serves to transfer pathogens from one host to another).

The term "source of nucleic acid" refers to any sample that contains nucleic acids (RNA or DNA). Particularly preferred sources of target nucleic acids are biological samples including, but not limited to, blood, plasma, serum, saliva, cerebral spinal fluid, pleural fluid, milk, lymph, sputum, and semen.

As used herein, the term "limit of detection" refers to the lowest level or amount of an analyte, such as a nucleic acid, that can be detected and quantified. Limits of detection can be represented as molar values (e.g., 2.0 nM limit of detection), as gram measured values (e.g., 2.0 microgram limit of detection under, for example, specified reaction conditions), copy number (e.g., $1 \times 10^5$ copy number limit of detection), or other representations known in the art.

As used herein the term "isolated" in reference to a nucleic acid molecule refers to a nucleic acid molecule that is separated from the organisms and biological materials (e.g., blood, cells, serum, plasma, saliva, urine, stool, sputum, nasopharyngeal aspirates and so forth) that are present in the natural source of the nucleic acid molecule. An isolated nucleic acid molecule, such as a cDNA molecule, can be substantially free of other cellular material or culture medium when produced by recombinant techniques, or substantially free of chemical precursors or other chemicals when chemically synthesized. In some embodiments, nucleic acid molecules encoding polypeptides/proteins may also be isolated or purified. Methods of nucleic acid isolation are well known in the art and may include total nucleic acid isolation/purification methods, RNA-specific isolation/purification methods, or DNA-specific isolation/purification methods.

As used herein, the term "microarray" refers to an arrangement of a plurality of polynucleotides, polypeptides, or other chemical compounds on a substrate. The terms "element" and "array element" refer to a polynucleotide, polypeptide, or other chemical compound having a unique and defined position on a microarray.

As used herein, an oligonucleotide is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides, made up of "dNTPs," which do not have a hydroxyl group at the 2' position, and oligoribonucleotides, made up of "NTPs," which have a hydroxyl group in the 2' position. Oligonucleotides also may include derivatives, in which the hydrogen of the hydroxyl group is replaced with an organic group, e.g., an allyl group.

An oligonucleotide is a nucleic acid that includes at least two nucleotides. Oligonucleotides used in the methods disclosed herein typically include at least about ten (10) nucleotides and more typically at least about fifteen (15) nucleotides. Preferred oligonucleotides for the methods disclosed herein include about 10-100 nucleotides. An oligonucleotide may be designed to function as a "primer." A "primer" is a short nucleic acid, usually a ssDNA oligonucleotide, which may be annealed to a target polynucleotide by complementary base-pairing. The primer may then be extended along the target DNA or RNA template strand by a polymerase enzyme, such as a DNA polymerase enzyme. Primer pairs can be used for amplification (and identification) of a nucleic acid sequence (e.g., by the polymerase chain reaction (PCR)). An oligonucleotide may be designed to function as a "probe." A "probe" refers to an oligonucleotide, its complements, or fragments thereof, which are used to detect identical, allelic, or related nucleic acid sequences. Probes may include oligonucleotides that have been attached to a detectable label or reporter molecule. Typical labels include fluorescent dyes, quenchers, radioactive isotopes, ligands, scintillation agents, chemiluminescent agents, and enzymes. Probes may also be extended by a polymerase, using a target nucleic acid or self-complementary regions as a template.

An oligonucleotide may be designed to be specific for a target nucleic acid sequence in a sample. For example, an oligonucleotide may be designed to include "antisense" nucleic acid sequence of the target nucleic acid. As used herein, the term "antisense" refers to any composition capable of base-pairing with the "sense" (coding) strand of a nucleic acid sequence. An antisense nucleic acid sequence may be "complementary" to a target nucleic acid sequence. As used herein, "complementarity" describes the relationship between two single-stranded nucleic acid sequences that anneal by base-pairing. For example, 5'-AGT-3' pairs with its complement, 3'-TCA-5'. In some embodiments, primers or probes may be designed to include mismatches at various positions. As used herein, a "mismatch" means a nucleotide pair that does not include the standard Watson-Crick base pairs, or nucleotide pairs that do not preferentially form hydrogen bonds. The mismatch may include a natural nucleotide or a non-natural or non-standard nucleotide substituted across from a particular base or bases in a target. For example, the probe or primer sequence 5'-AGT-3' has a single mismatch with the target sequence 3'-ACA-5'. The 5' "A" of the probe or primer is mismatched with the 3' "A" of the target. Similarly, the target sequence 5'-AGA-3' has a single mismatch with the probe or primer sequence 3'-(iC)CT-5'. Here an iso-C is substituted in place of the natural "T." However, the sequence 3'-(iC)CT-5' is not mismatched with the sequence 5'-(iG)GA-3'.

Oligonucleotides may also be designed as degenerate oligonucleotides. As used herein, "degenerate oligonucleotide" is meant to include a population, pool, or plurality of oligonucleotides comprising a mixture of different sequences where the sequence differences occur at a specified position in each oligonucleotide of the population. Various substitutions may include any natural or non-natural nucleotide, and may include any number of different possible nucleotides at any given position. For example, the above degenerate oligonucleotide may instead include R=iC or iG, or R=A or G or T or C or iC or iG.

Oligonucleotides, as described herein, typically are capable of forming hydrogen bonds with oligonucleotides having a complementary base sequence. These bases may include the natural bases, such as A, G, C, T, and U, as well as artificial, non-standard or non-natural nucleotides such as iso-cytosine and iso-guanine. As described herein, a first sequence of an oligonucleotide is described as being 100% complementary with a second sequence of an oligonucleotide when the consecutive bases of the first sequence (read 5'-to-3') follow the Watson-Crick rule of base pairing as compared to the consecutive bases of the second sequence (read 3'-to-5'). An oligonucleotide may include nucleotide substitutions. For example, an artificial base may be used in place of a natural base such that the artificial base exhibits a specific interaction that is similar to the natural base.

An oligonucleotide that is specific for a target nucleic acid also may be specific for a nucleic acid sequence that has "homology" to the target nucleic acid sequence. As used herein, "homology" refers to sequence similarity or, interchangeably, sequence identity, between two or more polynucleotide sequences or two or more polypeptide sequences. The terms "percent identity" and "% identity" as applied to polynucleotide sequences, refer to the percentage of residue matches between at least two polynucleotide sequences aligned using a standardized algorithm (e.g., BLAST).

An oligonucleotide that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm, for example, nearest-neighbor parameters, and conditions for nucleic acid hybridization are known in the art.

As used herein, "target" or "target nucleic acid" refers to a nucleic acid molecule containing a sequence that has at least partial complementarity with an oligonucleotide, for example, a probe or a primer. A "target" sequence may include a part of a gene or genome.

As used herein, "nucleic acid," "nucleotide sequence," or "nucleic acid sequence" refer to a nucleotide, oligonucleotide, polynucleotide, or any fragment thereof and to naturally occurring or synthetic molecules. These terms also refer to DNA or RNA of genomic or synthetic origin, which may be single-stranded or double-stranded and may represent the sense or the antisense strand, or to any DNA-like or RNA-like material. An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose. RNA may be used in the methods described herein and/or may be converted to cDNA by reverse transcription for use in the methods described herein.

As used herein, "amplification" or "amplifying" refers to the production of additional copies of a nucleic acid sequence. Amplification may be carried out using polymerase chain reaction (PCR) or other amplification technologies known in the art. The term "amplification reaction system" refers to any in vitro means for producing at least a first complimentary copy of a target sequence of nucleic acid. In some aspects, amplification produces multiple copies of a target sequence of nucleic acid. The term "amplification reaction mixture" refers to an aqueous solution comprising the various reagents used to amplify a target nucleic acid. These may include enzymes (e.g., a thermostable polymerase), aqueous buffers, salts, amplification primers, target nucleic acid, nucleoside triphosphates, and optionally, at least one labeled probe and/or optionally, at least one agent for determining the melting temperature of an amplified target nucleic acid (e.g., a fluorescent intercalating agent that exhibits a change in fluorescence in the presence of double-stranded nucleic acid).

Amplification of nucleic acids may include amplification of nucleic acids or subregions of these nucleic acids. For example, amplification may include amplifying portions of nucleic acids between 30 and 50, between 50 and 100, or between 100 and 300 bases long by selecting the proper primer sequences and using PCR. In further aspects, amplification can be achieved using an isothermal amplification technique (i.e., without the need for thermal cycling). For example, methods for isothermal nucleic acid amplification, such as loop mediated isothermal amplification (LAMP), are provided in U.S. Pat. No. 6,410,278, and US. Patent Publn. 20080182312, each of which is incorporated herein by reference in its entirety.

Amplification mixtures may include natural nucleotides (including A, C, G, T, and U) and non-natural or non-standard nucleotides (e.g., including iC and iG). DNA and RNA oligonucleotides include deoxyriboses or riboses, respectively, coupled by phosphodiester bonds. Each deoxyribose or ribose includes a base coupled to a sugar. The bases incorporated in naturally-occurring DNA and RNA are adenosine (A), guanosine (G), thymidine (T), cytosine (C), and uridine (U). These five bases are "natural bases." According to the rules of base pairing elaborated by Watson and Crick, the natural bases hybridize to form purine-pyrimidine base pairs, where G pairs with C and A pairs with T or U. These pairing rules facilitate specific hybridization of an oligonucleotide with a complementary oligonucleotide.

The formation of base pairs by natural bases is facilitated by the generation of two or three hydrogen bonds between the two bases of each base pair. Each of the bases includes two or three hydrogen bond donor(s) and hydrogen bond acceptor(s). The hydrogen bonds of the base pair are each formed by the interaction of at least one hydrogen bond donor on one base with a hydrogen bond acceptor on the other base. Hydrogen bond donors include, for example, heteroatoms (e.g., oxygen or nitrogen) that have at least one attached hydrogen. Hydrogen bond acceptors include, for example, heteroatoms (e.g., oxygen or nitrogen) that have a lone pair of electrons.

The natural or non-natural nucleotides used herein can be derivatized by substitution at non-hydrogen bonding sites to form modified natural or non-natural nucleotides. For example, a natural nucleotide can be derivatized for attachment to a support by coupling a reactive functional group (for example, thiol, hydrazine, alcohol, amine, and the like) to a non-hydrogen bonding atom of the nucleotide. Other possible substituents include, for example, biotin, digoxigenin, fluorescent groups, alkyl groups (e.g., methyl or ethyl), and the like.

The use of non-natural nucleotides according to the methods disclosed herein is extendable beyond the detection and quantification of nucleic acid sequences present in a sample. For example, non-natural nucleotides can be recognized by many enzymes that catalyze reactions associated with nucleic acids. While a polymerase requires a complementary nucleotide to continue polymerizing and extending an oligonucleotide chain, other enzymes do not require a complementary nucleotide. If a non-natural nucleotide is present in the template and its complementary non-natural nucleotide is not present in the reaction mix, a polymerase will typically stall (or, in some instances, misincorporate a base when given a sufficient amount of time) when attempting to extend an elongating primer past the non-natural nucleotide. However, other enzymes that catalyze reactions associated with nucleic acids, such as ligases, kinases, nucleases, polymerases, topoisomerases, helicases, and the like can catalyze reactions involving non-natural nucleotides. Such features of non-natural nucleotides can be taken advantage of, and are within the scope of the presently disclosed methods and kits.

The nucleotides disclosed herein, which may include non-natural nucleotides, may be coupled to a label (e.g., a quencher or a fluorophore). Coupling may be performed using methods known in the art.

The oligonucleotides of the present methods may function as primers. In some embodiments, the oligonucleotides are labeled. For example, the oligonucleotides may be labeled with a reporter that emits a detectable signal (e.g., a fluorophore). The oligonucleotides may include at least one non-natural nucleotide. For example, the oligonucleotides may include at least one nucleotide having a base that is not A, C, G, T, or U (e.g., iC or iG). Where the oligonucleotide is used as a primer for PCR, the amplification mixture may include at least one nucleotide that is labeled with a quencher (e.g., Dabcyl). The labeled nucleotide may include at least one non-natural or non-standard nucleotide. For example, the labeled nucleotide may include at least one nucleotide having a base that is not A, C, G, T, or U (e.g., iC or iG).

In some embodiments, the oligonucleotide may be designed not to form an intramolecular structure, such as a hairpin. In other embodiments, the oligonucleotide may be designed to form an intramolecular structure, such as a hairpin. For example, the oligonucleotide may be designed to form a hairpin structure that is altered after the oligonucleotide hybridizes to a target nucleic acid, and optionally, after the target nucleic acid is amplified using the oligonucleotide as a primer. In yet other embodiments, the oligonucleotide may be designed to be cleaved upon hybridization to a target sequence and to adopt an intramolecular structure after cleavage.

The oligonucleotide may be labeled with a fluorophore that exhibits quenching when incorporated in an amplified product as a primer. In other embodiments, the oligonucleotide may emit a detectable signal after the oligonucleotide is incorporated in an amplified product as a primer (e.g., inherently, or by fluorescence induction or fluorescence dequenching). Such primers are known in the art (e.g., LightCycler primers, Amplifluor™ primers, Scorpion™ primers, and Lux™ primers). The fluorophore used to label the oligonucleotide may emit a signal when intercalated in double-stranded nucleic acid. As such, the fluorophore may emit a signal after the oligonucleotide is used as a primer for amplifying the nucleic acid.

The oligonucleotides that are used in the disclosed methods may be suitable as primers for amplifying at least one nucleic acid in the sample and as probes for detecting at least one nucleic acid in the sample. In some embodiments, the oligonucleotides are labeled with at least one fluorescent dye, which may produce a detectable signal. The fluorescent dye may function as a fluorescence donor for fluorescence resonance energy transfer (FRET). The detectable signal may be quenched when the oligonucleotide is used to amplify a target nucleic acid. For example, the amplification mixture may include nucleotides that are labeled with a quencher for the detectable signal emitted by the fluorophore. Optionally, the oligonucleotides may be labeled with a second fluorescent dye or a quencher dye that may function as a fluorescence acceptor (e.g., for FRET). Where the oligonucleotide is labeled with a first fluorescent dye and a second fluorescent dye, a signal may be detected from the first fluorescent dye, the second fluorescent dye, or both. Signals may be detected at a gradient of temperatures (e.g., in order to determine melting profiles for duplex nucleic acids such as an amplicons, complexes that include probes hybridized to target nucleic acids, hairpin probes, or T probe complexes). Alternatively, signals may be detected at selected temperatures to determine melting profiles for duplex nucleic acids.

The disclosed methods may be performed with any suitable number of oligonucleotides. Where a plurality of oligonucleotides are used (e.g., two or more oligonucleotides), different oligonucleotides may be labeled with different fluorescent dyes capable of producing distinguishable detectable signals. In some embodiments, oligonucleotides are labeled with at least one of two different fluorescent dyes. In further embodiments, oligonucleotides are labeled with at least one of three different fluorescent dyes.

In some embodiments, each different fluorescent dye emits a signal that can be distinguished from a signal emitted by any other of the different fluorescent dyes that are used to label the oligonucleotides. For example, the different fluorescent dyes may have wavelength emission maximums all of which differ from each other by at least about 5 nm (preferably by least about 10 nm). In some embodiments, each different fluorescent dye is excited by different wavelength energies. For example, the different fluorescent dyes may have wavelength absorption maximums all of which differ from each other by at least about 5 nm (preferably by at least about 10 nm).

Where a fluorescent dye is used to determine the melting profile of a nucleic acid in the method, the fluorescent dye may emit a signal that can be distinguished from a signal emitted by any other of the different fluorescent dyes that are used to label the oligonucleotides. For example, the fluorescent dye for determining the melting profile of a nucleic acid may have a wavelength emission maximum that differs from the wavelength emission maximum of any other fluorescent dye that is used for labeling an oligonucleotide by at least about 5 nm (preferably by least about 10 nm). In some embodiments, the fluorescent dye for determining the melting profile of a nucleic acid may be excited by different wavelength energy than any other of the different fluorescent dyes that are used to label the oligonucleotides. For example, the fluorescent dye for determining the melting profile of a nucleic acid may have a wavelength absorption maximum that differs from the wavelength absorption maximum of any fluorescent dye that is used for labeling an oligonucleotide by at least about 5 nm (preferably by least about 10 nm).

The methods may include determining the melting profile of at least one nucleic acid in a sample (e.g., an amplicon or a duplex nucleic acid that includes a probe hybridized to a target nucleic acid or a probe hybridized to self-complementary regions or a probe hybridized to a complementary capture sequence), which may be used to identify the nucleic acid. Determining the melting profile may include exposing an amplicon or a duplex nucleic acid to a temperature gradient and observing a detectable signal from a fluorophore throughout the temperature gradient. Alternatively, determining the melting profile may include exposing an amplicon or a duplex nucleic acid to select discrete temperatures and observing the detectable signal only at the selected discrete temperatures. Optionally, where the oligonucleotides of the method are labeled with a first fluorescent dye, determining the melting profile of the detected nucleic acid may include observing a signal from a second fluorescent dye that is different from the first fluorescent dye. In some embodiments, the second fluorescent dye for determining the melting profile of the detected nucleic acid is an intercalating agent. Suitable intercalating agents may include, but are not limited to SYBR™ Green 1 dye, SYBR dyes, Pico Green, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-aminoactinomycin D, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, and mixtures thereof. In suitable embodiments, the selected intercalating agent is SYBR™ Green 1 dye.

In the disclosed methods, each of the amplified target nucleic acids, reporter probe-template pairs or hybridized probes may have different melting temperatures or different melting profiles. For example, each of the amplified target nucleic acids, reporter probe-template pairs or hybridized probes may have melting temperatures that differ by 1-10° C., for example, at least about 1° C., more preferably by at least about 2° C. or 4° C., or even more preferably by at least about 5° C. from the melting temperature of any of the other amplified target nucleic acids, reporter probe-template pairs or hybridized probes.

As used herein, "labels" or "reporter molecules" are chemical or biochemical moieties useful for labeling a nucleic acid. "Labels" and "reporter molecules" include fluorescent agents, chemiluminescent agents, chromogenic agents, quenching agents, radionuclides, enzymes, substrates, cofactors, scintillation agents, inhibitors, magnetic particles, and other moieties known in the art. "Labels" or "reporter molecules" are capable of generating a measurable signal and may be covalently or noncovalently joined to an oligonucleotide.

As used herein, a "fluorescent dye" or a "fluorophore" is a chemical group that can be excited by light to emit fluorescence. Some suitable fluorophores may be excited by light to emit phosphorescence. Dyes may include acceptor dyes that are capable of quenching a fluorescent signal from a fluorescent donor dye. Dyes that may be used in the disclosed methods include, but are not limited to, fluorophores such as, a red fluorescent squarine dye such as 2,4-Bis[1,3,3-trimethyl-2-indolinylidenemethyl]cyclobutenediylium-1,3-dio-xolate, an infrared dye such as 2,4 Bis[3,3-dimethyl-2-(1H-benz[e]indolinylidenemethyl)]cyclobutenediylium-1,-3-dioxolate, or an orange fluorescent squarine dye such as 2,4-Bis[3,5-dimethyl-2-pyrrolyl]cyclobutenediylium-1,3-diololate. Additional non-limiting examples of fluorophores include quantum dots, Alexa Fluor™ dyes, AMCA, BODIPY™ 630/650, BODIPY™ 650/665, BODIPY™-FL, BODIPY™-R6G, BODIPY™-TMR, BODIPY™-TRX, Cascade Blue™, CyDye™, including but not limited to Cy2™, Cy3™, and Cy5™, a DNA intercalating dye, 6-FAM™, Fluorescein, HEX™, 6-JOE, Oregon Green™ 488, Oregon Green™ 500, Oregon Green™ 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, or Texas Red™.

Fluorescent dyes or fluorophores may include derivatives that have been modified to facilitate conjugation to another reactive molecule. As such, fluorescent dyes or fluorophores may include amine-reactive derivatives, such as isothiocyanate derivatives and/or succinimidyl ester derivatives of the fluorophore.

The oligonucleotides and nucleotides of the disclosed methods may be labeled with a quencher. Quenching may include dynamic quenching (e.g., by FRET), static quenching, or both. Suitable quenchers may include Dabcyl. Suitable quenchers may also include dark quenchers, which may include black hole quenchers sold under the trade name "BHQ" (e.g., BHQ-0, BHQ-1, BHQ-2, and BHQ-3, Biosearch Technologies, Novato, Calif.). Dark quenchers also may include quenchers sold under the trade name "QXL™" (Anaspec, San Jose, Calif.). Dark quenchers also may include DNP-type non-fluorophores that include a 2,4-dinitrophenyl group.

The methods and compositions disclosed herein may be used in compartmentalized reactions. One approach for compartmentalizing reactions is by using droplets, which are isolated volumes of a first fluid that are completely surrounded by a second fluid or by a second fluid and one or more surfaces. In some embodiments, the first and second fluids are two immiscible liquids. Various embodiments disclosed herein employ a water-in-oil emulsion comprising a plurality of aqueous droplets in a non-aqueous continuous phase. All or a subset of the aqueous droplets may contain an analyte of interest. Emulsions are formed by combining two immiscible phases (e.g., water and oil), often in the presence of one or more surfactants. Basic types of emulsions are oil-in-water (o/w), water-in-oil (w/o), and bi-continuous. In droplet-based biological assays, the emulsion will typically be a water-in-oil emulsion with the assay reagents (e.g., PCR primers, salts, enzymes, etc.) contained in the aqueous phase. The "oil" phase may be a single oil or a mixture of different oils. Any suitable non-aqueous fluid may form the non-aqueous continuous phase of the emulsions disclosed herein. In some embodiments, the non-aqueous continuous phase comprises a mineral oil, a silicone oil, or a fluorinated oil (e.g., Fluorinert® FC-40 [Sigma-Aldrich]).

The droplets may be imaged using a variety of techniques. To facilitate imaging, the composition containing the droplets may be dispersed on a surface such that the droplets are disposed substantially in a monolayer on the surface. The imaging surface may be, for example, on a slide or in a chamber, such as a glass or quartz chamber. The droplets, as well as labeled analytes or reaction products (e.g., hairpin probes) within the droplets, may be detected using an imaging system. For example, detection may comprise imaging fluorescent wavelengths and/or fluorescent intensities emitted from labeled hairpin probes. In embodiments where the droplets also contain encoded particles, such as encoded microspheres, the imaging may comprise taking a first, decoding image of the encoded particles and taking a second assay image to detect the probes in the droplets. A comparison of the decoding image and the assay image permits greater multiplex capabilities by using combinations of fluorophores. The methods of the present invention may further comprise correlating the signal from directly or indirectly labeled amplification products with the concentration of DNA or RNA in a sample. Examples of imaging systems that could be adapted for use with the methods and compositions disclosed herein are described in U.S. Pat. No. 8,296,088 and U.S. Pat. Publ. 2012/0288897, which are incorporated herein by reference. Additionally, the use of encoded microspheres might aid in droplet tracking. Randomly-distributed, uniquely-encoded microspheres included at sufficient concentration would give each droplet a distinctive signature in relation to adjacent droplets. This signature would be useful to track droplets should any movement occur during PCR amplification or post-amplification melt analysis. The number of unique microsphere codes and the total number of microspheres in the assay can be optimized to insure minimal repetition of partition signatures.

Alternatively, in lieu of droplets, compartments or partitions may be formed in a static array on a planar surface through, for example, the controlled etching of a silicon, metal or glass or through conventional or microinjection molding techniques. Several different ways of forming static arrays or reaction chambers have been described, for example as in U.S. Pat. No. 9,039,993, PCT/US2003/041356, U.S. Pat. No. 6,391,559, EP2906348, U.S. Pat. No. 9,643,178 and Du. Et al. 2009 "SlipChip." Lab on a Chip 9 (16):2286, incorporated herein by reference. Optimally, partitions are packed in close proximity to decrease the overall surface area and can be connected by microfluidic channels to improve partition filling. In the latter embodiments, methods such as those described in U.S. Pat. No. 9,163,277 may be used to ensure complete separation of partitions after filling.

As discussed above, the polymerase chain reaction (PCR) is an example of a reaction that may be performed within a partition. In particular, partitions are useful in digital PCR (dPCR) techniques. dPCR involves partitioning the sample such that individual nucleic acid molecules contained in the sample are localized in many separate regions, such as in individual wells in microwell plates or micropartitions, in the dispersed phase of an emulsion, or arrays of nucleic acid binding surfaces. Ideally, each partition will contain 0 or 1 copy of the target nucleic acid, providing a negative or positive reaction, respectively. Unlike conventional PCR, dPCR is not dependent on the number of amplification cycles to determine the initial amount of the target nucleic acid in the sample. Accordingly, dPCR eliminates the reliance on exponential data to quantify target nucleic acids and provides absolute quantification. Bead emulsion PCR, which clonally amplifies nucleic acids on beads in an emulsion, is one example of a dPCR technique in which the reactions are portioned into droplets. See, e.g., U.S. Pat. Nos. 8,048,627 and 7,842,457, which are hereby incorporated by reference. When dPCR is performed in an emulsion, the emulsion should be heat stable to allow it to withstand thermal cycling conditions.

There are various ways of performing dPCR in an emulsion or on a static array. In either case, a DNA sample is diluted to an appropriate concentration, mixed with PCR reagents (primers, dNTPs, etc.) and partitioned accordingly into a number of discrete reaction samples. The partitions are subjected to PCR thermal cycling and the amplicons detected by florescence (or other suitable reporter) imaging as described above. In the context of the present cleavable probe embodiments, amplicons are detected by changes in florescence (or other suitable reporter) of the probes.

Thermal cycling of the partitions may be performed by any suitable technique known in the art. For example, partitions may be thermal cycled in a tube or chamber than can be heated and cooled. In some embodiments, the methods employ continuous-flow amplification to amplify the nucleic acid template. Various methods of continuous flow amplification have been reported. For example, U.S. Pat. No. 7,927,797, which is incorporated herein by reference, describes a water-in-oil emulsion used in conjunction with a continuous flow PCR. Alternatively, droplets may be arranged in a 2D array and thermal cycled using a flat block thermal cycler as in methods used to thermal cycle in static array based digital PCR. Isothermal reactions (e.g., rolling circle amplification, whole genome amplification, NASBA, or strand displacement amplification) may also be performed in droplets or static array partitions. The system may also be used to monitor droplets or partitions while increasing or decreasing the temperature to obtain melt profiles of probes within partitions, which allows for multiplexed detection and quantification. The probes themselves may be used within droplets or partitions to isothermally amplify signal such that other forms of amplification such as PCR or other isothermal amplification reactions are not necessary to detect low copy numbers of target within a droplet or static array partition.

III Discrete Melt Methods for Quantification

A melting curve (dissociation curve) charts the change in fluorescence observed when double-stranded DNA dissociates or "melts" into single-stranded DNA as the temperature of the reaction is raised. For example, when double-stranded DNA is slowly heated in the presence of intercalating dyes, a sudden decrease in fluorescence is detected as the melting point (Tm) is reached and the dye dissociates from the duplex. Because the Tm of nucleic acids is affected by length, GC content, and the presence of base mismatches, among other factors, different duplex nucleic acids can be distinguished by their different melting characteristics. Post-amplification melting curve analysis can also be used to distinguish primer-dimer artifacts and non-target nucleic acids from target-derived amplicons to ensure reaction specificity. Moreover, the characterization of reaction products, e.g., primer-dimers vs. amplicons via melting curve analysis reduces the need for time-consuming gel electrophoresis. The specificity of a real-time PCR assay is determined by the primers and reaction conditions used. However, there is always the possibility that even well designed primers may form primer-dimers or amplify a nonspecific product. There is also the possibility when performing qRT-PCR that the RNA sample contains genomic DNA, which may also be amplified. The specificity of the qPCR or qRT-PCR reaction products can be confirmed using melting curve analysis.

High-resolution melt curve (HRM) analysis is a homogeneous, post-amplification method for identifying single nucleotide differences, e.g., SNPs, novel mutations, and methylation patterns. HRM analysis is a more sensitive approach to traditional melt curve profiling, in which double-stranded DNA is monitored for the temperature (Tm) at which it dissociates into single-stranded DNA. In HRM, the amplification reaction is subjected to small, incremental temperature increases (typically 0.1-0.5° C. per minute) while fluorescence is monitored continuously. In the presence of intercalating dyes that bind double-strand nucleic acids, fluorescence decreases slowly until the temperature approaches the duplex Tm and at the Tm, a dramatic decrease in fluorescence is observed as the sample transitions from double stranded to single stranded DNA. Since Tm is dependent on, amongst other things, nucleotide sequence and the presence of mismatched nucleotides in a duplex, mutations can be detected in HRM analysis as either a shift in Tm or as a change in shape of the melting curve. In contrast to traditional melt curve analysis, HRM can provide single-nucleotide discrimination between amplicons.

Figure 1B:
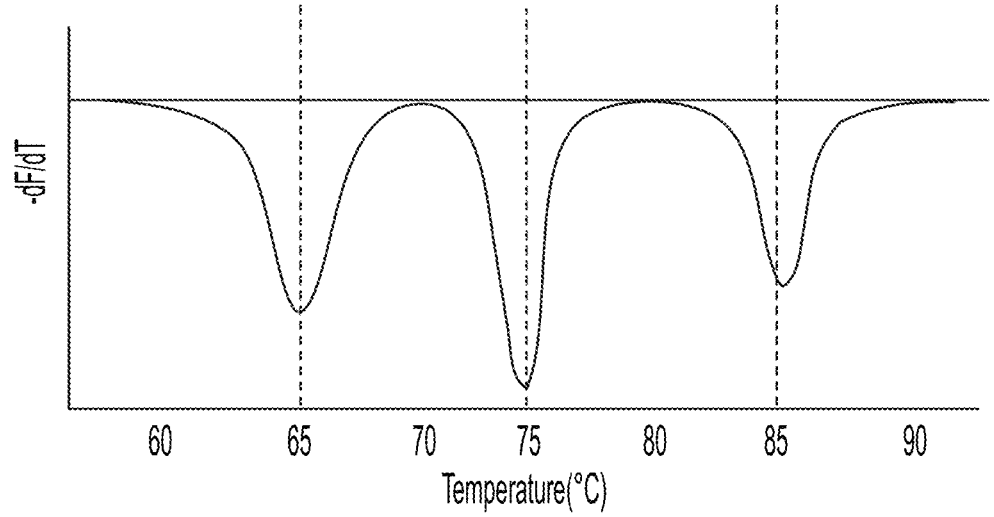

By taking fluorescence measurements at many temperature intervals—at 2° C. intervals or smaller, such as at 1° C., 0.5° C., 0.3° C., 0.2° C., or even 0.1° C. intervals—one can track the rate of change of fluorescence intensity (i.e., the derivative of the fluorescence intensity with respect to temperature) and determine the temperature or temperatures (Tm) at which significant melt activity occurred. The peaks in a plot of the derivative of relative fluorescence units (RFU) with respect to temperature correspond to melt temperatures (Tms) of target duplexes. For example, FIGS. 1A and 1B show plots of RFU versus temperature and the negative derivative with respect to temperature from continuous monitoring of fluorescence as temperature increases in a sample containing 3 target probes with melt temperatures of 65° C., 75° C., and 85° C., respectively. A comparison of the measured Tm with the expected Tm for a particular probe or duplex nucleic acid is used to determine whether the target nucleic acid was amplified.

Traditionally, in dPCR applications, post-amplification end-point measurements of fluorescence in individual partitions have been used to determine the presence or absence of a target nucleic acid in a sample. More recently, melt analysis using intercalating dyes has been used to specifically identify target nucleic acids in dPCR. To distinguish between mere noise and an actual presence of a melt event, a threshold may be set for either or both the RFU plots and negative-derivative plots. For an RFU plot, a signal threshold may be selected by using a percentage of the standard deviation of a slope-corrected control curve, e.g., 200%, 300%, 400%, 500%, 1000%, or 2000% of the standard deviation. If the fluorescence intensity is determined to have changed beyond the threshold amount across a given melt temperature window (e.g., 60 to 70° C. for a target probe whose melt temperature is expected to be 65° C.), the target may be deemed to be present. For a negative-derivative plot, a signal threshold may be selected by using a percentage of the standard deviation of the negative derivative of the slope-corrected RFU curve for a control sample, e.g., 200%, 300%, 400%, 500%, 1000%, or 2000% of the standard deviation. Then, if any negative-derivative low peaks are determined to be more than the threshold magnitude below zero, a positive melt event is deemed to have occurred for the relevant target probe, and the corresponding target is determined to be present in that partition. Threshold values can alternatively be set by considering historical data and using a fraction of typical magnitudes of the negative-derivative melt peaks. For example, a threshold might be set anywhere from 10% to 50% of the average negative-derivative melt peak magnitude for that specific target probe.

US2016/0310949 describes using unique melt signatures generated from traditional or high resolution melt analysis (FIRM) in a digital microfluidic system to achieve quantitative multiplexing in dPCR. WO2015023616 describes a digital system in which target nucleic acids are non-specifically amplified using universal primers and HRM analysis is used to identify individual bacterial species. Melt signatures in individual wells containing target nucleic acids are compared to standard melt curves to identify the target sequence present. Accurate identification of individual bacterial species requires careful comparison of melt profiles among unique targets, and therefore relies on high resolution melt data, typically $\Delta T<1°$ C.

Discrete Melt Analysis (DMA) provides an improved method for performing melt analysis that requires fewer measurements of fluorescence versus temperature and thus results in faster data collection and analysis, and consequently provides lower turnaround times for assays. As a concept, DMA represents an under-sampling of continuous melt or HRM analysis. In contrast to the latter two methods, DMA requires measurement of fluorescence at only 2 temperatures per target and does not require the calculation of a Tm to identify a target nucleic acid. Fluorescence images for a particular target nucleic acid are acquired at (1) a temperature at which all probes or duplex nucleic acids representing the target are in a hybridized, duplex conformation and (2) a temperature at which all probes or duplex nucleic acids representing the target are in a single stranded conformation, or fully denatured. Use of appropriate labeling schemes that distinguish these 2 conformations permits detection of changes of conformation at the two measurement temperatures in the presence of target. This concept is represented in FIG. 2 for a sample having a single target-specific probe (left) and a sample having 3 target-specific probes (right) that are distinguishable by having unique Tms.

DMA is particularly well suited to melt analysis performed using probes such as those described in U.S. application Ser. No. 14/82,288, incorporated herein by reference, and provides an efficient and cost-effective means of multiplexing in digital amplification systems.

The present methods may use a cleavable probe that has a predetermined, unique melt signature to identify the presence of a specific, target nucleic acid in an individual partition in digital PCR. In particular aspects, the present methods concern the use of a discrete melt signature derived from fluorescence images acquired at only two temperatures, rather than multiple images acquired at numerous temperatures to confirm the presence of the target nucleic acid. The use of DMA specifically does not require the acquisition of a fluorescence image at the Tm of the duplex nucleic acid or probe being detected.

The use of target-specific cleavable melt probes provides two mechanisms of improving specificity, as target-specific probes can reduce the incidence of detecting non-specific amplification products while discrete melt analysis enabled by such probes provides an efficient means of confirming presence and identity of detected targets. Further, the present methods can use target-specific cleavable probes to enhance multiplexing capabilities in dPCR applications.

Accordingly, the present methods may be used for detecting one or more targets in a reaction mixture. The methods may be applied to both qPCR and dPCR reactions. For dPCR reactions, three or more unique melt signatures may be detected in a single partition using a single fluorescence channel, meaning at a minimum, with four different fluorescence channels, 12 unique targets may be detected in a single partition.

Importantly, the methods described herein provide a solution to time-consuming, melt analysis requiring numerous images to be acquired as incremental changes in temperature are made. The method is considered particularly useful in dPCR applications where image acquisition and data processing from traditional and HRM melt curve analysis is time consuming and computationally intensive. DMA requires the acquisition of a minimum of n+1 images for target elucidation where n=the number of different target-specific probes that emit fluorescence at the same wavelength. This can significantly decrease the number of images necessary to determine target presence without sacrificing the ability to accurately identify and quantify the target. In contrast to traditional melt analysis and HRM, the present method alternatively uses discrete fluorescence measurements taken at temperatures above and below pre-determined probe Tms and utilizes step changes in intensity to indicate the presence of specific targets.

In an embodiment, cleavable probes such as those described in U.S. application Ser. No. 14/823,288 are designed such that probes specific for a first target, after target hybridization-mediated cleavage, followed by hairpin formation that supports extension of the cleaved probe, exhibit a Tm that is at least 5° C. different than probes specific for any other target nucleic acid in the reaction mixture. Under these conditions, a plot of the derivative of a melt profile for each set of probes in a multiplex detection scheme yields highly differentiated melt peaks that are distinguishable from each other. In a preferred embodiment, different probe Tms are separated by about 10° C. such that all probes that melt at the same Tm are fully denatured/single stranded before probes designed to melt at higher Tm's begin to denature. Typically, the probes are included in the amplification reaction mixture and after amplification, are used to determine a melt profile for modified probes in the reaction mixture. The cleavable probes exhibit different fluorescent intensity depending on whether they have encountered their cognate target nucleic acids and been cleaved and extended or not. In the embodiment presented in FIGS. 2-7, the probes exhibit fluorescence in the absence of target as a result of having a fluorescent reporter coupled to the 5' end of the probe and the fluorescence is quenched via incorporation of a quencher during extension.

Image Acquisition

Use of probes having pre-determined Tms in DMA permits measuring fluorescence at temperatures intervals lower than and higher than pre-determined melt peaks to elucidate target presence after amplification. The left panel of FIG. 2 illustrates the acquisition of only 2 fluorescence images (taken at the temperatures denoted by X) during melt analysis of a single probe having a predetermined Tm. Note that image acquisition does not take place at the predicted Tm of the probe. The right hand panel of FIG. 2 illustrates that for a reaction mixture containing three probes each with a unique melt peak (Tm1=65° C., Tm2=75° C. and Tm3=85° C.) respectively and detectable in the same fluorescence channel, only four images are required to generate a melt profile. The first image is acquired at a temperature T1 that is at or slightly lower than the annealing temperature for primers used in PCR amplification and at which all probes that have encountered their corresponding target are in a hybridized, duplex state after amplification. The second image is acquired at a temperature T2, at which Tm1 probes will be denatured, but probes having a Tm>Tm1 remain in the hybridized state. The third image is acquired at T3, a temperature intermediate Tm2 and Tm3. The fourth image is acquired at the denaturation temperature T4, which is greater than Tm3 and at which all probes will be denatured. In dPCR applications, average fluorescence intensity in individual partitions is measured for all four acquired images.

In an alternate method, when using cleavable probes such as those described in U.S. application Ser. No. 14/823,288 (incorporated herein by reference), an initial image and associated fluorescence can be acquired prior to amplification, and represents maximal fluorescence of all probes in the reaction. This fluorescence measurement is theoretically equivalent to the image acquired at temperature T4, in which all probes in the reaction are fully denatured and exhibit maximal fluorescence regardless of whether they have encountered their cognate targets or not. After amplification, subsequent images can be acquired at temperatures T1, T2 and T3 for comparison to the image taken prior to amplification to measure changes in fluorescence as probes transition from a duplex conformation to a single stranded conformation as the temperature increases. This substitution of the high temperature (T4) image at which all probes are fully denatured by the pre-amplification image can be applied to any assay format in which unmodified (pre-amplification) probes are maximally fluorescent and those same probes, once modified show a change in signal based on whether they have encountered target.

The choice of measurement temperatures can be based on prior clinical or laboratory data showing where the flattest regions of the RFU-versus-temperature plot occur on either side of the melt peak for each probe (i.e., lower than the lowest melt temperature, and higher than the highest melt temperature). Alternatively, the measurement temperatures can also be chosen based on the highest points (least negative values) flanking the peak of the negative derivative curve (Tm). Even without prior high-resolution RFU and/or derivative data spanning the entire relevant temperature region, measurement temperatures can still be chosen simply by choosing temperatures lower than, and higher than the predetermined melt temperatures for each probe in the reaction mixture. This process can be further supported with in silico modeling data. While FIG. 2 shows the fluorescence images to be acquired at evenly spaced temperature intervals, this is not a requirement.

The fluorescence intensity plot shown in FIG. 2 has been idealized, where the fluorescence at temperatures lower and higher than the target melt temperatures show little change resulting in relatively shallow, nearly flat slopes (slopes approaching zero). In reality, however, photobleaching and/or temperature dependence of fluorescent reporter dyes can alter the slope of fluorescence over the relevant temperature range. A slope correction and/or normalization can be applied to the raw data for fluorescence intensity versus temperature prior to melt analysis for clearer identification of melt signatures.

FIGS. 3-7 illustrate an image-analysis process used to determine the number of input target copies using DMA in dPCR applications. FIG. 3 shows the same three targets A, B, and C described for FIG. 2 distributed in various combinations among 36 partitions, including 4 partitions having no target (empty partitions). In this example, some partitions contain only target A, target B, or target C, some contain two targets (AB, BC, or AC), some contain three targets (ABC), and some contain no targets after amplification. Targets can be detected using the same probes described for FIG. 2, which are designed to have unique melt temperatures Tm1, Tm2 and Tm3 wherein Tm1<Tm2<Tm3.

Figure 5:
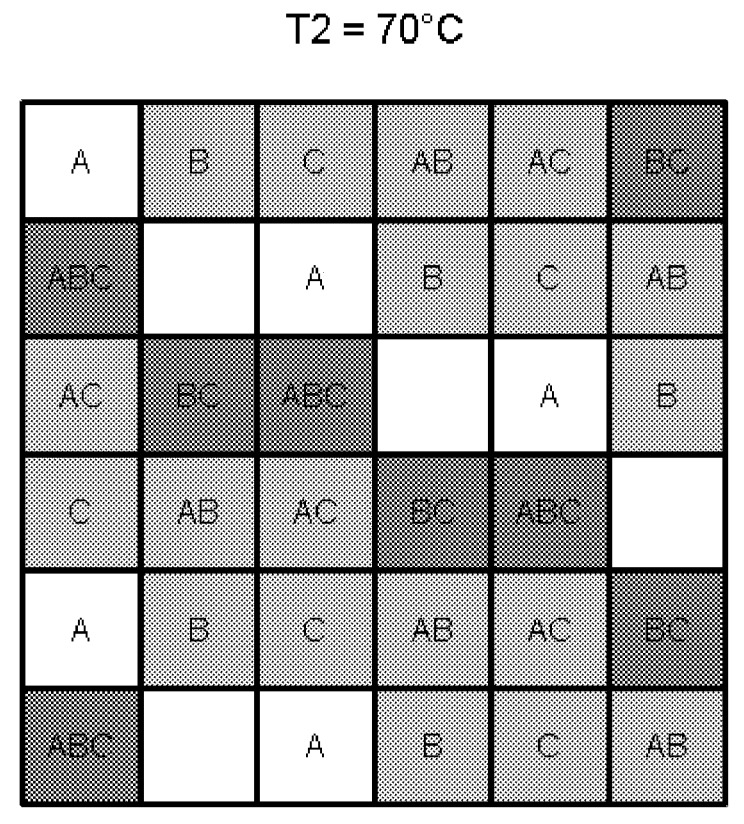

In this embodiment, the image analysis process generally involves comparing two fluorescence images acquired at temperatures higher than and lower than an expected melt temperature for a given target probe or duplex following target amplification. Initially, a starting fluorescence intensity image is acquired at a temperature T1 (in this example 60° C.) that is lower than Tm1. FIG. 4 is illustrative of fluorescence intensities at T1 in individual partitions of the system shown in FIG. 3 after amplification is complete. The image shown in FIG. 4 represents a condition at which all probes are in a duplex (hairpin) configuration, with only non-cleaved, non-extended probes (i.e. probes for which no target is present) emitting fluorescence. At this condition, fluorescence from probes for all 3 targets that have been cleaved and extended in the presence of their corresponding target nucleic acids will be quenched, resulting in decreased fluorescence intensity relative to conditions in which no targets were present, or conditions in which cleaved and extended probes are denatured. Next, the temperature is increased to a temperature T2 (in this example, 70° C.) that is higher than Tm1 but lower than Tm2, and a second image is acquired (FIG. 5). At this temperature and in the presence or target A, target A-specific probes will be denatured and show a relative increase in fluorescence as a result of a loss of quenching.

To determine the number of partitions testing positive for target A, the following image processing steps are performed: i) calculate average pixel intensity in individual partitions, defined as the integrated pixel intensity values in an individual partition divided by the number of pixels in the partition image; ii) determine a ratio of average fluorescence intensity at T2 versus T1 ($F_{T2/T1}$); iii) Plot the results of the image comparison to identify partitions showing a change in fluorescence intensity across the temperature measurement window. Alternatively, one may subtract the fluorescence values taken at T1 from those acquired at T2 ($F_{T2-T1}$) (using the average intensity values) rather than using a ratio. The average intensity value may also only interrogate a subset of pixels or region of interest (ROI) within the partition. Alternatively, the integrated intensity can be substituted for average intensity in all analyses described herein. Finally, ratios or subtractions can be performed directly between images on a pixel-by-pixel basis and partition intensity (average or integrated) can be determined from the resulting images.

In FIGS. 3-7 the change in fluorescence represents an increase in fluorescence as hairpin probes containing a fluorophore and quencher at each end denature, thus separating the fluorophore and quencher molecules. Of course alternative detection chemistries and labeling schemes that result in a decrease in fluorescence intensity as the duplex denatures during melt analysis may also be used.

Figure 6A:
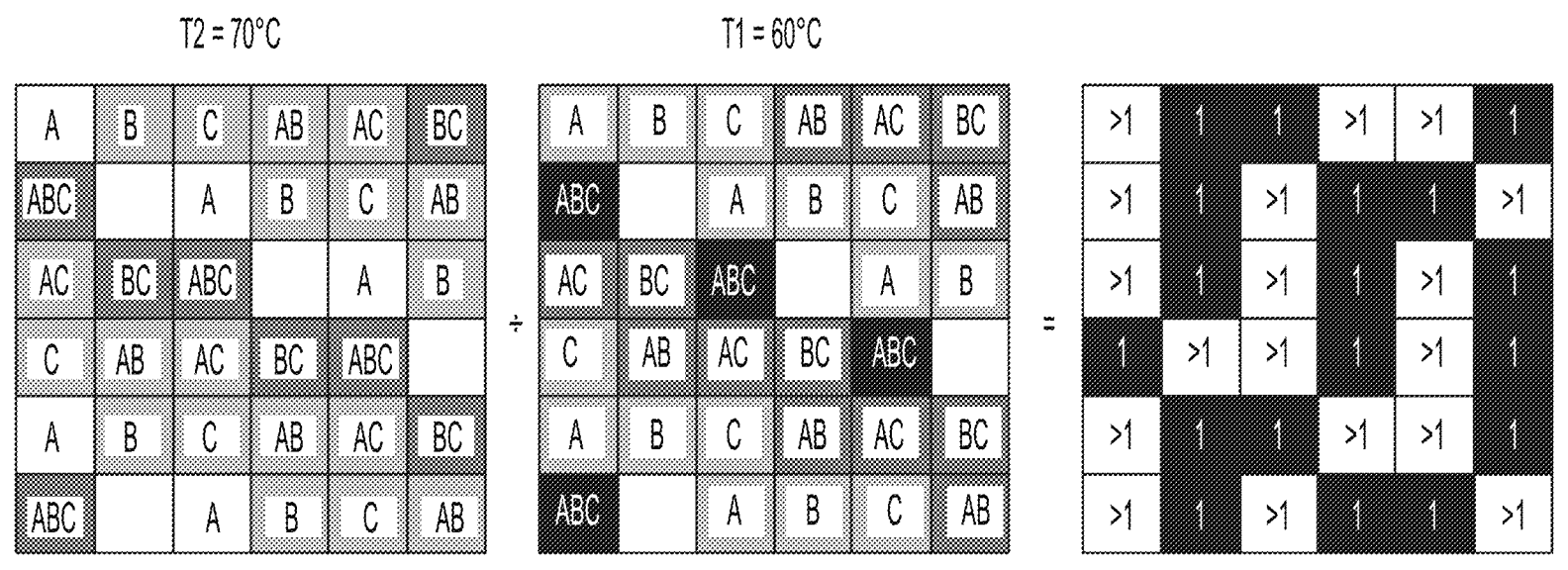
Figure 6B:
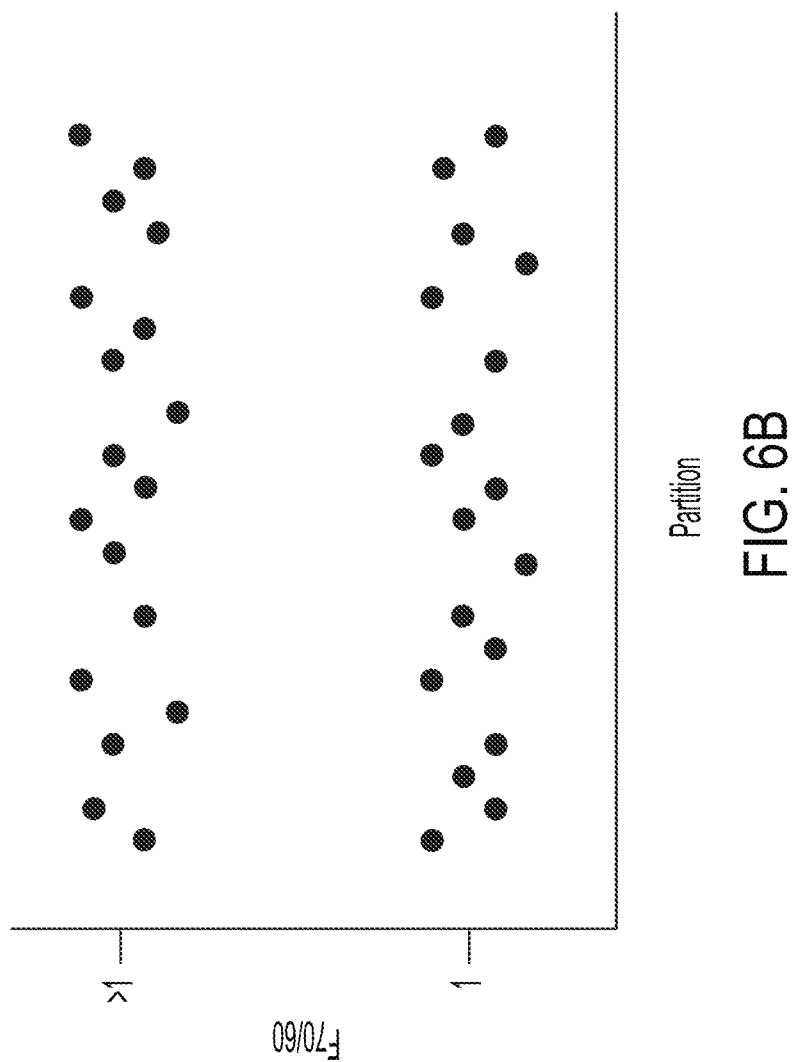
FIG. 6B represents a 1D amplitude plot showing 2 clusters (>1 and 1) of partitions corresponding to partitions determined to be negative for a target (1) and partitions determined to be positive for a target (>1).
Figure 7A:
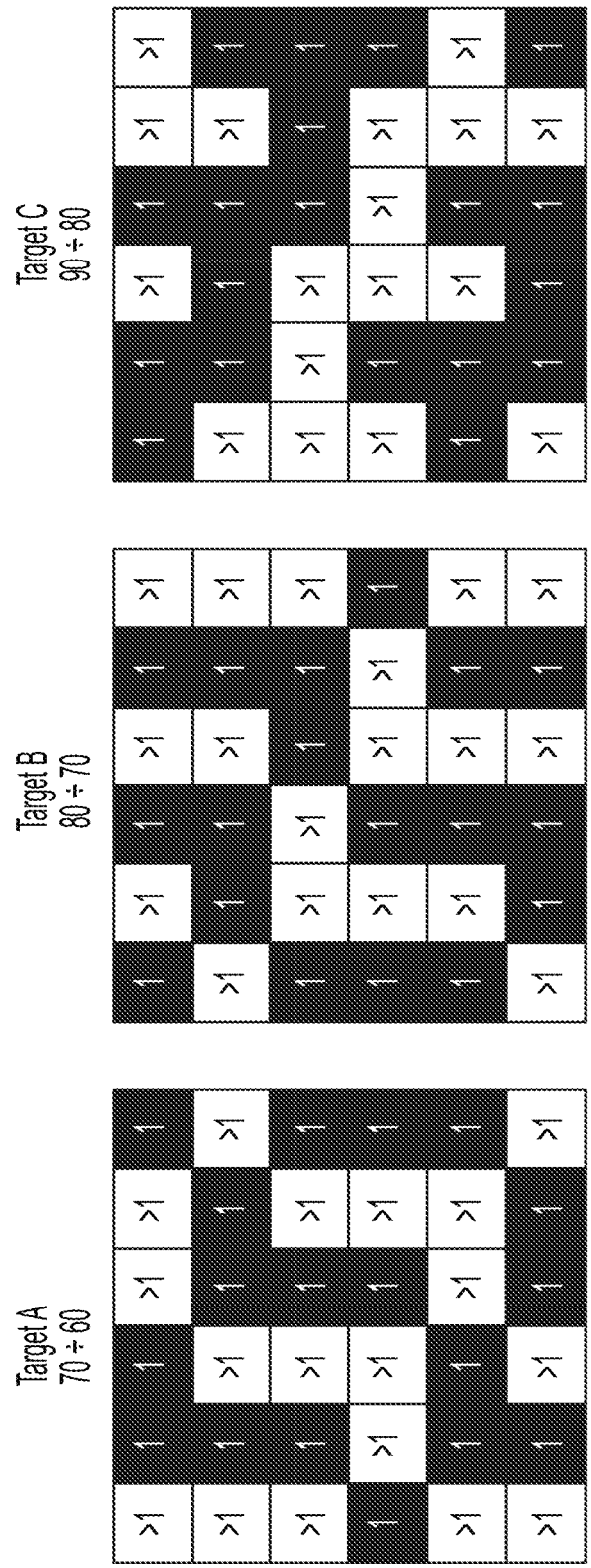
FIG. 7: Example of image comparisons of images taken at T1, T2, T3 and T4 for the system shown in FIG. 3 to determine presence or absence of targets in each compartment (A). Comparison of fluorescence intensities calculated for each partition at T2 versus T1, T3 versus T2, and T4 versus T3 to generate the accompanying 1D amplitude plots results in a cluster of partitions determined to be negative (1) for a target and a cluster of partitions determined to be positive (>1) for a target for each set of temperatures (B).
Figure 7B:
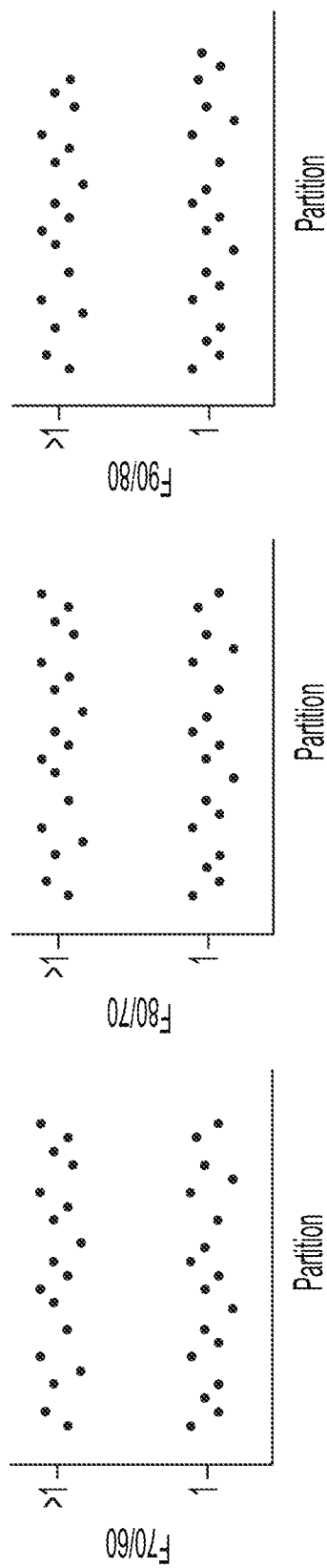
Figure 8A:
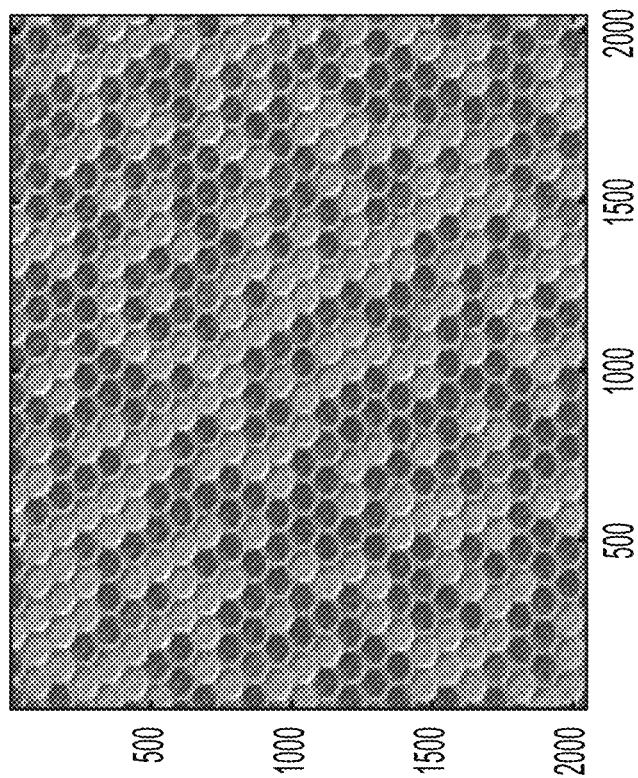
FIGS. 8A and 8B show raw data and normalized (with respect to image taken at 95° C.) fluorescence images, respectively.
Figure 8B:
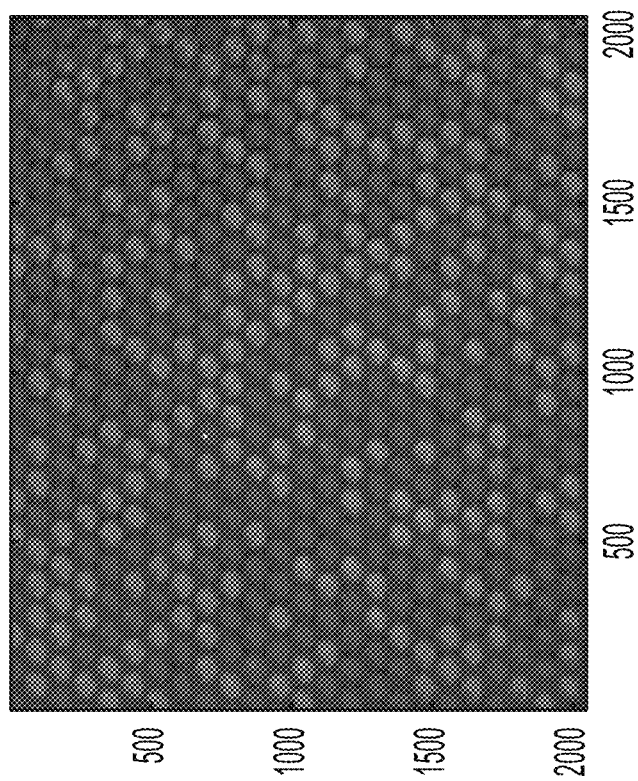
Figure 8D:
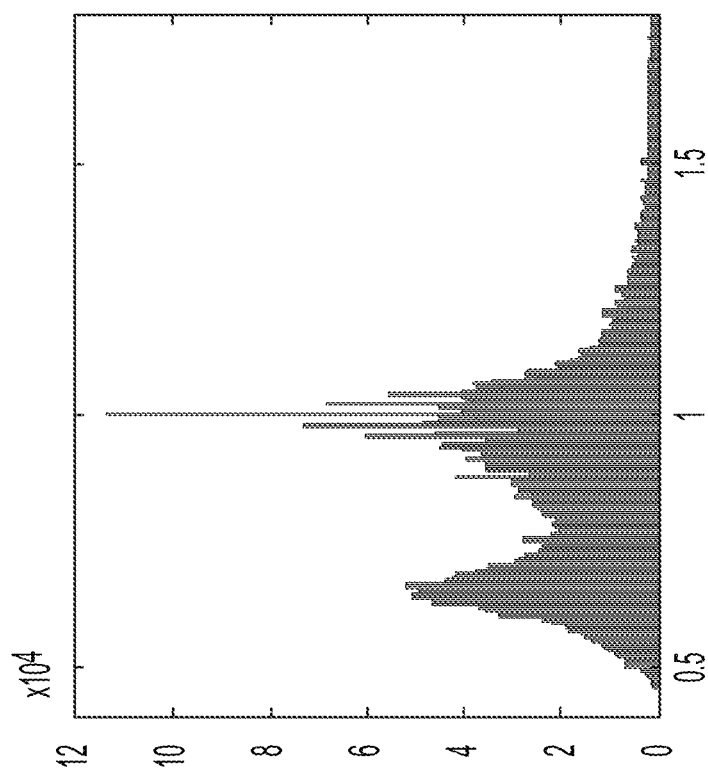
FIGS. 8C and 8D show the corresponding intensity histograms.
Figure 8C:
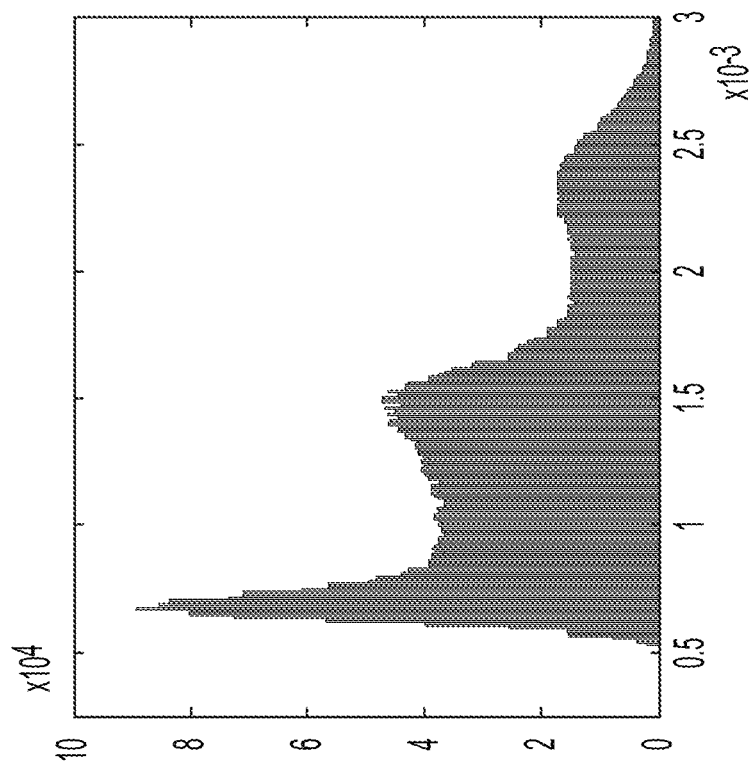

The image acquired at T2 also represents an image taken at a temperature lower than the predetermined Tm of target B whose melt temperature is Tm2. The same general procedure can be performed for each target at temperatures higher than and lower than the predetermined Tm of each probe. A feature of DMA is that a measurement taken at a temperature Tx that is higher than the predetermined Tm for a designated probe may also serve as the measurement taken at a temperature lower than the predetermined Tm of a probe having a Tm higher than Tx, therefore it is not necessary to take at least 2 measurements for each probe. Thus, if a reaction mixture contains n target-specific probes having different Tms, fluorescence images need only be acquired at n+1 different temperatures. FIG. 6 is an example of image comparison for the system shown in FIG. 3, where the average fluorescence intensity calculated at T2 (70° C.) is divided by the intensity calculated at T1 (60° C.) to determine which partitions show a change in intensity. The resulting 1D amplitude plot (FIG. 6, bottom), contains clusters of partitions at two intensities, corresponding to partitions that are negative for a target (no distinguishable change in fluorescence intensity between successive images results in a ratio close to 1) or positive for a target (change in fluorescence intensity between successive images results in a ratio >1). Classification of partitions into these two groups can be done by setting a manual threshold or by using an algorithm-based approach such as k-means clustering. Once images are acquired at temperatures lower than and higher than respective Tms for all target probes, image analysis is performed to compare respective sets of images and calculate fluorescence intensity ratios for each set of measurements (FIG. 7). Plotting the ratio of partition intensities between the set of images permits calculation of the corresponding number of positive and negative partitions. Once the number of partitions testing positive for each target is known, the average number of target input copies per partition, k, can be estimated using Poisson statistics. Equation 1 can be applied to each target individually. It is important to note that the distributions of targets A, B and C across partitions are assumed to be independent, and therefore, partitions that may be negative for target A in the calculation of Equation 1, may be positive for targets B or C or both. This does not however, affect quantification of individual targets.

$$\lambda = \text{average copies/partition} = -\ln\left(\frac{\#_{negative}}{\#_{total}}\right) \quad \text{Equation 1}$$

Confidence intervals within +/−Z standard deviations from average loading (λ) are given by the expression in Equation 2 where $\lambda_{CI_L}$ is the lower limit and $\lambda_{CI_U}$ is the upper limit of the confidence interval. For a 95% confidence interval, Z=1.96. Alternative confidence intervals can be obtained with appropriate substitutions for Z. Confidence intervals narrow as the number of partitions increases if the volume of the partitions is held constant. Increasing the number of partitions would therefore be one way to increase the precision of estimating the average input target copies per partition.

$$\lambda_{CI_L} = \lambda e^{-Z\sqrt{e^{\lambda}-1}/\lambda\sqrt{N}}; \lambda_{CI_U} = \lambda e^{+Z\sqrt{e^{\lambda}-1}/\lambda\sqrt{N}} \quad \text{Equation 2}$$

To quantify precision, the expression in Equation 3 compares the span of the confidence interval to the average number of target copies per partition. Smaller values denote greater degrees of precision. While relative standard deviations and relative confidence intervals may increase dramatically at the limits of quantifiable detection (i.e., very few target-positive or very few target-negative partitions), the magnitude of error in those cases may still be acceptable. For example, when trying to detect an extremely rare target, the simple presence of the target may itself already be extremely valuable information regardless of the degree of error.

$$\phi = \frac{\max(|\lambda - \lambda_{CI_L}|, |\lambda - \lambda_{CI_U}|)}{\lambda} \quad \text{Equation 3}$$

Data Analysis

Strategies for optimizing data analysis using images acquired both before and after dPCR amplification are also provided. Such strategies include using an image acquired before or after amplification to normalize fluorescence intensities measured during melt analysis (See Example 2), and establishing a background (negative partition) threshold to distinguish positive and negative signals from background using pre-and-post-amplification images (See Example 3). Further embodiments (see Example 4) provide methods for correcting images acquired during melt analysis to account for temperature- and light-dose dependent changes in fluorescence intensity over the thermal profile. For example, FAM is known to be very photo sensitive, showing reduced fluorescence intensity with increased photo exposure, and many dyes such as FAM and HEX show decreased fluorescence at higher temperatures.

Example 5 provides methods for comparing pre- and post-amplification images for preliminary identification of partitions that contain 0 or 3 targets. It may be desirable to eliminate such partitions from further analysis to simplify and reduce the time needed for data analysis. Preliminary identification of partitions that will not be included in data analysis is also useful to limit the number of images acquired during the melt step, since no images need be acquired for these partitions. This method thus permits image acquisition only from partitions of interest as a result of being deemed suitable for yielding useful data. In certain experimental conditions, this might greatly reduce the melt acquisition time and subsequent data analysis.

Accordingly, the present methods provide improved classification of partitions as positive or negative for one or more targets which leads to improved quantification. In contrast to methods that rely on DNA intercalating dyes for melt analysis, the present methods make use of melt analysis of target-specific probes to enhance specificity while retaining flexibility in assay design (e.g., primer regions, amplicon length, etc.). In addition, the described methods rely on the use of a low resolution digital melt profile to detect and identify target nucleic acids, which simplifies melt data acquisition and analysis and ultimately results in faster data acquisition and analysis of data.

DMA requires fewer data points than traditional continuous melt analysis, which reduces the time required for data acquisition, and results in fewer images to process and less photobleaching of photosensitive reporter probes. This is particularly useful in an imaging-based digital PCR scenario where many images of partitions (i.e. droplets or static array partitions) are processed at each melt temperature. Melt analysis of dPCR reactions typically requires images to be acquired across an array of partitions at each temperature of the melt profile. Depending on the number of partitions, the area over which images are acquired can be quite large. Additionally, images must be high enough in resolution to ensure robust partition identification and assignment as positive or negative for a target. This often requires acquiring multiple images per array of partitions. Further, in order to achieve multiplexing in digital as well as bulk volume assays, images are acquired in multiple fluorescence channels. By reducing the number of image acquisition events required for melt analysis, DMA has particular value in digital applications as it reduces the time required to acquire melt data and to process acquired images.

Use of DMA also provides an advantage in that samples are exposed to less potentially damaging light and high temperatures. Some commonly used fluorophores (e.g. FAM) are photosensitive. This photosensitivity is significant in digital PCR as the entire sample is interrogated for each fluorescence measurement in contrast to bulk volume PCR wherein a focal volume smaller than the total volume is typically interrogated. This difference is critical as fluorophores in the latter case are free to diffuse in and out of the focal volume and receive on average less excitation exposure and are thus less likely to experience photobleaching. Fluorophores in digital PCR reactions are exposed to increased amounts of incident excitation, particularly if melt analysis is performed, and are therefore more likely to experience photobleaching. DMA reduces the number of exposure events and thus the degree of photobleaching experienced by fluorophores. In some instances, repeated and continuous exposure of fluorescent probes to high temperatures also has adverse effects, which may be mitigated by DMA.

Another advantage to using DMA with cleavable probes, is that it provides enhanced specificity. The cleavable probes described in U.S. application Ser. No. 14/82,228 are cleaved and extended only in the presence of target DNA, but do not use target DNA as templates for extension. Therefore, such probes have very predictable Tms that do not vary even in the presence of target nucleic acid sequence variation. In contrast, nucleic acid duplexes and probe/target duplexes that have Tms that are at least partly determined by the composition of target nucleic acids or amplification products thereof, can show variations in Tm from sample to sample as a result of minor target sequence variations. It is for this reason that HRM typically requires determining the melt peak in order to confirm the identity of an unknown target sequence in a sample. In contrast, the use of DMA combined with cleavable probes does not require determination of a melt peak Tm to determine the identity of a target nucleic acid. DMA requires fluorescence intensity values acquired only at a temperature lower than and a temperature higher than the expected Tm of the probe to determine the ratio or difference between the two values in order to discriminate positive from negative samples. DMA may also include acquiring fluorescence intensity values at additional preselected temperatures, but does not require determination of a melt temperature to identify a target. Furthermore, in some embodiments, fluorescence intensity values may be acquired prior to amplification instead of at a temperature at which all probes in the reaction are denatured.

DMA is, however, not limited to dPCR embodiments. It is also readily applicable to real-time PCR and qPCR melt analysis applications to reduce time required for acquiring data for melt profiling. The method is also applicable to other probe-based detection methods such as Molecular Beacons (MB), TaqMan, TOCE technology and to particular uses of DNA intercalating dyes such as SYBR or EvaGreen.

Molecular Beacon probes can be designed to have unique, predetermined melt temperatures. However, since melt analysis using MB probes reflects the dissociation of the probe from a target sequence with which it has hybridized, the melt temperature is determined by the target sequence and is thus constrained in terms of design. As temperature is increased during MB probe melt analysis, fluorescence decreases as the MB probe dissociates from the target and adopts a random coil configuration. Similarly, for melt analysis using TaqMan probes, melt profiles are determined by the target sequence intended to be detected and probe design is thus constrained. Melt analysis using Molecular Beacon and TaqMan probes is described in Huang et al., *PLoS One*, 6(4) 2011, incorporated herein by reference. MB and Taqman probes designed to have predetermined melt profiles can be also used in DMA since DMA does not require determination of a specific duplex Tm, so small changes in target sequence would not have a significant deleterious effect.

DMA can also be used with TOCE probes, described in WO2012096523, incorporated herein by reference. Hybridization and extension of an upstream primer in the presence of its target nucleic acid results in cleavage of a downstream hybridized pitcher oligonucleotide to release a tagging oligonucleotide. The tagging oligonucleotide then hybridizes to a labeled probe or catcher oligonucleotide which serves as a template for extension of the tagging region to generate a duplex nucleic acid having a predetermined Tm. Various labeling schemes may be used to support melt analysis of the duplex nucleic acid. For example, extension of the tagging region may cause separation of the quencher and fluorophore of a random coil labeled probe to result in fluorescence. Amplification can thus be detected in real time by detecting an increase in fluorescence as the duplex forms, and melt analysis can be detected as a reduction in fluorescence as the random coil probe reassumes a random coil configuration. Since the catcher oligonucleotide is target-independent and can be designed to have a predetermined Tm, this detection method is well suited for use in DMA.

DMA may also be used with intercalating dyes such as SYBR or EvaGreen. Identification of targets can be achieved through amplification of target regions having different lengths or sequence composition, and thus different Tm values. Following amplification, the reaction mixture can be subjected to increasing temperatures in a discrete melt analysis to measure changes in fluorescent intensity corresponding to double-stranded amplicon or duplex dissociation. DMA is useful in intercalating dye and probe-based detection methods because signals can be detected at discrete temperatures higher than and lower than the predetermined Tm of the duplex of interest, which can be designed to be outside of the Tm ranges that include non-target amplification products such as primer dimers (which are typically lower in Tm than true target duplexes). For example, in a melt analysis non-target spurious duplexes might have Tms in the temperature range of 60 to 75° C. The target amplicon or duplex of interest may be designed to have a Tm of 83° C. In this scenario DMA could be performed at 78° C. and 88° C., either in a bulk reaction or in a dPCR format. This method of analysis would avoid acquiring signals associated with non-target amplification events in a quick and efficient manner that would be superior in specificity compared to a single temperature measurement, and superior in speed and processing to a high-resolution melt analysis.

Although DMA can be applied to non-digital or homogenous assay chemistry methods such as closed-tube or real-time bulk PCR methods, it is particularly useful in digital amplification applications because it provides particular advantages for accurate counting of positive partitions for quantifying the starting concentration of target in the reaction.

Additionally, described herein are various methods for quantifying and improving the quantification of the target nucleic acid in dPCR using various analysis techniques.

A. Methods for Using Controls in dPCR

Strategies for employing controls in dPCR are described for dPCR systems that incorporate sample processing and dPCR into a single instrument and workflow (sample-to-answer) or systems that maintain separation between sample processing and the dPCR workflow. All methods described are aimed at optimizing precision in target quantification using dPCR, particularly dPCR systems that employ melt analysis to identify multiple targets in a single reaction compartment or partition. Methods described herein rely on calibration dyes, probes and control targets to generate reference data sets and standards by which instrument performance can be measured. Tests with these dyes, probes and targets can be performed separately from sample reactions or simultaneously alongside sample reactions to validate system performance including sample processing, optics and thermal control. A preferred embodiment includes control reactions run simultaneously with sample test reactions and control reactions run separately from sample test reactions.

Current dPCR systems do not have the advantage of including multiple controls in a single reaction as contemplated herein because they are limited in multiplexing capability. As such, existing dPCR methods require such controls to be included in separate wells or chips rather than within the sample reaction which can introduce variability between sample and control performance. Likewise since qPCR reactions rely on controls contained within the bulk volume PCR reaction, the ability to include multiple controls is also limited by the degree of multiplexing available.

A set of calibration dyes and probes can be utilized to generate a set of reference data by which instrument performance can be monitored at a suitable frequency. This set of dyes and probes can include system-specific dyes labeled with short oligo sequences to render them soluble in water as well a variety of hairpin probes designed to exhibit a range of melt profiles (melt-calibration controls) for performing appropriate calibrations.

The set of calibration dyes can be used to ensure that the instrument is detecting and reporting the expected fluorescence intensities across all channels. A different calibration dye for each channel can be included in a control sample, and the measured intensities can be compared to previously determined intensities at the lower and upper ends of the desired temperature range (such as 55-95° C.). If any of the measurements deviate beyond a predetermined acceptable range from the expected values, this could signify a problem with the instrument, the reagent mix, or operating conditions. Furthermore, calibration dyes can be used to normalize and/or adjust raw measurement values so that measurements can be properly evaluated against the entire set of reference data (e.g., expected melt amplitudes and temperatures of targets or probes).

In another embodiment, one or more melt-calibration controls having known melt profiles and melt temperatures are included in the reaction mixture or in a separate partition. One method of evaluating melt-calibration controls in dPCR applications is to perform a continuous melt analysis in order to identify melt peaks in plots of the derivative of fluorescence versus temperature. Once the precise observed melt temperature is identified, it is compared to the expected value, and any difference between the observed and expected value is used to apply a temperature correction to all measurements. If desired, more than one melt-calibration control can be included to ensure accurate temperature correction across the entire melt analysis temperature window. However, when performing DMA using melt controls, it may be difficult to accurately determine the scope of any necessary temperature correction using the standard method of determining melt peaks.

To overcome this limitation, melt-calibration controls for use in DMA should be designed to melt over a narrow temperature range bracketing (>90% melted within 5° C.) the measurement temperatures used for the DMA analysis. Since DMA does not measure fluorescence at the Tm for a target-specific probe, having the Tm of the melt calibrator within a narrow range of the DMA measurement temperatures (T1, T2, T3 and T4) ensures that fluorescence of the melt calibrator will be maximally sensitive to fluctuations in system thermals. Fluctuations in fluorescence intensity values compared to reference values derived for the melt calibrators will determine the degree of thermal variability. If the thermal variability is within a pre-determined tolerance specification, the melt analysis can be considered complete. If, however, the melt calibrator values suggest variability in the thermal performance, melt analysis can be repeated at appropriately adjusted temperatures or an appropriate correction factor may be applied. In order to most accurately quantify the temperature fluctuation, it is important to ensure that the minimum and maximum fluorescence intensities determined for a particular channel match the expected intensities (reference case) for that channel. These melt-calibration controls can be evaluated either independently as part of system maintenance and calibration, or they may be included as on-board controls and processed alongside all samples if the desired number of melts in a channel or across channels are reserved.

It is optimal to measure the melt-calibration control simultaneously alongside the sample measurement as individual experiment conditions can cause results to deviate from expectations. For instance, the concentrations of oligonucleotides and salts can alter melt temperatures by as much as 10-20° C. in extreme cases. In one method, a melt-calibration control is included whose expected Tm is known. To avoid confusion with the targets being tested, the melt-calibration control can be selected so that the illumination channel and emission wavelength region will not coincide with the emission wavelengths of the targets. As an example, a FAM-labeled control with an expected melt temperature of 84.1° C. could be included with the analyte being tested, or it could be measured separately. An acceptable range could be identified, such as +/−2.5° C., or 81.6 to 86.6° C. Then, if raw melt data (obtained, e.g., by taking measurements from 55 to 95° C. at 0.5° C. increments) shows a melt peak at a set-point temperature of 83.1° C. in a plot of the negative derivative of fluorescence versus temperature, one can calculate the temperature correction, $\Delta T_{corr}$, required to shift the set-point temperatures as needed. In the example, subtracting the expected temperature from the set-point temperature yields a temperature correction of $\Delta T_{corr}$=83.1-84.1° C.=−1.0° C. By adjusting future set-point temperatures by the temperature correction of −1.0° C., the expected melts should occur at the expected temperatures. If the control were repeated but this time accounting for the temperature correction, for our data point at 84.1° C., our calculated temperature correction dictates that for our set point, we should use 84.1° C.+$\Delta T_{corr}$=84.1-1.0=83.1° C., which should then yield a melt peak at our desired 84.1° C. data point.

If desired, more than one melt-calibration control can be included to ensure not only proper temperature correction but also proper temperature difference between expected melt peaks. For example, a first melt-calibration control could be a FAM-labeled control oligonucleotide with an expected melt temperature of 84.1° C., and a second melt-calibration control could be an AP-593-labeled oligonucleotide with an expected melt temperature of 71.0° C. Since we expect a temperature difference of 13.1 C, any substantial deviations from that value between observed melt peaks could signify a problem in the system, such as defective or improper ramping of temperatures—for example, a loose wire could be delivering less current than necessary to the thermo-electric heating/cooling unit, thereby delivering less heat and lower temperatures than expected from a given set point.

An alternative method for thermal calibration relies on the use of a well-characterized, temperature sensitive fluorescent dye. Exemplary dyes for this use are Rhodamine and AP662. These dyes display robust, reproducible temperature-dependent fluorescence across the melt analysis range. Deviation from the expected dye performance is used to adjust system thermals accordingly.

Even for the same input target concentration, actual concentration measurements may vary for a variety of reasons, including: variability in the extraction and purification process; variability in operating conditions; dependence of observed melt temperatures on concentrations of oligonucleotides and/or salt concentrations; variability in equipment efficiency. For these reasons, further embodiments of the present disclosure provide methods for including and using controls to determine how to compensate or correct measured input target values for optimal comparison and interpretation of results. In general, these methods comprise the use of nucleic acid controls included in various stages of sample treatment.

One method comprises including a sample processing control having a reproducible, known concentration in the reaction mixture to determine sample preparation efficiency. By comparing the measured final concentration of the control to the known input, an appropriate correction can be applied to the concentration of unknown analyte calculated for the sample. This correction can be obtained by dividing the expected input value of the control by the measured value obtained in the assay to obtain a multiplier value. The multiplier value can be applied to the initial value obtained for each analyte after Poisson correction, to obtain a sample preparation efficiency corrected value that will more accurately reflect the true concentration of each analyte in the patient sample. The sample processing control may be added at the same stage as the sample is typically added. It may be added manually or it may be added mechanically by an automated process from a designated well in a cartridge for example. It may be in liquid form or in a dried down or lyophilized state. Alternatively, an endogenous nucleic acid control that is expected to be at a relatively stable concentration for the sample type of interest may be used.

Additionally, the method can include the addition of an amplification control comprising an oligonucleotide target sequence and corresponding, target-specific probe in the PCR master mix (post sample processing) to characterize the distribution of positive and negative partitions for a known concentration of control target. By addition of a control target at a known concentration, the expected fluorescence intensity of positive and negative partitions may be determined, and used to set preliminary thresholds for classifying unknown targets. Further, preliminary thresholds may be used as an initial classification threshold which is subsequently adjusted using manual thresholding or algorithm-based methods. In any case, an exemplary ideal concentration to set the sample processing control or the amplification control would be one having a lambda (expected copies per partition) value of 1.59. At this value, digital PCR achieves the highest precision in quantification (Majumdar et al., Digital PCR Modeling for Maximal Sensitivity, Dynamic Range 2 and Measurement Precision, *PLOS One*, 2015) which means variability due to sample processing would be most isolated from the inherent variability of the Poisson distribution. These controls may be included at a single Tm in a single fluorescence channel or across all fluorescence channels. In the former case, the previously described verified set of data using calibration dyes will allow the user to extrapolate single fluorescence channel data to other fluorescence channels.

Alternatively, the distribution of positive and negative droplets and their intensities at the measurement temperature extremes for an unknown target can yield valuable information for optimal interpretation of results. For example, assuming at least one partition will test negative for all targets, the fluorescence intensity of target-negative partition(s) can be used as an internal control. The average intensity for target-negative partition(s) may be determined and compared to a reference or historical case. Differences between the measured and historical value can be indicative of a change in operating conditions, sample composition, or equipment issues. The fluorescence intensity of target-positive partitions can similarly be compared to a reference or historical case to evaluate system performance.

Images may show some degree of variability due to non-uniformity in illumination or measurement of fluorescence across the two-dimensional array of partitions. This variability will have a larger impact when multiple images are stitched together to create an aggregate image of all partitions for a single sample. In one method to correct for this variability, an image acquired after partitioning but before nucleic acid amplification may be used to normalize images acquired post-amplification. The average partition intensity across all partitions in the pre-amplification image is calculated and divided by the average intensity in individual partitions. The resulting partition-specific ratios can be used to normalize the intensity across subsequently acquired images to account for any illumination or measurement-induced non-uniformity. The same strategy may be used for each channel in the final instrumentation embodiment.

In another embodiment, rather than relying on the inherent fluorescent signal of the included probes pre-amplification, a passive reference dye is used to correct for non-uniformity of fluorescence. The internal reference dye can be used as a channel-agnostic intensity normalization factor for all fluorescence measurements much as passive reference dyes are used in existing real-time or quantitative PCR instruments. Additionally, in the droplet embodiment, the passive reference dye can be used to aid in droplet identification since probe-based fluorescence measurements will be variable relative to amplification state and temperature depending on probe Tm.

In certain dPCR systems where multiple samples are processed in parallel, it would be possible to reserve a single sample well to include the types of controls described herein. In one method, a well/partition in a microfluidic device, such as described in U.S. Pat. No. 9,039,993, can be reserved for fluorescence normalization and thermal calibration. Much as for internal controls included in sample wells, this well may contain a passive reference dye that can be used as a channel-agnostic intensity normalization factor for all fluorescence measurements. One or more melt calibrators can be included to account for any thermal variability. The measured peak of this or these melt calibrators can be used for thermal calibration through the determination of the difference between the known melt peak of the calibrator(s) and the measured melt peak of the calibrator(s). A simple translation along the temperature axis can account for small day-to-day variability.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A method of Normalizing Images to Improve Partition Classification Using an Image Acquired Pre- or Post-Nucleic Acid Amplification In real-time PCR, well-to-well normalization using a passive reference dye such as ROX minimizes variability that arises due to variations in optics and reaction volume. A similar normalization scheme would be beneficial in array-based digital PCR, however the inclusion of a channel devoted to a single passive reference dye would ultimately limit the multiplex capability of a system. In the described embodiments, fully denatured probes in a selected fluorescence channel may serve as an internal passive reference dye in each partition. In one example, an image is acquired at a temperature at which all probes are denatured (e.g. 95° C.) and thus exhibit maximal fluorescence. This 95° C. image can be acquired after partitioning but prior to nucleic acid amplification or during the course of melt analysis after nucleic acid amplification. Partitions are identified in the image, and the average pixel intensity per partition is determined. All partition average intensities acquired in the melt series at various temperatures can be normalized to the corresponding 95° C. partition average intensity to account for partition-specific variations by subtracting the 95° C. average intensity from the intensities measured during melt analysis.

FIG. 8 showcases the effect of this normalization on discrete melt data generated from partitions containing a single probe. FIG. 8A shows a raw data image taken at T1 and FIG. 8B shows the same data normalized using a 95° C. image. As can be seen, contrast is enhanced between positive and negative droplets in the normalized image. Corresponding intensity histograms shown in FIGS. 8C and 8D illustrate that normalization results in clustering into the two expected populations (pixels associated with dark droplets and pixels associated with bright droplets). Prior to normalization, three distinct peaks are visible (FIG. 8C). Without being bound by theory, we posit that one population is associated with dark droplets and two populations are associated with bright droplets that vary in brightness due to non-uniformity of illumination and fluorescence collection. The positive effect of normalization is further demonstrated in the 1D amplitude plots shown in FIGS. 8E and 8F. In panel E, it may be difficult to determine a suitable threshold for classification of a droplet as positive or negative as a significant number of droplets lie between the 2 discernible populations. After normalization however (FIG. 8F), many fewer droplets fall between the two discernible populations.

Example 2

Figure 9B:
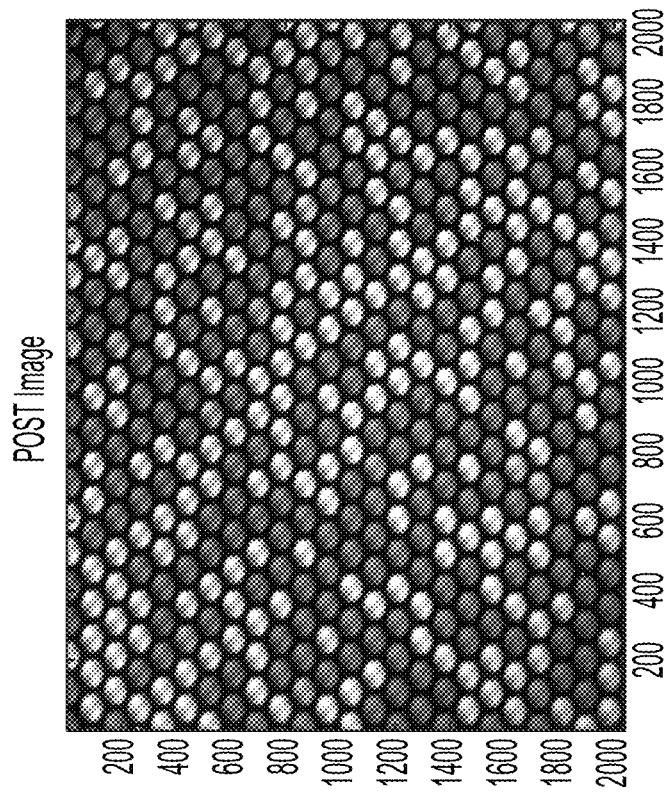
FIG. 9: Example of using pre-amplification images to establish preliminary thresholds. Pre-amplification image of partitioned sample (FIG. 9A); Post-amplification image of partitioned sample (FIG. 9B); Average droplet intensity histogram (FIG. 9C) from pre-amplification (dark grey bars) and post-amplification (white bars) images; 1D amplitude plot (FIG. 9D) from pre- and post-amplification images (black and white respectively) showing average droplet intensity. In both C and D, the gray lines represent 3σ from the mean of the pre-amplification average intensity.
Figure 9A:
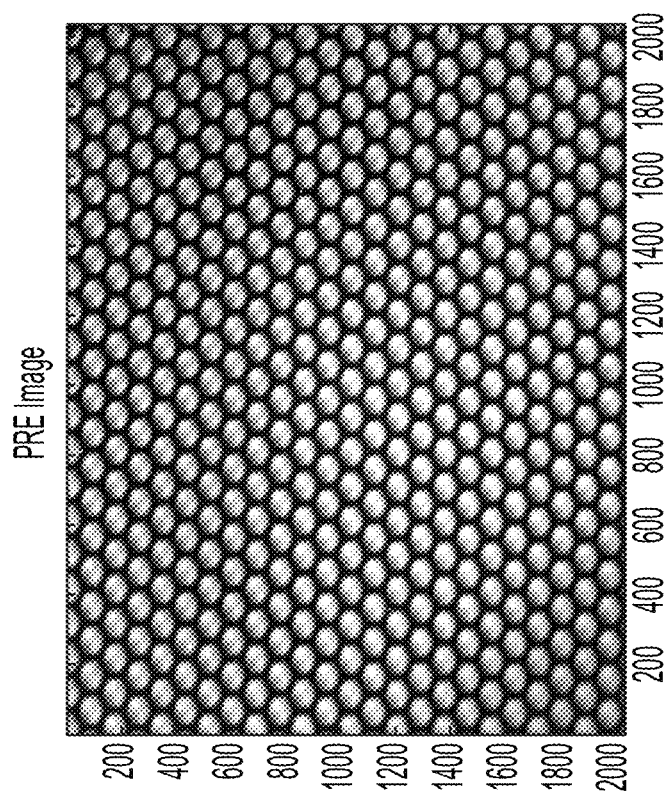

A method of Establishing a Preliminary Cutoff for Negative and Positive Partitions Using an Image Acquired After Compartmentalization but Prior to Nucleic Acid Amplification Correct classification of negative and positive partitions is needed for accurate quantification using digital PCR. Existing dPCR methods rely on endpoint imaging alone to classify partitions as positive or negative for target nucleic acid(s). In the present method, an image of the partition array is acquired after partitioning but prior to nucleic acid amplification (FIG. 9A). At this stage, each partition should theoretically have the same uniform fluorescent intensity originating from target specific probe(s). However, in practice, average intensity values of different partitions will follow a distribution about an average or expected value with some variance or standard deviation. The average intensity value for a compartment is calculated as previously described.

Figure 9D:
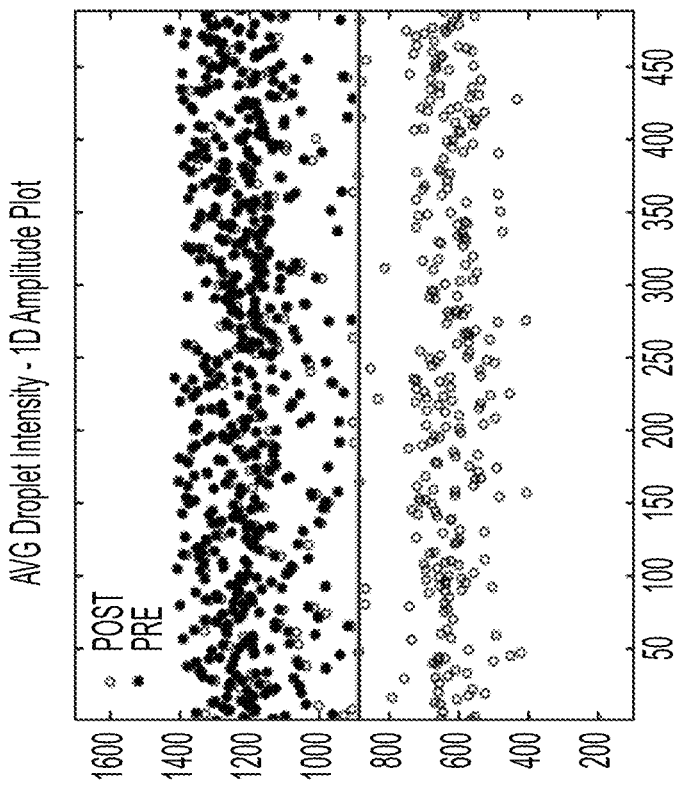
Figure 9C:
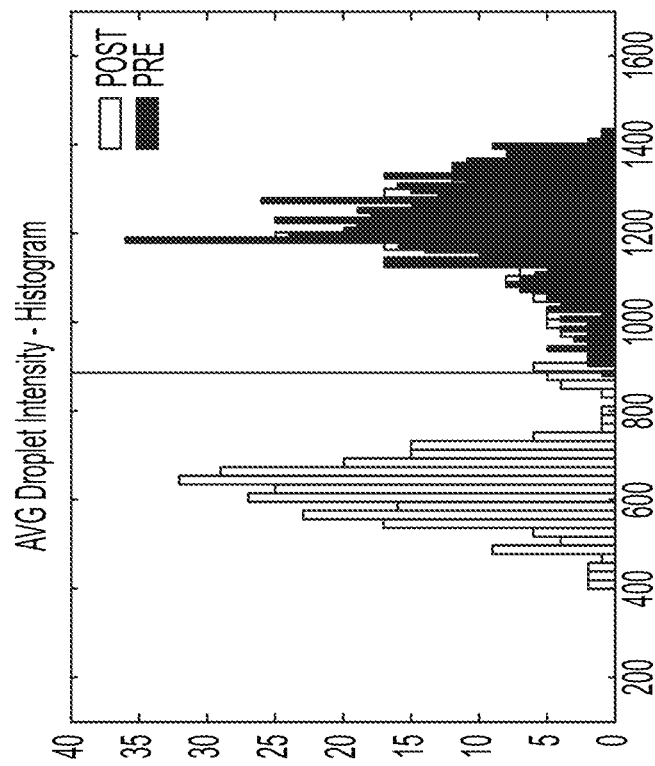

These average intensity values across the entire population of partitions are grouped together and the average (expected value) and standard deviation (square root of the variance) is calculated (FIG. 9C; gray bars). Using the now defined standard deviation of this distribution, a threshold for classification of partitions as positive or negative is set at the average intensity value across all pre-amplification partitions less three (gray line in FIGS. 9C and D) standard deviations of the average pre-amplification partition population's average intensity value. This initial threshold setting can form the basis for iterative threshold refinement post-amplification. FIG. 9B shows an image of droplets post-amplification. Bright droplets are negative for the target and dim droplets are positive for the target. In the overlay of intensity distributions (FIG. 9C) and the intensity event plot (FIG. 9D), a high degree of overlap in the negative populations demonstrates the feasibility of initial threshold setting in this manner. Additionally, in an embodiment where classification algorithms such as k-means clustering are used to identify positive and negative partitions, the data acquired through this image may be used as a training set for the classification algorithm. In order for this pre-classification work, the pre-amplification and post-amplification images should be acquired at the same temperature. Note that in detection schemes in which probe signal decreases as target amplification proceeds, partitions with intensity values that lie above the threshold post-amplification are classified as negative droplets. Partitions with intensity values that lie below the threshold after amplification are classified as positive partitions. In signalling schemes that use a DNA-intercalating dyes or probes that are unquenched in the presence of target, fluorescence intensity increases as amplification of target proceeds, so partitions below the threshold are classified as negative while partitions above the threshold are classified as positive.

Example 3

Methods for Correcting Post-Amplification Images for Temperature-Dependent and Light Dose-Dependent Changes in Fluorescent Intensity of the Probes After nucleic acid amplification, melt analysis to identify specific targets is performed over a temperature range of 55° C. to 95° C. The intensity of fluorescence of some fluorescent dyes has been shown to be variable within this temperature range. Additionally, some dyes, such as FAM (a derivative of fluorescein) are known to exhibit photobleaching as a result of repeated light exposures such as those sustained during multiple image acquisitions (Song et al., Photobleaching Kinetics of Fluorescein in Quantitative Fluorescence Microscopy, *Biophysical Journal*, 68, 2588-2600 (1995)).

To correct for such variability, a series of images can be acquired subsequent to partitioning but prior to nucleic acid amplification at temperatures ranging between 55° C. to 95° C. Preferably, a minimum of 3 images are acquired at equally spaced temperature intervals across the entire melt profile temperature range for each wavelength used in melt analysis. The average intensity in individual partitions is determined using one of the methods described previously (entire partition vs. an ROI) and plot on the y-axis of a graph against the temperature at which the image was acquired. This collection of data points is fit with an appropriate model (linear or exponential) based on a priori knowledge about the probe's sensitivity to both temperature and light using least-squares regression. In the case of probes where light sensitivity dominates and photobleaching is a significant source of intensity loss, an exponential model or a mixed model of linear and exponential may fit the data best. In the case of probes where temperature-dependence dominates and photobleaching is minimal, a linear model may fit the data best. The goodness of fit is determined by either the standard error of the regression or the coefficient of determination, $R_2$. Important metrics obtained from these fits can include the slope, time constant and/or the y-intercept. A unique set of metrics is determined for each fluorescence channel present.

Following nucleic acid amplification, a series of melt images is acquired. Prior to melt analysis (i.e. assessment of the melt profile to determine the presence of probe-specific targets), the average intensity determined for each individual partition over the entire melt profile temperature range is corrected for any temperature- and light dose-dependent losses specific to each fluorescence channel. Specifically, the linear or exponential decay of fluorescent signal is corrected for in the series of post-amplification melt images by subtraction of the fit obtained from pre-amplification data from the post-amplification melt profile, to generate a corrected melt profile. Further analysis to identify and quantify the presence of probe-specific targets is now carried out using the corrected melt profile. Alternatively, the correction for temperature- and light dose-dependent fluorescent loss is applied pixel-by-pixel to the entire image prior to calculation of the average intensity in an individual compartment or droplet.

In another alternative method, pre-existing datasets are used to correct for temperature- and light-dose dependent fluorescence loss. As previously mentioned, probe intensities can vary in a linear or non-linear fashion, or even through a combination of linear and nonlinear relationships, over the course of melt measurements. For example, in Song et al. (Photobleaching kinetics of fluorescein in quantitative fluorescence microscopy, 1995. *Biophysical Journal*, 68(6), 2588-2600. doi: 10.1016/s0006-3495(95)80442-x), fluorescein intensity was shown to have a double-exponential photobleaching behavior in oxygen-poor conditions, while a single-exponential behavior was seen in oxygen-rich environments. To correct the intensity slopes for any temperature dependence and/or photobleaching, data from control samples is used, where the most appropriate curve is fit to control data (for example, a double-exponential curve fit) and the fitted curve from the experimental data is subtracted or normalized to control values. Alternatively, if sufficient negative-result partitions exist after amplification, they can act as controls and be used for curve-fitting purposes to adjust for slope changes due to temperature- and light-dependent fluorescence changes.

Figure 10:
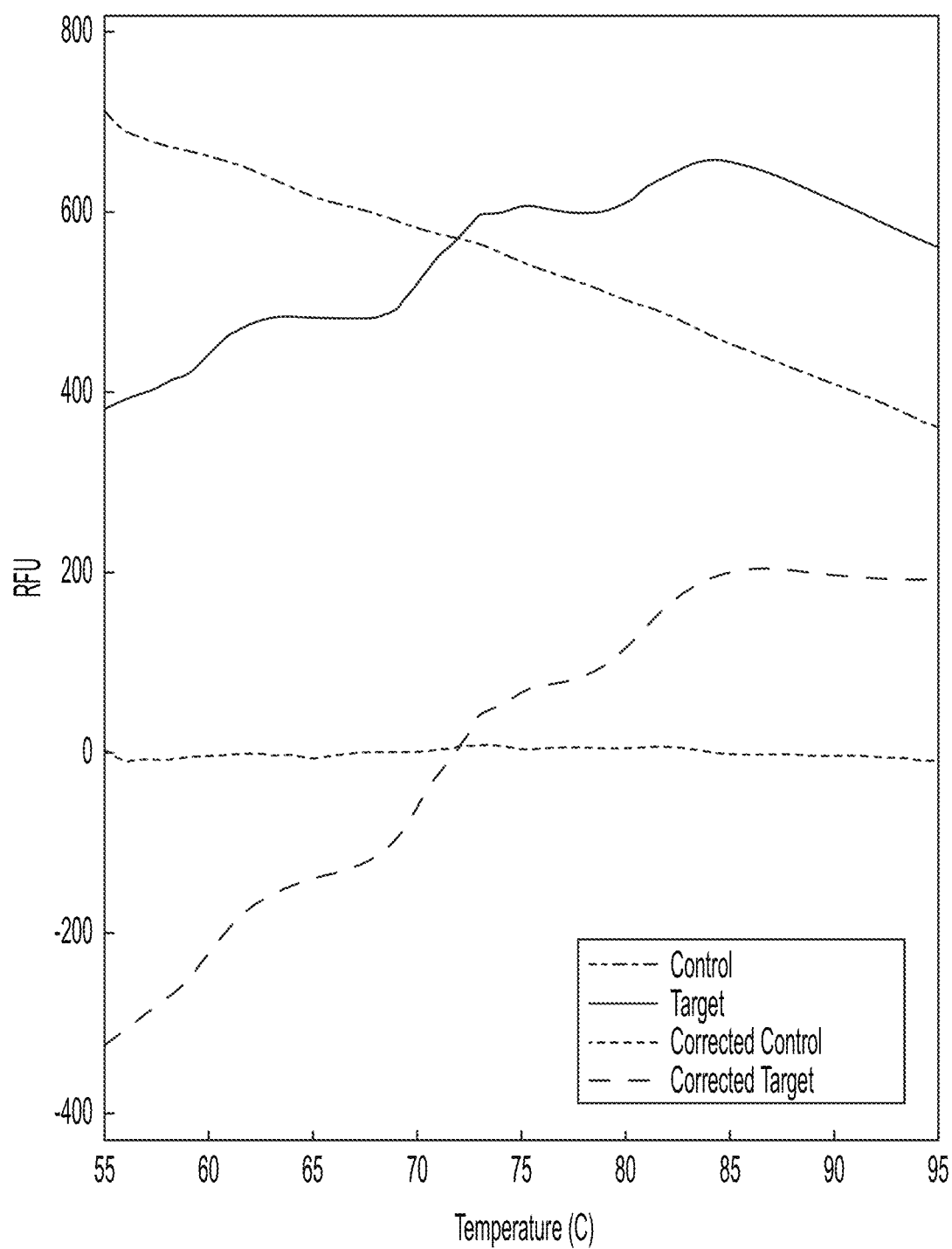
FIG. 10: Example of correcting for temperature- and light dose-dependent changes in fluorescence intensity of probes. Plot of fluorescence v. temperature using raw, uncorrected data from a partition having 3 targets and 3 probes with distinct Tms (upper, solid trace) and from a partition having 0 targets and 3 probes (upper dashed trace); Plot of corrected fluorescence v. temperature data from the same sample is shown in the lower half of the figure. The correction is determined from the linear decay observed for the negative partition that results from fluorescence photobleaching and temperature-dependent changes in fluorescence.
Figure 11A:
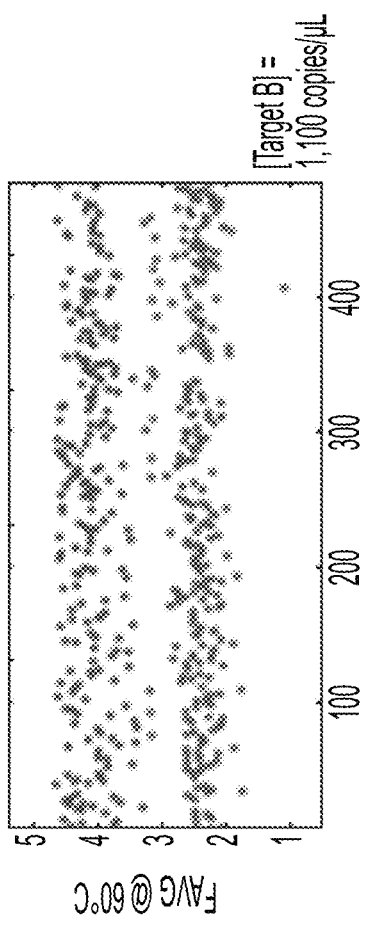
FIG. 11: Singleplex Continuous Melt Analysis. Left: Fluorescence v. temperature plots from images taken at 1° C. intervals from partitions of a dPCR reaction containing a single-target sample and detected using a cleavable probe; A: raw, uncorrected data; B: 1D amplitude plot corresponding to A showing signal intensity per partition at 60° C.; C: data shown in A normalized to fluorescence at 95° C. to correct for system-induced partition variability; D: 1D amplitude plot corresponding to C showing signal intensity per partition at 60° C.; E: data shown in C normalized to correct for light and temperature-dependent fluorescence variations of probes; F: 1D amplitude plot corresponding to E showing signal intensity per partition at 60° C.; G: Inverse derivative of data shown in E showing Tm for target-specific probe in each partition; H: 1D amplitude plot corresponding to G showing integrated signal intensity across the target-specific melt window. The expected number of copies per partition is calculated using Poisson statistics and extrapolated to number of copies of target per µL.
Figure 11B:
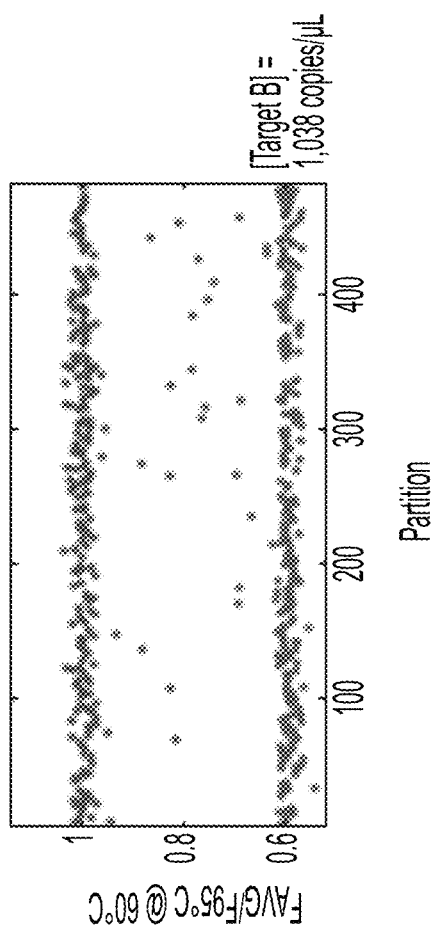
Figure 11C:
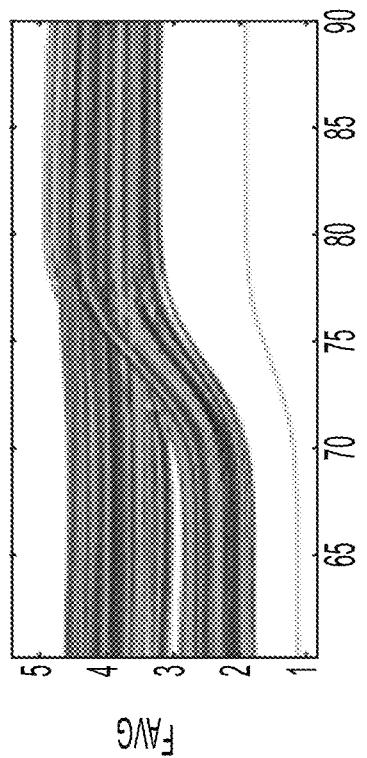
Figure 11D:
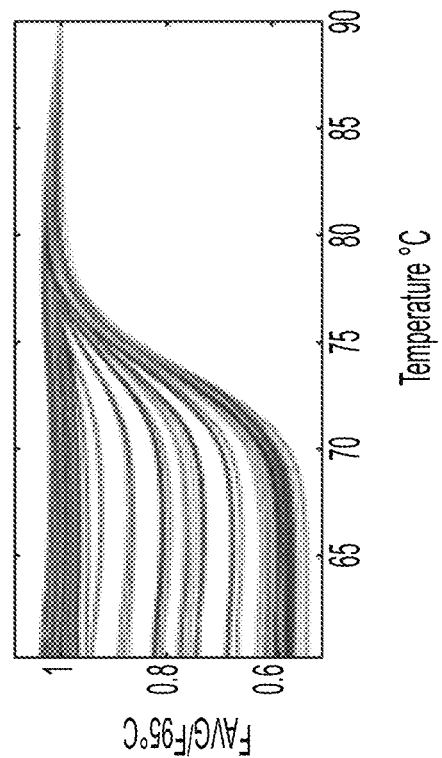
Figure 11E:
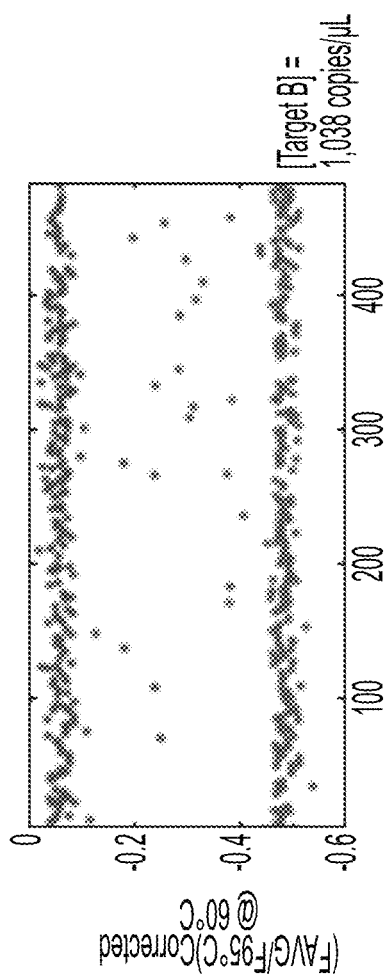
Figure 11F:
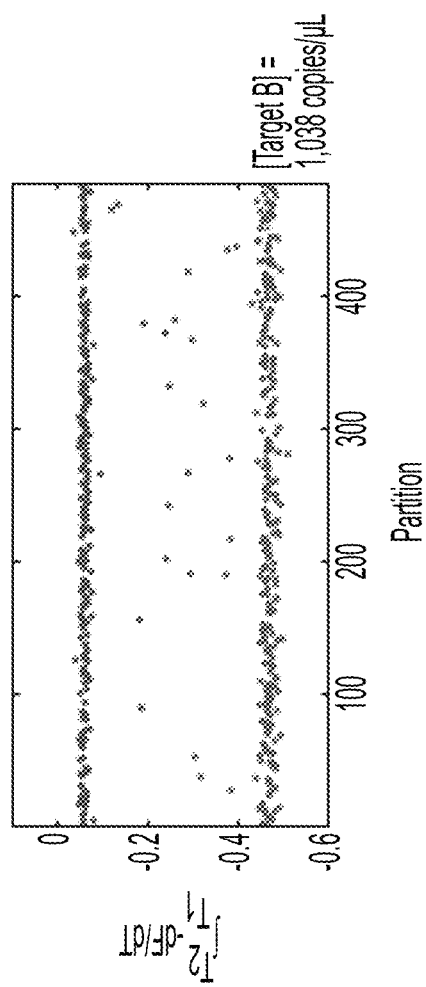
Figure 11G:
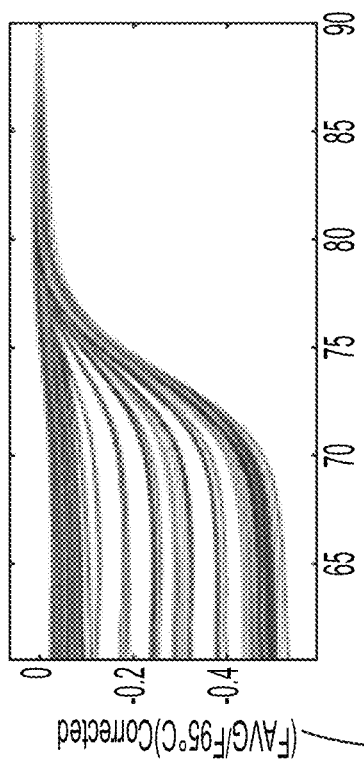
Figure 11H:
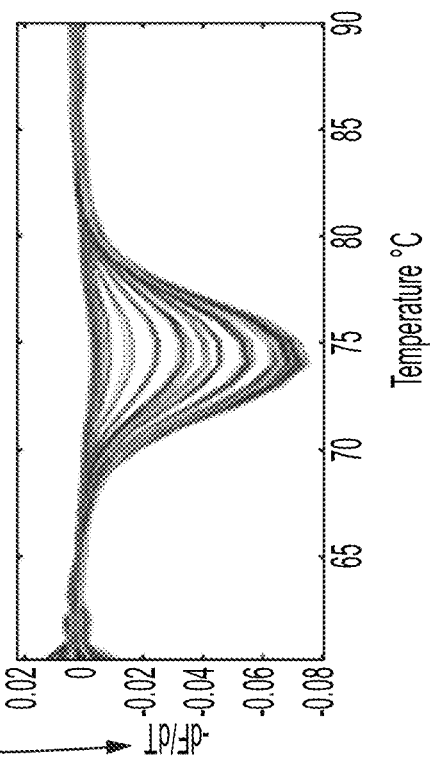

FIG. 10 illustrates how fluorescence intensities measured from a negative (target-free) control partition can be used to compensate/correct for temperature-dependent and/or light-dose-dependent fluorescence variations in a test sample.

FIG. 10 shows the melt curve generated from raw data collected for a sample with three target-specific probes, each of which have distinct melt temperatures (Target) and a negative partition (Control), and corrected melt curves for the sample (Corrected Target) and negative control (Corrected Control). It is clear from the uncorrected (raw) data from the Control that a linear decay in fluorescent intensity occurs with increasing temperature in the negative control. Lower than expected fluorescence intensity is also noticeable over the last 10° of the positive sample melt profile, where the expected increase in RFUs is not detected. As can be seen from the uncorrected data, discrete sampling without correction would result in a negative call for target 3 as there is no measurable fluorescent intensity increase between the third and fourth data points (highlighted on the graph by large dots). The expected step-wise increase in intensity for each melt event is masked by the temperature-dependent decrease in intensity as a result of fluorescence bleaching. However, following the application of a linear decay correction (and a translation along the Y-axis for the purpose of viewing in comparison here), the discrete melt events for all 3 probes are readily detectable.

Example 4

Methods to Determine the Full Range of Values for Total Fluorescence Change for Initial Partition Classification Post-amplification, an image is acquired first at the lowest temperature (T1) in the melting analysis temperature profile. Corrections for the temperature- and light-dose dependent decay in fluorescence must be applied to all images using one of the methods described in Example 3. Average or integrated partition intensity in the T1 image is then normalized by either an image at T4 obtained pre- or post-thermal cycling or an image obtained at T1 prior to thermal cycling as described in Example 1. In the case of static array dPCR, correction and normalization can be applied on a pixel-by-pixel basis across the whole image or on the average or integrated intensity within individual partitions. In the case of droplet dPCR, if the droplets move during image acquisition, it may be necessary to first identify and correlate droplets from the two images prior to determining the ratio of partition fluorescence on a droplet-by-droplet basis. The following analyses can be performed using the average intensities determined through correction and normalization of the T1 image or by using the difference between the corrected and normalized T1 and T4 images as demonstrated in Equation 5.

$$\Delta F = I_{High} - I_{Low} \quad \text{Equation 5}$$

Figure 13E:
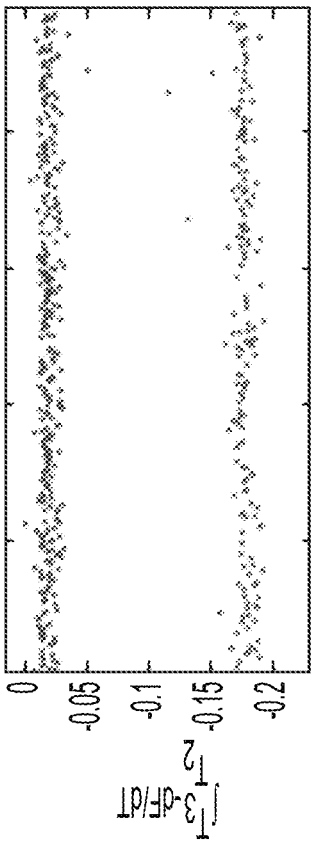
FIG. 13: Multiplex Continuous Melt Analysis. Left Panel: Fluorescence v. temperature plots from 35 images taken at 1° C. temperature intervals for a sample containing 3 targets and 3 probes with distinguishable Tms. From top to bottom: A: Average fluorescence per partition v. temperature during melt analysis; C: Average fluorescence per partition normalized to correct for system-induced partition variability; E: Average flourescence per partition from C further corrected for light- and temperature-dependent fluorescence decay; G: Inverse derivative plot of E showing 3 distinguishble probe Tms; Right panels: B: 1D amplitude plot of average intensity per partition at 57° C. normalized to 95° C. image; D, F, & H: Plot of the integral of the derivative for each target-specific melt window.

A histogram or 1D amplitude plot of the partition specific, average intensities of either the corrected and normalized T1 image or the calculated $\Delta F$ values informs the initial classification of partitions as containing 0, 1, 2 or 3 unique targets. Negative partitions containing no target molecules will show little to no change in fluorescent intensity (i.e. $I_{AVG}=1$ or $\Delta F=0$). Partitions containing all three targets will show the greatest change in fluorescent intensity. Partitions containing 1 or 2 targets will show intermediate changes in fluorescent intensity with 2-target partitions showing a greater change in fluorescent intensity than partitions containing a single target. An example of a 1D amplitude plot demonstrating initial droplet classification in a 3-plex assay in a single channel is shown in FIG. 13B.

Assuming all probes are included at equivalent concentrations in a three-plex reaction, the distribution of partition intensities from the dissociation image is centered around intensities of 0 or 1, $\Delta RFU_{max}$, $(1/3)*\Delta RFU_{max}$, $(2/3)*\Delta RFU_{max}$, where $\Delta RFU$ specifically refers to $\Delta RFU_{95-56}$. For a given probe in a well-characterized assay, the $\Delta RFU_{max}$ should be a consistent value, and initial thresholds may be set to classify partitions based on a reference data set. These thresholds may then be further refined manually or using algorithm-based means such as k-means clustering. For example, a method referred to as definetherain that uses k-means clustering has been made available by a third party through a web interface (definetherain.org.uk) for application to digital droplet data obtained using Bio-Rad systems. There are a variety of additional classification or cluster analysis algorithms that can be applied to partition classification.

Partitions containing no targets or all three targets may be classified using the previously described process. These partitions can henceforth be excluded from further analysis (melt acquisition or data analysis) for simplicity. Eliminating these partitions from further analysis reduces the number of male analysis images required to be acquired to further reduce the time required for image acquisition and data analysis. However, if three target-specific probes are detectable in a single channel, and a partition contains only a single target, melt analysis may be used to distinguish the presence of the particular target within a partition.

The methods described for performing initial partition classification can also be applied to the use of a passive reference dye for normalization. The $\Delta F$ value calculated in Eq 1 is normalized by the passive reference dye signal much in the way that Rn and $\Delta Rn$ are calculated for real-time or quantitative real-time PCR. Rn is the ratio of measured fluorescence and passive reference dye fluorescence while $\Delta Rn$ is Rn after baseline correction. The use of a passive reference dye does not eliminate the need to account for temperature- and light dose-dependent fluorescent intensity loss over the course of melt profile generation as the passive reference dye only accounts for this loss in a single channel and losses across channels are not expected to be uniform. Likewise, there may be variability in the temperature- and light dose-dependence of different fluorophores.

Example 5

Single Plex Continuous Melt Analysis vs. Discrete Melt Analysis

Singleplex Continuous Analysis

Singleplex PCR was performed on a target, referred to herein as target B, and detected using a cleavable probe as described in U.S. application Ser. No. 14/822,288 having an expected Tm of 74° C. PCR samples were prepared in a buffer containing: 10 mM Bis-Tris propane (pH 9.1), 0.3 mg/mL BSA, 100 µM dNTPs, 90 µM DTT, 1 µM Dabcyl-diGTP, 10 mM Tris Base, 2.5 mM MgCl$_2$, and 50 mM KCl. Enzymes included in the reaction include TiTaq (Clontech) at 4× and Hot Start RNase H2 at 16 mU/uL (Takara). Forward primer B (for target B) (5' GCAAGATACCATT-TATCAATGAAG 3'; SEQ ID NO: 1) was included at a concentration of 480 nM, reverse primer B (5' GGTGT-CAATTTTCTTATATCATAAT 3'; SEQ ID NO: 2) at a concentration of 120 nM and probe B (5'/56-HEX//iMe-isodC/TTCTCTTCTCTTTCATTCACATAACGCCAAA/ iSpC3/AAACCCGTTATGTrCCTCC AGTTCCCATAT-TTG/3SpC3/3'; SEQ ID NO: 3) at a concentration of 300 nM. Ultramer B (5' ATGACTAAGCAAGATACCATTTAT-
CAATGAAGAAGAGTTTATTGTAGAGAAAATAA
GAGTAATGTTTGTCCAACATTAACTGCAAATATGG-
GAACTGGAGGACATAACGTTCC ATTAATAAAGGA-
TAATTATGATATAAGAAAAT-
TGACACCAGAAGAATGTGTGGCAT
TTCAAGGTTTTCCTTCAGAATTTCAATTC 3'; SEQ ID
NO: 4) was included at an expected concentration of 907
copies/uL. Template-free control reactions were included to
ensure that the assay performed as expected, however data
is not included here. Samples were partitioned into multiple
partitions using a QuantStudio 3D (QS3D) loader and v2
digital PCR chip (14.5 µL per chip) and sealed according to
the manufacturer's instructions for continuous melt analysis.

Partitioned reactions were thermal cycled on a ProFlex
thermal cycler at an 11° incline (per QS3D manual) to end
point using the following thermal cycling protocol: 96° C.
for 10 minutes, 45 cycles of 57° C. for 2 minutes and 98° C.
for 30 seconds, and finally a 5 minute hold at 57° C.
Following thermal cycling, melt analysis was performed
using a LabView controlled custom melt reader consisting of
a thermoelectric cooler (TEC) and imaging apparatus. For
continuous melt analysis, the chip was heated from 60° C. to
90° C. in increments of 1° C. and images were acquired at
each temperature using excitation (511/55 nM) and emission
filtering (549/15) appropriate for HEX. Images were ana-
lyzed in Matlab using custom software. A built-in circle
finding algorithm based on a Hough transform was
employed to identify individual partitions and average inten-
sity values were determined across the melt profile (on a per
image basis). In a singleplex assay, an endpoint image taken
at the self-annealing temperature of the probe is sufficient to
classify partitions as positive or negative for the target. FIG.
11 shows raw fluorescence data from melt analysis (A)
alongside a plot of the average intensity per partition at the
probe annealing temp (B). Classification and subsequent
calculation of partitions as positive or negative for the
template is applied to Equation 1 below to determine the
average number of template copies/partition, and thus the
concentration of template present in the reaction. This
classification can be done manually or using a classification
algorithm. k-means classification results in a determination
of 1,100 copies/µL, compared to the expected 907 copies/
µL. Manual classification is expected to yield variable
results depending on the user due to the presence of con-
siderable "rain". Normalizing individual partition melt pro-
files to the average partition intensity measured at 95° C.
reduces rain and simplifies manual classification of positive
and negative droplets (FIGS. 11. C&D). An additional
correction can be applied to account for temperature- or light
dose-dependent fluorescence decay across the melt profile
(FIGS. 11 E&F), though the impact of this correction will be
dependent on whether the fluorescent dyes used in the
experiment exhibit such decay. The derivative of the melt
profile can also be used to quantify template presence. The
inverse derivative of the normalized melt curve is calculated
and the intensity is integrated across the melt peak. Inte-
grated partition intensity per partition is shown in FIGS. 11
G&H. As before, manual or algorithm-based classification
can be applied to determine the number of template copies
present in the reaction. Note that in the singleplex case, the
quantification of template using k-means classification is
identical for melt vs end point analysis and application of the
correction factors discussed above appears to yield a value
(1,038 copies/µL) closer to the expected value of 907
copies/µL. In a multiplex assay, the endpoint image will only
be sufficient to determine the number of unique targets
present in a given partition (0, 1, 2, or 3), however melt
analysis will be necessary to identify which specific targets
are present.

Singleplex Discrete Melt Analysis

Sample reactions were prepared, digitized and thermal
cycled as described previously for continuous melt single-
plex PCR. Melt images were acquired at a temperature lower
than the expected Tm for the probe ($T_1$=67° C.) and at a
temperature higher than the expected Tm for the probe
($T_2$=78° C.), and the average intensity of each partition was
measured (FIG. 12A) at each temperature. Images were
normalized relative to an image acquired at 95° C. (FIG.
12C) and the ratio of $T_2/T_1$ was determined (FIG B).
Partitions were classified using k-means, and the target
concentration was determined to be 1,050 copies/µL.

It is evident from the comparison of these results that
discrete melt analysis sufficiently substitutes for the con-
tinuous melt analysis. In the former case, an input copy
concentration of 1,050 copies/µL was calculated compared
to 1,038 copies/µL, a difference of only 1.2%, for discrete
melt analysis.

Example 6

Multiplex Continuous VS Discrete Melt Analysis

Multiplex Continuous Melt Analysis

Continuous melt analysis was used to determine the
presence of multiple targets in a sample. Three targets, (A,
B and C), with corresponding probes having Tms of 63, 74
and 85° C., respectively, were included in each reaction.
Samples and amplification buffers were prepared as
described above. Forward primers $A_F$ and $C_F$ (5' GTGGAG-
GATGACACTTTTCG 3'; SEQ ID NO: 5,5' ATTGAATT-
GAGAGAACTGTTAGATA 3'; SEQ ID NO: 6), reverse
primers AR and CR (5' ATTCCTTAGGTACCGTCAGA 3';
SEQ ID NO: 7, 5' CAACAAAGTTAAAGCTAGTGTTTAG
3'; SEQ ID NO: 8) and probes Ar and Cr (5'/56-HEX//iMe-
isodC/ATATATATATATATAAGAATTCTGCCAAAA/
iSpC3/AAAACCCAGAATTCTTrCC
CTAAGAAAAGGAGTTTACG/3SpC3/3'; SEQ ID NO: 9,
5'/56-HEX//iMe-isodC/CCTCCCCTCCCCTCCCCTT-
CACCATCCAAA/iSpC3/AAACCATGGTGArUCAATC
CTTAACACTGCTTT/3SpC3/3'; SEQ ID NO: 10) for tar-
gets A and C respectively were included at the same con-
centrations described for target B along with the previously
described primers and for probe for target B. Likewise, two
additional templates (A and C) were included (5'
CCCTGACGCAGCAACGCCGCGTGGAG-
GATGACACTTTTCGGAGCGTAAACTCCTTTT
CTTAGGGAAGAAT-
TCTGACGGTACCTAAGGAATAAGCACCGGCTAA
CTCCGTGC 3'; SEQ ID NO: 11, 5' ATGCTAATTA-
CAAAAACAGGATTGAATTGAGAGAACTGTTAGA-
TAAAAACCTGTTT AAAGCAGTGTTAAGGATTGAT-
CACCATCCCAATGAAGATGATCTAAACACTAGCTTT
AACTTTGTTGAAGAAAGCTATGTAGCTTGT 3'; SEQ
ID NO: 12). Target A was included at a concentration of 770
copies/µL, target B at 453 copies/µL and target C at 775
copies/µL. Samples were partitioned, thermal cycled and
melted as described previously. Images were analyzed using
the same custom software to determine the average signal
intensity in a partition over the full range of melt tempera-
tures. FIGS. 13A,C,E&G, represent melt curves for raw data
(A), 95° C. normalized data, (C) temperature and fluores-
cence decay-corrected data (E) and the melt derivative (G).

Figure 13F:
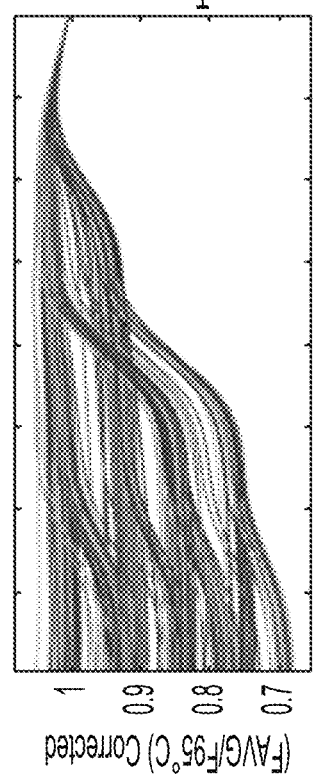
Figure 13G:
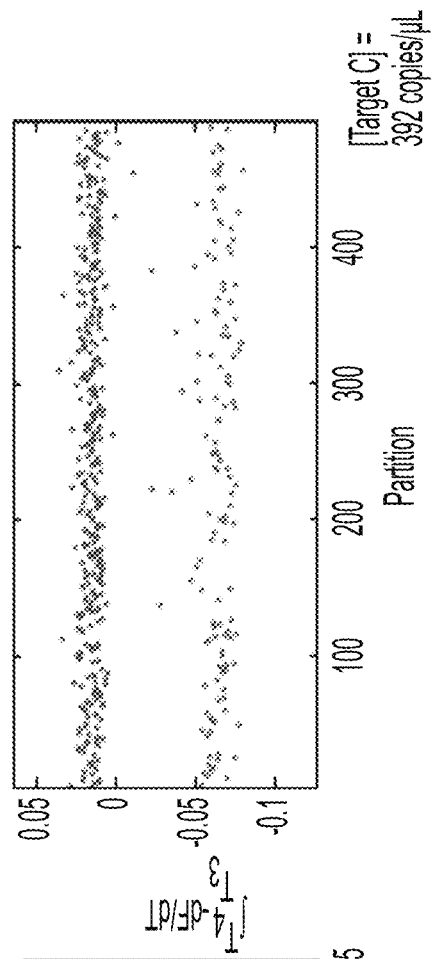
Figure 13H:
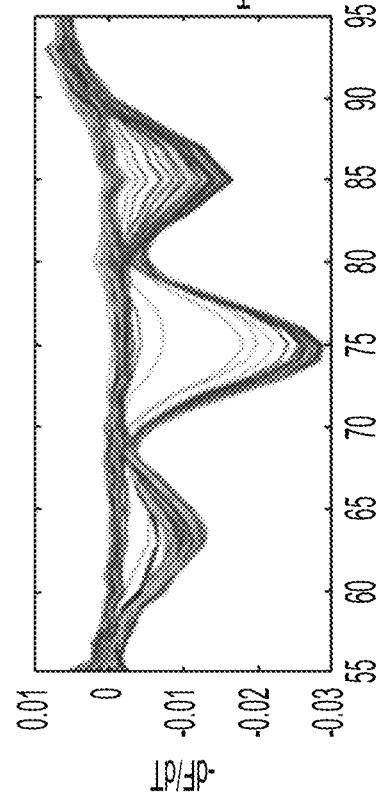

Classification of partitions based on melt data acquired at the probe annealling temperature resulted in identification of four distinct clusters corresponding to 0 target, one-target occupied, two target-occupied and three target-occupied partitions (FIG. 13B). However, melt analysis is required to determine the specific target occupancy of one- and two-target occupied partitions. To determine the quantity of target A present in the sample, the integral of the first melt profile was calculated and classification was carried out for each partition (FIG. 13D). The same process was carried out for the two remaining templates (FIGS. 13F&H). Based on this analysis, the measured concentration of target A was 692 copies/µL, target B was 537 copies/µL and target C was 392 copies/µL.

Multiplex Discrete Melt Analysis

Figure 14E:
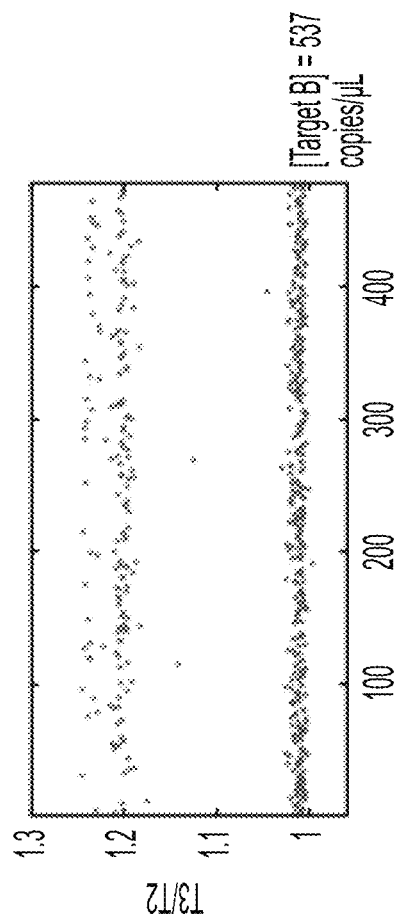
FIG. 14: Multiplex Discrete Melt Analysis. A: Fluorescence v. temperature plot for partitions of the sample shown in FIG. 13 measured at temperatures T1, T2, T3 and T4; B: Average fluorescence intensity per partition at 57° C. normalized to average fluorescence intensity per partition at 95° C.; C: Fluoresence v. temperature plot of the data from A after normalization to correct for system-induced partition variability; D: Ratio of fluorescence intensity per partition calculated for the first temperature interval (T2/T1); E: Fluoresence v. temperature plot of the data from C after normalization to correct for light- and temperature-dependent fluorescence decay; F: Ratio of fluorescence intensity per partition calculated for the second temperature interval (T3/T2); G: Ratio of fluorescence intensity per partition calculated for the third temperature interval (T4/T3). Again the calculated average number of copies per partition is used to determine specific target concentrations.
Figure 14F:
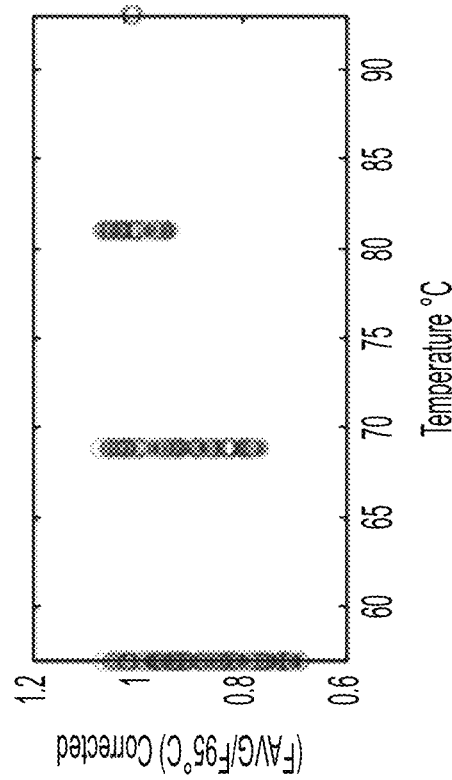
Figure 14G:
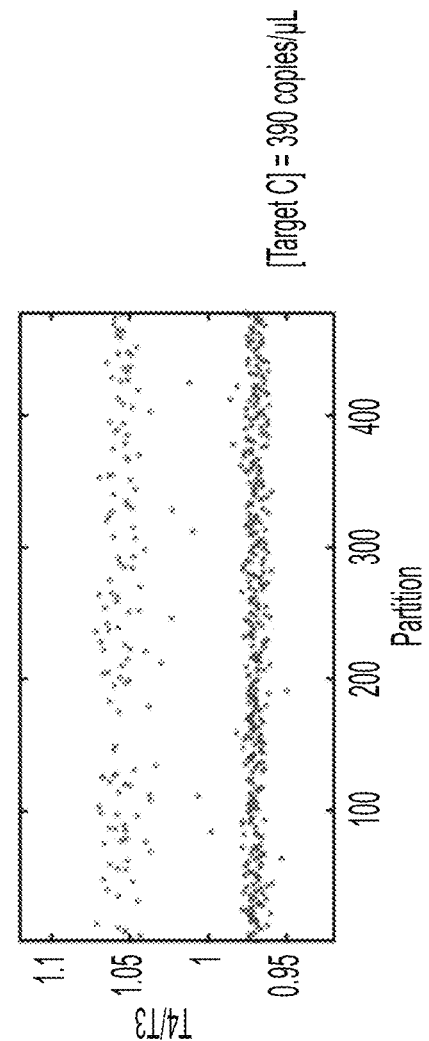

Sample reactions were prepared, digitized and thermal cycled as described previously. Melt images were acquired at four temperatures, $T_1=57°$ C., $T_2=69°$ C., $T_3=81°$ C., $T_4=93°$ C., and the average intensity of each partition was measured for the four images (FIG. 14A), normalized to 95° C. (FIG. 14C), and corrected for temperature- and light-dose dependence (FIG. 14E). Also shown is the 1D amplitude plot for all partitions in the 57° C. image which can be used to classify partitions as containing zero, one, two or all three targets (FIG. 14B). To determine the concentration of template A, the ratio of $T_2/T_1$ was determined (FIG. 14D). Partitions were classified using k-means, and the target concentration was determined using Equation 1. For template B, the ratio of $T_3/T_2$ was determined, partitions were classified using k-means and Equation 1 was employed (FIG. 14F). Lastly, for template C, the ratio of $T_4/T_3$ was determined, partitions were classified using k-means and template concentration was determined with Equation 1 (FIG. 14G). As was demonstrated in the singleplex case, discrete melt analysis in a multiplex reaction resulted in estimated concentrations that are virtually identical to those measured in continuous melt analysis. The calculated target concentrations of both singleplex and multiplex continuous vs discrete melt analysis are shown in Table 1.

TABLE 1

Calculated target concentrations using Continuous and Discrete Melt Analysis from partitions containing either single or multiple different targets.

| Target | Continuous | Discrete | Difference |
|---|---|---|---|
| Single-Plex Target Quantification | | | |
| B | 1,038 | 1,050 | −1.2% |
| Multi-Plex Target Quantification | | | |
| A | 692 | 704 | −1.7% |
| B | 537 | 537 | 0% |
| C | 392 | 390 | 0.5% |

Example 7 dPCR Workflow Using Cleavable Probes

This example provides an exemplary workflow for dPCR analysis using target-specific probes having predetermined melt profiles as described in U.S. application Ser. No. 14/823,288. Such probes exhibit distinguishable signals based on whether the probes are in duplex conformation as a result of encountering target nucleic acids, or whether they are in single stranded conformation. Note that for these probes, maximal fluorescence can be detected at any temperature prior to encountering target nucleic acid as a result of a fluorophore coupled to the probe, or after encountering target nucleic acid at temperatures above the predetermined Tm of the duplex, when the quencher incorporated into the probe is separated from the fluorophore as the intramolecular duplex is dissociated at these temperatures. This workflow is not necessarily limited to these probes, and may be applied to other types of probes having similar labeling schemes.

Figure 15:
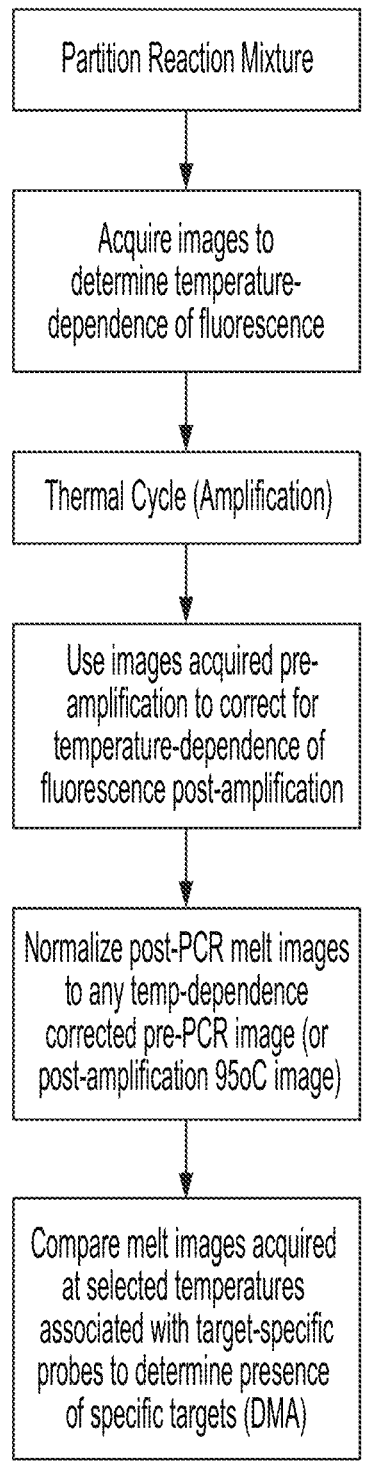
FIG. 15: dPCR Workflow for Discrete Melt Analysis: Example of workflow for dPCR Melt Analysis using multiple target-specific probes in each partition.

Discrete melt image analysis for dPCR reactions requires 3 key steps to ensure accurate interpretation of melt data and optimal classification of partitions into negative or positive partitions: 1) Correct measured fluorescence values for variations in fluorescence intensity as a result of temperature dependence of fluorescence; 2) Normalize measured fluorescence values for system-dependent fluorescence variability (e.g. optical non-uniformity or partition volume variations); and 3) determine presence of targets by detecting fluorescence intensity changes at preselected temperatures that are higher than and lower than the preselected Tms of probes. FIG. 15 provides an exemplary workflow for performing these steps.

In the first step after partitioning, images are acquired at a range of temperatures prior to thermal cycling to determine variations in fluorescence intensity due to temperature. The temperatures can be selected to correspond to those that will be used for DMA after thermal cycling, or a larger range of temperatures (e.g. every degree between the lowest and highest temperatures used for DMA) can be selected, or a previously acquired set of images for each fluorescent dye can be used.

Corrections for temperature dependence of fluorescence can be applied to images acquired after thermal cycling in a number of ways: i) Fit a curve to the average intensity values calculated for partitions at the various temperatures prior to amplification and use that expression to correct post-amplification images at the relevant temperatures; ii) acquire images for partitions at the temperatures used for DMA prior to amplification and normalize each post-amplification image with the corresponding pre-amplification image; iii) derive appropriate correction expressions at selected temperatures from an exemplary set of data and apply these to images taken after amplification at the selected temperatures; and iv) use intensity values associated with negative partitions post-amplification to correct integrated intensity values in positive partitions. In this last example, negative partition intensities in an image acquired at a single temperature substitute for partition intensities determined from a pre-amplification image acquired at the same temperature. In a preferred embodiment, the method described in (ii) is used as this method provides the advantage of simultaneously normalizing images for system-dependent fluorescence variability. In another embodiment, correction for temperature dependence of fluorescence is performed, followed by normalization using any image taken prior to amplification. Similarly, an image acquired at 95° C. after amplification and corrected for temperature-dependent fluorescence variations can be used for normalization. It is also possible to substitute an image acquired for a passive reference dye such as ROX for normalization.

After images have been corrected and normalized as described above, comparisons of fluorescence intensities from images acquired at a temperature lower than and a temperature higher than the predetermined Tm for each probe can be made to determine if a target is present. A person skilled in the art will recognize that comparisons of intensities may involve calculating ratios or differences in intensity measurements acquired at different temperatures. In addition, a person skilled in the art will recognize that calculations may be carried out using detected intensity values, or integrated or averaged intensities for each region of interest. Regardless, for each target investigated, results are expected to cluster into one of two groups for each partition, positive partitions or negative partitions. In a multiplexed scenario, multiplex categories of positive partitions can be expected as some partitions will contain multiple targets. This clustering should allow a threshold for distinguishing positive and negative partitions to be determined manually or using classification algorithms. In particular, the pre-amplification images acquired at various temperatures should aid in establishing statistics around the expected intensity (including mean and standard deviation) of negative partitions.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for determining the presence of a first target nucleic acid sequence in a sample, the method comprising:
    a) contacting, under specific hybridization conditions, the sample with a first cleavable, target-specific probe capable of specifically hybridizing to the first target nucleic acid sequence if present in a reaction mixture;
    b) cleaving the first probe that is specifically hybridized to the first target nucleic acid sequence to form a first truncated probe;
    c) providing conditions to cause the first truncated probe to hybridize to a first capture sequence;
    d) extending the first truncated probe to form a first duplex nucleic acid having a first predetermined Tm and a signal-generating label;
    e) measuring a first signal at a temperature below the first predetermined Tm and a second signal at a temperature above the first predetermined Tm without measuring a signal at the first predetermined Tm; and
    f) determining the presence of the first target nucleic acid sequence by detecting a change between the first and second signals.

2. The method of claim 1, further comprising contacting the sample with a second cleavable probes, the second cleavable probe being specific for a second target nucleic acid sequence, wherein, in the presence of the second target nucleic acid sequence, the second cleavable probe forms a second duplex nucleic acid having a second predetermined Tm that is higher than the first predetermined Tm and higher than the temperature at which the second signal is measured, and wherein the first and second duplex nucleic acids have the same signal-generating label, further comprising the steps of, measuring a third signal at a temperature above the second predetermined Tm, and determining the presence of the second target nucleic acid sequence by detecting a change between the second and third signals.

3. The method of claim 2, wherein signal is measured at no more than n+1 different temperatures, wherein n is the number of different cleavable probes in the reaction mixture.

4. The method of claim 2, wherein the first and second predetermined Tms are at least 2 degrees Celsius different.

5. The method of claim 2, wherein the first and second predetermined Tms are at least 5 degrees Celsius different.

6. The method of claim 2, wherein the first and second predetermined Tms are at least 10 degrees Celsius different.

7. The method of claim 2, further comprising contacting the sample with a third cleavable probe, the third cleavable probe being specific for a third target nucleic acid sequence, wherein, in the presence of the third target nucleic acid sequence, the third cleavable probe forms a third duplex nucleic acid having a third predetermined Tm that is higher than the second predetermined Tm and higher than the temperature at which the third signal is measured, and wherein the first, second and third duplex nucleic acids have the same signal-generating label, further comprising the steps of measuring a fourth signal at a temperature above the third predetermined Tm, and determining the presence of the third target nucleic acid sequence by detecting a change between the third and fourth signals.

8. The method of claim 7, wherein the first, second and third predetermined Tms are at least 2 degrees Celsius different.

9. The method of claim 7, wherein the first, second and third predetermined Tms are at least 5 degrees Celsius different.

10. The method of claim 7, wherein the first, second and third predetermined Tms are at least 10 degrees Celsius different.

11. The method of claim 1, wherein the first capture sequence and first truncated probe are unimolecular.

12. The method of claim 1, wherein the first capture sequence and first truncated probe are bimolecular.

13. The method of claim 1, wherein the first target nucleic acid is determined to be present when the ratio between the first signal and the second signal exceeds a predetermined threshold.

14. The method of claim 1, wherein a signal is not measured at a temperature within 2 degrees Celsius of the first predetermined Tm.

15. The method of claim 1, wherein a signal is not measured at a temperature within 5 degrees Celsius of the first predetermined Tm.

16. The method of claim 1, wherein the first cleavable probe is labeled with a first member of a reporter-quencher pair and adopts a first conformation when hybridized to the first target nucleic acid sequence.

17. The method of claim 16, wherein specific hybridization of the first cleavable probe to the first target sequence results in cleavage of the probe at a cleavage site, release of the first truncated probe from the first target nucleic acid sequence to adopt a second conformation, and strand extension from the cleavage site.

18. The method of claim 17, wherein strand extension includes incorporating a second member of a reporter-quencher pair that interacts with the first member of the reporter-quencher pair.

19. The method of claim 17, wherein the first conformation is a linear conformation and the second conformation is a hairpin conformation.

20. A method for detecting the presence or absence of a target nucleic acid sequence in a sample, the method comprising:
 a) contacting, under specific hybridization conditions, the sample with at least one cleavable probe capable of specifically hybridizing to the target nucleic acid sequence if present, the cleavable probe including a signal-generating label;
 b) cleaving the probe that is specifically hybridized to the target nucleic acid sequence to form a truncated probe;
 c) providing conditions to cause the truncated probe to hybridize to a capture sequence that includes a sequence that is complementary to the truncated probe;
 d) extending the truncated probe using the capture sequence as a template, to form a double stranded probe having a predetermined Tm;
 e) measuring a first signal from the signal-generating label at a first temperature below the predetermined Tm and a second signal at a second temperature above the predetermined Tm, without measuring a signal at the predetermined Tm; and
 f) determining the presence of the target nucleic acid sequence by detecting a change in signal measured at the first temperature and the second temperature.

21. A method for detecting the presence of a target nucleic acid in a sample, the method comprising the steps of:
 a) providing a reaction mixture comprising the sample, at least one labeled, cleavable target-specific probe capable of specifically hybridizing to the target nucleic acid sequence if present in the reaction mixture, and the label being a first member of a reporter-quencher pair;
 b) measuring a first signal from the labeled target-specific probe in the reaction mixture;
 c) providing specific hybridization conditions to cause the labeled cleavable target-specific probe to hybridize to the target nucleic acid sequence if present in the reaction mixture;
 d) cleaving the probe that is specifically hybridized to the target nucleic acid sequence to form a truncated probe;
 e) providing conditions to cause the truncated probe to hybridize to a capture sequence;
 f) extending the truncated probe to form a duplex nucleic acid having a second member of the reporter-quencher pair and a predetermined Tm;
 g) measuring a second signal at a temperature below the predetermined Tm; and
 h) detecting the presence of the target nucleic acid when there is a difference between the first and second signals that exceeds a predetermined threshold.

22. The method of claim 21, wherein the capture sequence and truncated probe are unimolecular and hybridize to form a hairpin probe.

23. The method of claim 21, wherein the capture sequence and truncated probe are bi-molecular.

24. The method of claim 21, wherein the target specific probe comprises a first non-natural nucleotide to which the first member of the reporter-quencher pair is attached and the duplex nucleic acid comprises a second non-natural nucleotide to which the second member of the reporter-quencher pair is attached, and the first and second non-natural nucleotides are capable of base-pairing with each other.

25. The method of claim 24, wherein the first and second non-natural nucleotides are one or the other of isoC and isoG.

* * * * *